United States Patent [19]
An et al.

[11] Patent Number: 5,882,864
[45] Date of Patent: Mar. 16, 1999

[54] BIOMARKERS AND TARGETS FOR DIAGNOSIS, PROGNOSIS AND MANAGEMENT OF PROSTATE DISEASE

[75] Inventors: Gang An; S. Mark O'Hara, both of Oklahoma City; David Ralph, Edmond; Robert Veltri, Oklahoma City, all of Okla.

[73] Assignee: Urocor Inc., Oklahoma City, Okla.

[21] Appl. No.: 692,787

[22] Filed: Jul. 31, 1996

Related U.S. Application Data

[60] Provisional application No. 60/001,655 Jul. 31, 1995 and provisional application No. 60/013,611, Jan. 11, 1996.

[51] Int. Cl.$^6$ .......................... C12Q 1/68; C07H 21/04; C12P 19/34
[52] U.S. Cl. .......................... 435/6; 435/91.2; 435/91.5; 435/91.51; 536/24.31; 536/24.33; 536/23.5
[58] Field of Search .......................... 435/6, 91.2, 91.5, 435/91.1, 91.51; 536/24.33, 24.31, 23.5; 935/6, 8, 17, 77, 78

[56] References Cited

U.S. PATENT DOCUMENTS

| | | | |
|---|---|---|---|
| 5,262,311 | 11/1993 | Pardee et al. | 435/91.2 |
| 5,633,161 | 5/1997 | Shyjan | 435/325 |
| 5,639,656 | 6/1997 | Wright, Jr. | 435/344.1 |
| 5,665,547 | 9/1997 | Pardee et al. | 435/6 |

FOREIGN PATENT DOCUMENTS

WO 94/10343  5/1994  WIPO .............................. C12Q 1/68

OTHER PUBLICATIONS

Deguchi et al. Cancer Research 53:5350–5354, Nov., 1993.
Garcia–Arenas. et al. Mol. & Cell. Endocrin. 111;29–37, Apr. 28, 1995.
Prashar et al P.N.A.S., USA 93:659–663, Jan., 1996.
Adam et al. Proceedings: American Association for Cancer Research 36:25, Mar., 1995.
Bussemakers et al. Cancer Research 51:606–611, Jan., 1991.
Kawasaki et al. in PCR Technology: Principles and Applications For DNA Amplification, Stockton Press New York, pp. 89–97, 1989.
Badalament et al., "An algorithm for predicting nonorgan confined prosate cancer using the results obtained from sextant core biopsies with prostate specific antigen level," *J. Urol.*, 156:1375–1380, 1996.
Veltri et al., "Ability to predict biochemical progression using gleason score and a computer–generated quantitative nuclear grade derived form cancer cell nuclei," *Urology*, 48(5):685–691, 1996.
An et al., "Identification of Novel Gene Markers in Prostate Disease by RNA Fingerprinting," *Proceedings of the American Association for Cancer Research Annual Meeting*, 37(0):248, 1996. Abstract No. 1692.
An et al., "Sensitive, Nonradioactive Differential Display Method Using Chemiluminescent Detection," *Biotechniques*, 20(3):342, 344, 346, 1996.
Blok et al., "Isolation of cDNAs That Are Differentlially Expressed Between Androgen–dependent and Androgen–independent Prostate Carcinoma Cells Using Differential Display PCR", *Prostate*, 26(4):213–224, 1995.
Hamdy et al., Circulating prostate Specific Antigen–positive Cells Correlate with Metastatic Prostate Cancer, *British Journal of Urology*, 69(4):392–396, 1992.

(List continued on next page.)

*Primary Examiner*—Carla J. Myers
*Attorney, Agent, or Firm*—Arnold White & Durkee

[57] ABSTRACT

Disclosed are diagnostic techniques for the detection of human prostate cancer. Genetic probes and methods useful in monitoring the progression and diagnosis of prostate cancer are described. The invention relates particularly to probes and methods for evaluating the presence of RNA species that are differentially expressed in prostate cancer compared to normal human prostate or benign prostatic hyperplasia.

64 Claims, 15 Drawing Sheets

OTHER PUBLICATIONS

Robson et al., Identificatin of Prostatic Androgen Regulated Genes Using the Differential Display Technique, *Proceedings of the American Association for Cancer Research Anual Meetings*, 36:266, 1995. Abstract No. 1589.

EMBL. Sequence Data Library, Heidelberg, BRD, XP002019347, Accession No. W67972.

PCT Search Report mailed Mar. 7, 1997.

Alcaraz, Antonio, et al., "Aneuploidy and Aneusomy of Chromosome 7 Detected by fluorescence in Situ Hybridization Are Makers of Poor Prognosis in Prostate Cancer", *Cancer Research*, 54:3998–4002, Aug. 1994.

An, G., et al., Isolation of Genes differentially expressed in prostate cancer cells with metastatic potential by arbitrarily–primed differential analyses (ADA), *Proc. Amer. Assn. Canc. Res.*, 36:82 (#491), 1995.

Bookstein, Robert, et al. "Suppression of Tumorigenicity of Human Prostate Carcinoma Cells by Replacing a Mutated RB Gene", *Science*, 247:712–715, Feb., 1990.

Bookstein, Robert, et al., "Promoter deletion and loss of retinoblastoma gene expression in human prostate carcinoma", *Proc. Natl. Acad. Sci. USA*, 87:7762–7766, Oct., 1990.

Bova, G. Steven, et al., "Homozygous Deletion and Frequent Allelic Loss of Chromosome 8p22 Loci in Human Prostate Cancer", *Cancer Research*, 53:3869–3873, Sep., 1993.

Carter, Bob S., et al., "Allelic loss of chromosomes 16q and 10q in human prostate cancer", *Proc. Natl. Acad. Sci. USA*, 87:8751–8755, Nov., 1990.

Chen, Michael E., et al., "Androgen–Independent Human Prostate Cancer Progression: The Isolation of Novel Stage–Specific Sequences Using Differential mRNA Display", *Proc. Natl. Urol. Assn.*, 153:267A, 1995.

Donohue, Patrick J., et al., "A Delayed–early Gene Activated by Fibroblast Growth Factor–1 Encodes a Protein Related to Aldose Reductase", *The Journal of Biological Chemistry*, 269(11):8604–8609, 1994.

Dumont, Francis J., et al., "Relationship Between Multiple Biologic Effects of Rapamycin and the Inhibition of pp70S6 Protein Kinase Activity", *Journal of Immunology*, 992–1003, 1994.

Isaacs, William B., et al., "Molecular Biology of Prostate Cancer", *Seminars in Oncology*, 21(5):514–521, Oct., 1994.

Isaacs, William B., et al., "Wild–Type p53 Suppresses Growth of Human Prostate Cancer Cells Containing Mutant p53 Alleles", *Cancer Research*, 51:4716–4720, Sep., 1991.

Liang, Peng and Pardee, Arthur B., "Differential Display of Eukaryotic Messenger RNA by Means of the Polymerase Chain Reaction", *Science*, 257:967–971, Aug., 1992.

Liang, Peng, et al., "Differential Display and Cloning of Messenger RNAs from Human Breast Cancer versus Mammary Epithelial Cells", *Cancer Research*, 52:6966–6968, Dec., 1992.

Macoska, Jill A., et al., "Fluorescence in Situ Hybridization Analysis of 8p Allelic Loss and Chromosome 8 Instability in Human Prostate Cancer", *Cancer Research*, 54:3824–3830, Jul., 1994.

Mok, Samuel C., et al., "Molecular Cloning of Differentially Expressed Genes in Human Epithelial Ovarian Cancer", *Gynecological Oncology*, 52:247–252, 1994.

Morton, Donald L., et al., "Multivariate Analysis of the Relationship between Survival and the Microstage of Primary Melanoma by Clark Level and Breslow Thickness", *Cancer*, 71(11):3737–3743, Jun., 1993.

Morton, Ronald A., et al., "Reduction of E–Cadherin Levels and Deletion of the α–Catenin Gene in Human Prostate Cancer Cells", *Cancer Research*, 53:3585–3590, Aug., 1993.

Qiao, Liang, et al., "Effects of Suramin on Expression of Proliferation Associated Nuclear Antigens in DU–145 Prostate Carcinoma Cells", *Biochemical and Biophysical Research Communications*, 201(2):581–588, Jun., 1994.

Riber, Manuel and Rieber, Mary Strasberg, "Cyclin–dependent Kinase 2 and Cyclin A Interaction with E2F Are Targets for Tyrosine Induction of B16 Melanoma Terminal Differentiation", *Cell Growth & Differentiation*, 5:1339–1346, Dec., 1994.

Sager, Ruth, et al., "Identification by differential display of alpha–6 integrin as a candidate tumor suppressor gene", *Methodology Communications*, 7:964–970, Jul., 1993.

Scott, Gary K., et al., "A Truncated Intracellular HER2/neu Receptor Produced by Alternative RNA Processing Affects Growth of Human Carcinoma Cells"*Molecular and Cellular Biology*, 13(4):2247–2257, Apr., 1993.

Slamon, Dennis J., et al., "Expression of Cellular Oncogenes in Human Malignancies", *Science*, 224:256–262, Apr., 1984.

Takahashi, Satoru, et al., "Potential Markers of Prostate Cancer Aggressiveness Detected by Fluorescence in Situ Hybridization in Needle Biopsies", *Cancer Research*, 54:3574–3576, Jul., 1994.

Umbas, Rainy, et al., "Expression of the Cellular Adhesion Molecule E–Cadherin Is Reduced or Absent in High–Grade Prostate Cancer", *Cancer Research*, 52:5104–5109, Sep., 1992.

Visakorpi, Tapio, et al., "Sensitive Detection of Chromosome Copy Number Abberations in Prostate Cancer by Fluorescence In Situ Hydbridization", *Americal Journal of Pathology*, 145(3):624–630, Sep., 1994.

Watson, Mark A. and Fleming, Timothy P., "Isolation of Differentially Expressed Sequence tags from Human Breast Cancer", *Cancer Research*, 54:4598–4602, Sep., 1994.

Webb, Karen S. Gerald H. Lin, "Urinary Fibronectin–Potential as a Biomarker in Prostatic Cancer", *Investigative Urology*, 17(5)401–404, Mar., 1980.

Welsh, John, et al., "Arbitrarily primed PCR fingerprinting of RNA", *Nucleic Acids Research*, 20(19):4965–4970, 1990.

Wong, Kwong–Kwok, et al., "Identification of differentially expressed RNA in human ovarian carcinoma cells by arbitrarily primed PCR fingerprinting of total RNAs", *Intl J of Onc*, 3:13–17, 1993.

BIOMARKERS AND TARGETS FOR DIAGNOSIS, PROGNOSIS AND MANAGEMENT OF PROSTATE DISEASE

This application claims the benefit under 35 U.S.C. section 119(e) of U.S. provisional application 60/001,655, filed Jul. 31, 1995, now abandoned and U.S. provisional application 60/013,611, filed Jan. 11, 1996, now abandoned.

BACKGROUND OF THE INVENTION

A. Field of the Invention

The present invention relates generally to nucleic acid sequences useful as probes for the diagnosis of cancer and methods relating thereto. More particularly, the present invention concerns probes and methods useful in diagnosing, identifying and monitoring the progression of diseases of the prostate through measurements of gene products.

B. Description of the Related Art

Carcinoma of the prostate (PCA) is the second-most frequent cause of cancer related death in men in the United States (Boring, 1993). The increased incidence of prostate cancer during the last decade has established prostate cancer as the most prevalent of all cancers (Carter and Coffey, 1990). Although prostate cancer is the most common cancer found in United States men, (approximately 200,000 newly diagnosed cases/year), the molecular changes underlying its genesis and progression remain poorly understood (Boring et al., 1993). According to American Cancer Society estimates, the number of deaths from PCA is increasing in excess of 8% annually.

An unusual challenge presented by prostate cancer is that most prostate tumors do not represent life threatening conditions. Evidence from autopsies indicate that 11 million American men have prostate cancer (Dbom, 1983). These figures are consistent with prostate carcinoma having a protracted natural history in which relatively few tumors progress to clinical significance during the lifetime of the patient. If the cancer is well-differentiated, organ-confined and focal when detected, treatment does not extend the life expectancy of older patients.

Unfortunately, the relatively few prostate carcinomas that are progressive in nature are likely to have already metastasized by the time of clinical detection. Survival rates for individuals with metastatic prostate cancer are quite low. Between these two extremes are patients with prostate tumors that will metastasize but have not yet done so. For these patients, surgical removal of their prostates is curative and extends their life expectancy. Therefore, determination of which group a newly diagnosed patient falls within is critical in determining optimal treatment and patient survival.

Although clinical and pathologic stage and histological grading systems (e.g., Gleason's) have been used to indicate prognosis for groups of patients based on the degree of tumor differentiation or the type of glandular pattern (Carter and Coffey, 1989; Diamond et al., 1982), these systems do not predict the progression rate of the cancer. While the use of computer-system image analysis of histologic sections of primary lesions for "nuclear roundness" has been suggested as an aide in the management of individual patients (Diamond et al., 1982), this method is of limited use in studying the progression of the disease.

Recent studies have identified several recurring genetic changes in prostate cancer including: 1) allelic loss (particularly loss of chromosome 8p and 16q) (Bova, et al., 1993; Macoska et al., 1994; Carter et al., 1990); 2) generalized DNA hypermethylation (Isaacs et al., 1994); 3) point mutations or deletions of the retinoblastoma (Rb) and p53 genes (Bookstein et al., 1990a; Bookstein et al., 1990b; Isaacs et al., 1991); 4) alterations in the level of certain cell-cell adhesion molecules (i.e., E-cadherin/alpha-catenin) (Carter et al., 1990; Morton et al., 1993; Umbas et al., 1992) and aneuploidy and aneusomy of chromosomes detected by fluorescence in situ hybridization (FISH), particularly chromosomes 7 and 8 Macoska et al., 1994; Visakorpi et al., 1994; Takahashi et al., 1994; Alcaraz et al., 1994).

The analysis of DNA content/ploidy using flow cytometry and FISH has been demonstrated to have utility predicting prostate cancer aggressiveness (Pearsons et al., 1993; Macoska et al., 1994; Visakorpi et al., 1994; Takahashi et al., 1994; Alcaraz et al., 1994; Pearsons et al., 1993), but these methods are expensive, time-consuming, and the latter methodology requires the construction of centromere-specific probes for analysis.

Specific nuclear matrix proteins have been reported to be associated with prostate cancer. (Partin et al., 1993). However, these protein markers apparently do not distinguish between benign prostate hyperplasia and prostate cancer. Martin et al., 1993). Unfortunately, markers which cannot distinguish between benign and malignant prostate tumors are of little value.

It is known that the processes of transformation and tumor progression are associated with changes in the levels of messenger RNA species (Slamon et al., 1984; Sager et al., 1993; Mok et al., 1994; Watson et al., 1994). Recently, a variation on PCR analysis known as RNA fingerprinting has been used to identify messages differentially expressed in ovarian or breast carcinomas (Liang et al., 1992; Sager et al., 1993; Mok et al., 1994; Watson et al., 1994). By using arbitrary primers to generate "fingerprints" from total cell RNA, followed by separation of the amplified fragments by high resolution gel electrophoresis, it is possible to identity RNA species that are either up-regulated or down-regulated in cancer cells. Results of these studies indicated the presence of several markers of potential utility for diagnosis of breast or ovarian cancer, including a6-integrin (Sager et al., 1993), DEST001 and DEST002 (Watson et al., 1994), and LF4.0 (Mok et al., 1994).

There remain, however, deficiencies in the prior art with respect to the identification of the genes linked with the progression of prostate cancer and the development of diagnostic methods to monitor disease progression. Likewise, the identification of genes which are differentially expressed in prostate cancer would be of considerable importance in the development of a rapid, inexpensive method to diagnose prostate cancer.

SUMMARY OF THE INVENTION

The present invention addresses deficiencies in the prior art by identifying and characterizing RNA species that are differentially expressed in human prostate diseases, along with providing methods for identifying such RNA species. These RNA species and the corresponding encoded protein species have utility, for example, as markers of prostate disease and as targets for therapeutic intervention in prostate disease. The disclosed methods may also be applied to other tissues in order to identify differentially expressed genes that are markers of different physiological states of that tissue.

The identified markers of prostate disease can in turn be used to design specific oligonucleotide probes and primers.

When used in combination with nucleic acid hybridization and amplification procedures, these probes and primers permit the rapid analysis of prostate biopsy core specimens, serum samples, etc. This will assist physicians in diagnosing prostate disease and in determining optimal treatment courses for individuals with prostate tumors of varying malignancy. The same probes and primers may also be used for in situ hybridization or in situ PCR detection and diagnosis of prostate cancer.

The identified markers of prostate disease may also be used to identify and isolate full length gene sequences, including regulatory elements for gene expression, from genomic human DNA libraries. The cDNA sequences identified in the present invention are first used as hybridization probes to screen genomic human DNA libraries by standard techniques. Once partial genomic clones have been identified, full-length genes are isolated by "chromosomal walking" (also called "overlap hybridization"). See, Chinault & Carbon "Overlap Hybridization Screening: Isolation and Characterization of Overlapping DNA Fragments Surrounding the LEU2 Gene on Yeast Chromosome III." *Gene* 5: 111–126, 1979. Nonrepetitive sequences at or near the ends of the partial genomic clones are then used as hybridization probes in further genomic library screening, ultimately allowing the isolation of entire gene sequences for the cancer markers of interest. Those experienced in the art will realize that full length genes may be obtained using the small expressed sequence tags (ESTs) described herein using technology currently available (Sambrook et al., 1989; Chinault & Carbon, 1979).

The identified markers may also be used to identify and isolate cDNA sequences. In the practice of this method, the EST sequences identified in the present disclosure are used as hybridization probes to screen human cDNA libraries by standard techniques. In a preferred practice, a high quality human cDNA library is obtained from commercial or other sources. The library is plated on, for example, agarose plates containing nutrients, antibiotics and other standard ingredients. Individual colonies are transferred to nylon or nitrocellulose membranes and the EST probes are hybridized to complementary sequences on the membranes. Hybridization is detected by radioactive or enzyme-linked tags associated with the hybridized probes. Positive colonies are grown up and sequenced by, for example, dideoxy nucleotide sequencing or similar methods well known in the art. Comparison of cloned cDNA sequences with known human or animal cDNA or genomic sequences is performed using computer programs and databases well known to the skilled practitioner.

In one embodiment of the present invention, the isolated nucleic acids of the present invention are incorporated into expression vectors and expressed as the encoded proteins or peptides. Such proteins or peptides may in certain embodiments be used as antigens for induction of monoclonal or polyclonal antibody production.

One aspect of the present invention is thus, oligonucleotide hybridization probes and primers that hybridize selectively to specific markers of prostate disease. These probes and primers are selected from those sequences designated herein as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45, SEQ ID NO:46 and SEQ ID NO:47. The availability of probes and primers specific for such unique markers provides the basis for diagnostic kits useful for distinguishing between BPH, prostate organ confined cancer and prostate tumors with potential for metastatic progression.

In one broad aspect, the present invention encompasses kits for use in detecting prostate disease cells in a biological sample. Such a kit may comprise one or more pairs of primers for amplifying nucleic acids corresponding to prostate disease marker genes. The kit may further comprise samples of total mRNA derived from tissue of various physiological states, such as normal, BPH confined tumor and metastatically progressive tumor, for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting prostate cancer cells in a biological sample comprising oligonucleotide probes effective to bind with high affinity to markers of prostate disease in a Northern blot assay and containers for each of these probes. In a further embodiment, the invention encompasses a kit for use in detecting prostate cancer cells in a biological sample comprising antibodies specific for proteins encoded by the nucleic acid markers of prostate disease identified in the present invention.

In one broad aspect, the present invention encompasses methods for treating prostate cancer patients by administration of effective amounts of antibodies specific for the peptide products of prostate cancer markers identified herein, or by administration of effective amounts of vectors producing anti-sense messenger RNAs that bind to the nucleic acid products of prostate cancer markers, thereby inhibiting expression of the protein products of prostate cancer marker genes. Antisense nucleic acid molecules may also be provided as RNAs, as some stable forms or RNA are now known in the art with a long half-life that may be administered directly, without the use of a vector. In addition, DNA constructs may be delivered to cells by liposomes, receptor mediated transfection and other methods known in the art. The method of delivery does not, in and of itself constitute the present invention, but it is the delivery of an agent that will inhibit or disrupt expression of the targeted mRNAs as defined herein that constitute a critical step of this embodiment of the invention. Therefore, delivery of those agents, by any means known in the art would be encompassed by the present claims.

One aspect of the present invention is novel isolated nucleic acid segments that are useful as described herein as hybridization probes and primers that specifically hybridize to prostate disease markers. These disease markers, including both known genes and previously undescribed genes, are described herein as those mRNA species shown to be differentially expressed (either up- or down-regulated) in a prostate disease state as compared to a normal prostate. The novel isolated segments are designated herein as SEQ ID NO:1, SEQ ID NO:2, SEQ ID NO:3, SEQ ID NO:4, SEQ ID NO:5, SEQ ID NO:10, SEQ ID NO:11, SEQ ID NO:12, SEQ ID NO:13, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45 and SEQ ID NO:46. The invention further comprises an isolated nucleic acid of between about 14 and about 100 bases in length, either identical to or complementary to a portion of the same length occurring within the disclosed sequences.

The present invention comprises proteins and peptides with amino acid sequences encoded by the aforementioned isolated nucleic acid segments. The invention also comprises methods for identifying biomarkers for prognostic or diagnostic assays of human prostate disease, using the techniques of RNA fingerprinting to identify RNAs that are differentially expressed between prostate cancers versus normal or benign prostate. Such fingerprinting techniques may utilize an oligodT primer and an arbitrary primer, an oligodT primer alone or random hexamers or any other method known in the art.

The invention further comprises methods for detecting prostate cancer cells in biological samples, using hybridization primers and probes designed to specifically hybridize to prostate cancer markers. The hybridization probes are identified and designated herein as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45, SEQ ID NO:46 and SEQ ID NO:47. This method further comprises measuring the amounts of nucleic acid amplification products formed when primers selected from the designated sequences are used.

The invention further comprises the prognosis and/or diagnosis of prostate cancer by measuring the amounts of nucleic acid amplification products formed as above. The invention comprises methods of treating individuals with prostate cancer by providing effective amounts of antibodies and/or antisense DNA molecules which bind to the products of the above mentioned isolated nucleic acids. The invention further comprises kits for performing the above-mentioned procedures, containing amplification primers and/or hybridization probes.

The present invention further comprises production of antibodies specific for proteins or peptides encoded by SEQ ID NO:1, SEQ ID NO:2, SEQ ID NO:3, SEQ ID NO:4, SEQ ID NO:5, SEQ ID NO:10, SEQ ID NO:11, SEQ ID NO:12, SEQ ID NO:13, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45 and SEQ ID NO:46., and the use of those antibodies for diagnostic applications in detecting prostate cancer. The invention further comprises therapeutic treatment of prostate cancer by administration of effective doses of inhibitors specific for the aforementioned encoded proteins.

DETAILED DESCRIPTION OF THE INVENTION

Figure 1:
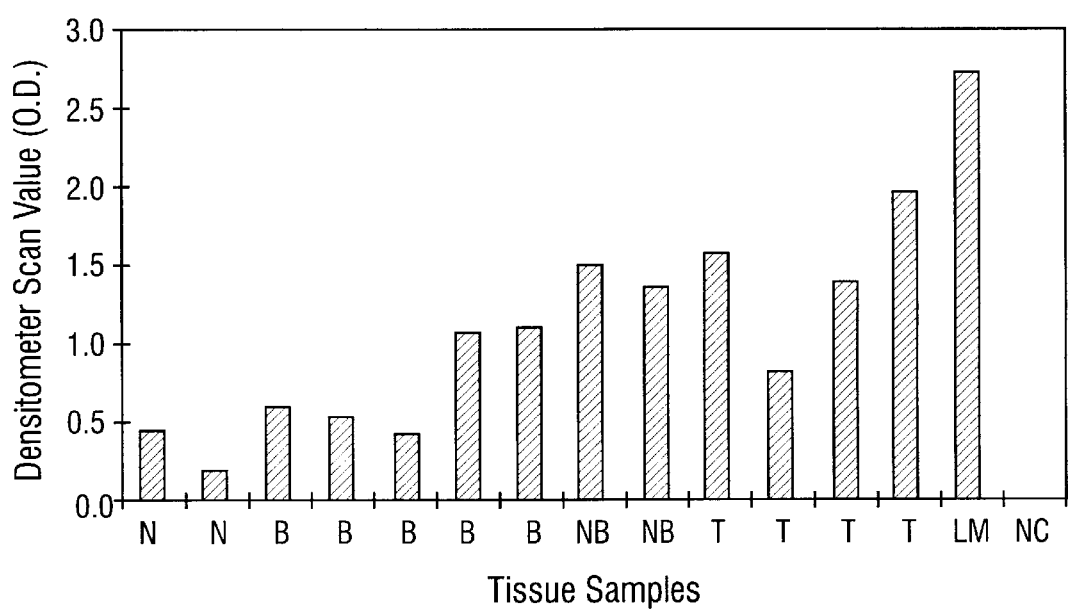
FIG. 1. Normalized quantitative RT-PCR of UC Band #25 (SEQ ID NO:1) shows that it is overexpressed in prostate cancers and benign prostate compared with normal prostate tissues. The levels are particularly high in metastatic prostate cancer. N=normal prostate, B=benign prostatic hyperplasia (BPH), NB=needle core biopsy of prostate cancer, T=primary prostate cancer, LM=metastatic lymph node prostate cancer, NC=negative control.

The present invention concerns the early detection, diagnosis, prognosis and treatment of prostate diseases, such as prostate cancer or benign prostatic hyperplasia (BPH). Markers of prostate disease, in the form of nucleic acid sequences isolated from human prostate tumors or prostate cancer cell lines, are disclosed. These markers are indicators of malignant transformation of prostate tissues and are diagnostic of the potential for metastatic spread of malignant prostate tumors.

Those skilled in the art will realize that the nucleic acid sequences disclosed will find utility in a variety of applications in prostate cancer detection, diagnosis, prognosis and treatment. Examples of such applications within the scope of the present invention comprise amplification of markers of prostate disease using specific primers, detection of markers of prostate disease by hybridization with oligonucleotide probes, incorporation of isolated nucleic acids into vectors, expression of RNA, peptides or polypeptides from the vectors, development of immunologic reagents corresponding to marker encoded products, and therapeutic treatments of prostate cancer using antibodies, anti-sense nucleic acids, or other inhibitors specific for the identified prostate cancer markers.

A. Nucleic Acids

As described herein, an aspect of the present disclosure is 26 markers of prostate disease, identified by RNA fingerprinting or quantitative RT-PCR. These include 20 previously unknown gene products, as well as nucleic acid products of the α6-integrin, PAP, fibronectin and cyclin A genes and a truncated nucleic acid product of the Her2/neu gene. The latter three gene products have been identified in other forms of cancer, but the present invention is the first report of overexpression in prostate cancer.

In one embodiment, the nucleic acid sequences disclosed herein will find utility as hybridization probes or amplification primers. These nucleic acids may be used, for example, in diagnostic evaluation of tissue samples or employed to clone full length cDNAs or genomic clones corresponding thereto. In certain embodiments, these probes and primers consist of oligonucleotide fragments. Such fragments should be of sufficient length to provide specific hybridization to a RNA or DNA tissue sample. The sequences typically will be 10–20 nucleotides, but may be longer. Longer sequences, e.g., 40, 50, 100, 500 and even up to fill length, are preferred for certain embodiments.

Nucleic acid molecules having contiguous stretches of about 10, 15, 17, 20, 30, 40, 50, 60, 75 or 100 or 500 nucleotides from a sequence selected from SEQ ID NO:1, SEQ ID NO:2, SEQ ID NO:3, SEQ ID NO:4, SEQ ID NO:5, SEQ ID NO:10, SEQ ID NO:11, SEQ ID NO:12, SEQ ID NO:13, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45 and SEQ ID NO:46 are contemplated. Molecules that are complementary to the above mentioned sequences and that bind to these sequences under high stringency conditions also are contemplated. These probes will be useful in a variety of hybridization embodiments, such as Southern and Northern blotting. In some cases, it is contemplated that probes may be used that hybridize to multiple target sequences without compromising their ability to effectively diagnose cancer.

Various probes and primers can be designed around the disclosed nucleotide sequences. Primers may be of any length but, typically, are 10–20 bases in length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one (9 to 19), where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

The values of n in the algorithm above for each of the nucleic acid sequences is: SEQ ID NO:1, n=391; SEQ ID NO:2, n=614; SEQ ID NO:3, n=757; SEQ ID NO:4, n=673; SEQ ID NO:5, n=358; SEQ ID NO:10, n=166; SEQ ID NO:11, n=107; SEQ ID NO:12, n=183; SEQ ID NO:13, n=92; SEQ ID NO:15, n=174; SEQ ID NO:16, n=132; SEQ ID NO:17, n=135; SEQ ID NO:18, n=415; SEQ ID NO:19, n=471; SEQ ID NO:20, n=209, SEQ ID NO:21, n=407, SEQ ID NO:22, n=267, SEQ ID NO:23, n=333, SEQ ID NO:45, n=369, and SEQ ID NO:46, n=301.

In certain embodiments, it is contemplated that multiple probes may be used for hybridization to a single sample. For example, a truncated form of Her2/neu could be detected by probing human tissue samples with oligonucleotides specific for the 5' and 3' ends of the full-length Her2/neu transcript.

A full-length Her2/neu transcript would bind both probes, while a truncated form of the Her2/neu transcript, indicative of transformed cells, would bind to the 5' probe but not to the 3' probe.

The use of a hybridization probe of between 14 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

The following codon chart may be used, in a site-directed mutagenic scheme, to produce nucleic acids encoding the same or slightly different amino acid sequences of a given nucleic acid:

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |

-continued

| Amino Acids | | | Codons | | | |
|---|---|---|---|---|---|---|
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C.

In certain embodiments, it will be advantageous to employ nucleic acid sequences of the present invention in combination with an appropriate means, such as a label for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

It will be understood that this invention is not limited to the particular probes disclosed herein and particularly is intended to encompass at least nucleic acid sequences that are hybridizable to the disclosed sequences or are functional sequence analogs of these sequences. For example, a partial sequence may be used to identify a structurally-related gene or the fill length genomic or cDNA clone from which it is derived. Those of skill in the art are well aware of the methods for generating cDNA and genomic libraries which can be used as a target for the above-described probes (Sambrook et al., 1989).

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

Where an expression product is to be generated, it is possible for the nucleic acid sequence to be varied while retaining the ability to encode the same product. Reference to the codon chart, provided above, will permit those of skill in the art to design any nucleic acid encoding for the product of a given nucleic acid.

B. Encoded Proteins

Once the entire coding sequence of a marker-associated gene has been determined, the gene can be inserted into an appropriate expression system. The gene can be expressed in any number of different recombinant DNA expression systems to generate large amounts of the polypeptide product, which can then be purified and used to vaccinate animals to generate antisera with which further studies may be conducted.

Examples of expression systems known to the skilled practitioner in the art include bacteria such as *E. coli* yeast such as *Pichia pastoris*, baculovirus, and mammalian expression systems such as in Cos or CHO cells. A complete gene can be expressed or, alternatively, fragments of the gene encoding portions of polypeptide can be produced.

In certain broad applications of the invention, the gene sequence encoding the polypeptide is analyzed to detect putative transmembrane sequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially *E. coli* as it leads to the production of insoluble aggregates which are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Antibodies to these sequences may not, therefore, prove useful in in vivo or in situ studies. Deletion of transmembrane-encoding sequences from the genes used for expression can be achieved by standard techniques. For example, fortuitously-placed restriction enzyme sites can be used to excise the desired gene fragment, or PCR-type amplification can be used to amplify only the desired part of the gene.

Computer sequence analysis may be used to determine the location of the predicted major antigenic determinant epitopes of the polypeptide. Software capable of carrying out this analysis is readily available commercially, for example MacVector (IBI, New Haven, Conn.). The software typically uses standard algorithms such as the Kyte/Doolittle or Hopp/Woods methods for locating hydrophilic sequences may be found on the surface of proteins and are, therefore, likely to act as antigenic determinants.

Once this analysis is made, polypeptides may be prepared which contain at least the essential features of the antigenic determinant and which may be employed in the generation of antisera against the polypeptide. Minigenes or gene fusions encoding these determinants may be constructed and inserted into expression vectors by standard methods, for example, using PCR cloning methodology.

The gene or gene fragment encoding a polypeptide may be inserted into an expression vector by standard subcloning techniques. An *E. coli* expression vector may be used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6xHis system add only short sequences, both of which are known to be poorly antigenic and which do not adversely affect folding of the polypeptide to its native conformation. Other fusion systems are designed to produce fusions wherein the fusion partner is easily excised from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The expression system used may also be one driven by the baculovirus polyhedron promoter. The gene encoding the polypeptide may be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant antigen. See Summers et al., A Manual of Methods for Baculovirus Vectors and Insect Cell Culture Procedures, Texas Agricultural Experimental Station; U.S. Pat. No. 4,215,051 (incorporated by reference).

As an alternative to recombinant polypeptides, synthetic peptides corresponding to the antigenic determinants may be prepared. Such peptides are at least six amino acid residues long, and may contain up to approximately 35 residues, which is the approximate upper length limit of automated peptide synthesis machines, such as those available from Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

Amino acid sequence variants of the polypeptide may also be prepared. These may, for instance, be minor sequence variants of the polypeptide which arise due to natural variation within the population or they may be homologues found in other species. They also may be sequences which do not occur naturally but which are sufficiently similar that they function similarly and/or elicit an immune response that cross-reacts with natural forms of the polypeptide. Sequence variants may be prepared by standard methods of site-directed mutagenesis such as those described herein for removing the transmembrane sequence.

Amino acid sequence variants of the polypeptide may be substitutional, insertional or deletion variants. Deletion variants lack one or more residues of the native protein which are not essential for function or immunogenic activity, and are exemplified by the variants lacking a transmembrane sequence. Another common type of deletion variant is one lacking secretory signal sequences or signal sequences directing a protein to bind to a particular part of a cell. An example of the latter sequence is the SH2 domain, which induces protein binding to phosphotyrosine residues.

Substitutional variants typically contain an alternative amino acid at one or more sites within the protein, and may be designed to modulate one or more properties of the polypeptide such as stability against proteolytic cleavage. Substitutions preferably are conservative, that is, one amino acid is replaced with one of similar size and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also may include hybrid proteins containing sequences from other proteins and polypeptides which are homologues of the polypeptide. For example, an insertional variant may include portions of the amino acid sequence of the polypeptide from one species, together with portions of the homologous polypeptide from another species. Other insertional variants may include those in which additional amino acids are introduced within the coding sequence of the polypeptide. These typically are smaller insertions than the fusion proteins described above and are introduced, for example, to disrupt a protease cleavage site.

Major antigenic determinants of the polypeptide may be identified by an empirical approach in which portions of the gene encoding the polypeptide are expressed in a recombinant host, and the resulting proteins tested for their ability to elicit an immune response. For example, PCR may be used to prepare a range of peptides lacking successively longer fragments of the C-terminus of the protein. The immunoprotective activity of each of these peptides then identifies those fragments or domains of the polypeptide which are essential for this activity. Further studies in which only a small number of amino acids are removed at each iteration then allows the location of the antigenic determinants of the polypeptide.

Another method for the preparation of the polypeptides according to the invention is the use of peptide mimetics. Mimetics are peptide-containing molecules which mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within a polypeptide may be predicted by computer-based algorithms as discussed herein. Once the component amino acids of the turn are determined, peptide mimetics may be constructed to achieve a similar spatial orientation of the essential elements of the amino acid side chains.

C. Preparation of Antibodies Specific for Encoded Proteins

1. Expression of Proteins from Cloned cDNAs

The cDNA species specified in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ I) NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45, SEQ ID NO:46 and SEQ ID NO:47 may be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

Both cDNA and genomic sequences are suitable for eukaryotic expression, as the host cell will generally process the genomic transcripts to yield functional mRNA for translation into protein. In addition, it is possible to use partial sequences for generation of antibodies against discrete portions of a gene product, even when the entire sequence of that gene product remains unknown. Computer programs are available to aid in the selection of regions which have potential immunologic significance. For example, software capable of carrying out this analysis is readily available commercially, for example MacVector (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants.

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells which do not contain a recombinantly introduced exogenous DNA segment or gene. Recombinant cells include those having an introduced cDNA or genomic gene, and also include genes positioned adjacent to a heterologous promoter not naturally associated with the particular introduced gene.

To express a recombinant encoded protein or peptide, whether mutant or wild-type, in accordance with the present invention one would prepare an expression vector that comprises one of the claimed isolated nucleic acids under the control of, or operatively linked to, one or more promoters. To bring a coding sequence "under the control of" a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No.31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which may be used by the microbial organism for expression of its own proteins.

In addition, phage vectors containing replicon and control sequences that are compatible with the host microorganism may be used as transforming vectors in connection with these hosts. For example, the phage lambda GEM™-11 may be utilized in making a recombinant phage vector which may be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autograph californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cells lines or host systems may be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells may be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn may be cloned and expanded into cell lines.

A number of selection systems may be used, including but not limited to, the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt- cells, respectively. Also, antimetabolite resistance may be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

It is contemplated that the isolated nucleic acids of the invention may be "overexpressed", i.e., expressed in increased levels relative to its natural expression in human prostate cells, or even relative to the expression of other proteins in the recombinant host cell. Such overexpression may be assessed by a variety of methods, including radio-labelling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural human prostate cells is indicative of overexpression, as is a relative abundance of the specific protein in relation to the other proteins produced by the host cell and, e.g., visible on a gel.

2. Purification of Expressed Proteins

Further aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a prostate cell extract. A purified protein or peptide therefore also refers to a protein or peptide, free from the environment in which it may naturally occur.

Generally, "purified" will refer to a protein or peptide composition which has been subjected to fractionation to remove various other components, and which composition substantially retains its expressed biological activity. Where the term "substantially purified" is used, this will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis;

and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in the most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide may vary, sometimes significantly, with different conditions of SDS/PAGE (Capaldi et al., *Biochem. Biophys. Res. Comm.*, 76:425, 1977). It will therefore be appreciated that under differing electrophoresis conditions, the apparent molecular weights of purified or partially purified expression products may vary.

3. Antibody Generation

For some embodiments, it will be desirable to produce antibodies that bind with high specificity to the polypeptide product(s) of an isolated nucleic acid selected from SEQ ID NO:1, SEQ ID NO:2, SEQ ID NO:3, SEQ ID NO:4, SEQ ID NO:5, SEQ ID NO:10, SEQ ID NO:11, SEQ ID NO:12, SEQ ID NO:13, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45 and SEQ ID NO:46. Means for preparing and characterizing antibodies are well known in the art (See, e.g., Antibodies: A Laboratory Manual, Cold Spring Harbor Laboratory, 1988; incorporated herein by reference).

Methods for generating polyclonal antibodies are well known in the art. Briefly, a polyclonal antibody is prepared by immunizing an animal with an immunogenic composition and collecting antisera from that immunized animal. A wide range of animal species may be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin may also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes maybe used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal may be bled and the serum isolated and stored, and/or the animal may be used to generate MAbs. For production of rabbit polyclonal antibodies, the animal may be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells may operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones may then be propagated indefinitely to provide MAbs. The cell lines may be exploited for MAb production in two basic ways. A sample of the hybridoma may be injected (often into the peritoneal cavity) into a histocompatible animal of the type-that was used to provide the somatic and myeloma cells for the original fusion. The injected animal develops tumors secreting the specific monoclonal antibody produced by the fused cell hybrid. The body fluids of the animal, such as serum or ascites fluid, may then be tapped to provide MAbs in high concentration. The individual cell lines may also be cultured in vitro, where the MAbs are naturally secreted into the culture medium from which they may be readily obtained in high concentrations. MAbs produced by either means may be further purified, if desired, using filtration, centrifugation and various chromatographic methods such as HPLC or affinity chromatography.

Large amounts of the monoclonal antibodies of the present invention may also be obtained by multiplying hybridoma cells in vivo. Cell clones are injected into mammals which are histocompatible with the parent cells, e.g. syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention may be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention may be synthesized using an automated peptide synthesizer.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3H$, $^{125}I$, $^{131}I$ $^{32}P$, $^{35}S$, $^{14}C$, $^{51}Cr$, $^{36}Cl$, $^{57}Co$, $^{58}Co$, $^{59}Fe$, $^{75}Se$, $^{152}Eu$, and $^{99m}Tc$. Radioactively labeled monoclonal antibodies of the present invention are produced according to well-known methods in the art. For instance, monoclonal antibodies may be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$ by ligand exchange process, for example, by reducing pertechnate with stannous solution, chelating the reduced technetium onto a Sephadex column and applying the antibody to this column or by direct labelling techniques, e.g., by incubating pertechnate, a reducing agent such as $SNCl_2$, a buffer solution such as sodium-potassium phthalate solution, and the antibody.

It will be appreciated by those of skill in the art that monoclonal or polyclonal antibodies specific for proteins that are preferentially expressed in metastatic or nonmetastatic human prostate cancer will have utilities in several types of applications. These may include the production of diagnostic kits for use in detecting or diagnosing human prostate cancer. An alternative use would be to link such antibodies to therapeutic agents, such as chemotherapeutic agents, followed by administration to individuals with prostate cancer, thereby selectively targeting the prostate cancer cells for destruction. The skilled practitioner will realize that such uses are within the scope of the present invention.

D. Immunodetection Assays

1. Immunodetection Methods

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides. The steps of various useful immunodetection methods have been described in the scientific literature, such as, e.g., Nakamura et al. (1987).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a prostate disease-marker encoded protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing a prostate cancer-specific antigen, such as a prostate or lymph node tissue section or specimen, a homogenized tissue extract an isolated cell, a cell membrane preparation, separated or purified forms of any of the above protein-containing compositions, or even any biological fluid that comes into contact with prostate tissues, including blood, lymphatic fluid, and even seminal fluid.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of conditions such as prostate cancer and benign prostate hyperplasia. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

In the clinical diagnosis or monitoring of patients with prostate cancer, the detection of an antigen encoded by a prostate cancer marker nucleic acid, or an increase in the levels of such an antigen, in comparison to the levels in a corresponding biological sample from a normal subject is indicative of a patient with prostate cancer. The basis for such diagnostic methods lies, in part, with the finding that the nucleic acid prostate cancer markers identified in the present invention are overexpressed in prostate cancer tissue samples (see Examples below). By extension, it may be inferred that at least some of these markers produce elevated levels of encoded proteins, that may also be used as prostate cancer markers.

Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive. Significant expression may be represented by high levels of antigens in tissues or within body fluids, or alternatively, by a high proportion of cells from within a tissue that each give a positive signal.

2. Immunohistochemistry

The antibodies of the present invention may be used in conjunction with both fresh-frozen and formalin-fixed, paraffin-embedded tissue blocks prepared by immunohistochemistry (IHC). Any IHC method well known in the art may be used such as those described in *Diagnostic Immunopathology*, 2nd edition edited by, Robert B. Colvin, Atul K. Bhan and Robert T. McCluskey. Raven Press, N.Y., 1995, (incorporated herein by reference) and in particular, Chapter 31 of that reference entitled Gynecological and Genitourinary Tumors (ages 579–597), by Debra A Bell, Robert H. Young and Robert E. Scully and references therein.

3. ELISA

As noted, it is contemplated that the encoded proteins or peptides of the invention will find utility as immunogens, e.g., in connection with vaccine development, in immunohistochemistry and in ELISA assays. One evident utility of the encoded antigens and corresponding antibodies is in immunoassays for the detection of prostate disease marker proteins, as needed in diagnosis and prognostic monitoring.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and the like may also be used.

In one exemplary ELISA, antibodies binding to the encoded proteins of the invention are immobilized onto a selected surface exhibiting protein affinity, such as a well in a polystyrene microtiter plate. Then, a test composition suspected of containing the prostate disease marker antigen, such as a clinical sample, is added to the wells. After binding and washing to remove non-specifically bound immunecomplexes, the bound antigen may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the prostate disease marker antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labelled antibodies are added to the wells, allowed to bind to the prostate disease marker protein, and detected by means of their label. The amount of marker antigen in an unknown sample is then determined by mixing the sample with the labelled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human prostate cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand. "Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

4. Use of Antibodies for Radioimaging

The antibodies of this invention will be used to quantify and localize the expression of the encoded marker proteins. The antibody, for example, will be labeled by any one of a variety of methods and used to visualize the localized concentration of the cells producing the encoded protein.

The invention also relates to an in vivo method of imaging a pathological prostate condition using the above described monoclonal antibodies. Specifically, this method involves administering to a subject an imaging-effective amount of a detectably-labeled prostate cancer-specific monoclonal antibody or fragment thereof and a pharmaceutically effective carrier and detecting the binding of the labeled monoclonal antibody to the diseased tissue. The term "in vivo imaging" refers to any method which permits the detection of a labeled monoclonal antibody of the present invention or fragment thereof that specifically binds to a diseased tissue located in the subject's body. A "subject" is a mammal, preferably a human. An "imaging effective amount" means that the amount of the detectably-labeled monoclonal antibody, or fragment thereof administered is sufficient to enable detection of binding of the monoclonal antibody or fragment thereof to the diseased tissue.

A factor to consider in selecting a radionuclide for in vivo diagnosis is that the half-life of a nuclide be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

A radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA). Examples of metallic ions suitable for use in this invention are $^{99m}Tc$, $^{123}I$, $^{131}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

In accordance with this invention, the monoclonal antibody or fragment thereof may be labeled by any of several techniques known to the art. The methods of the present invention may also use paramagnetic isotopes for purposes of in vivo detection. Elements particularly useful in Magnetic Resonance Imaging ("MRI") include $^{157}Gd$, $^{55}Mn$, $^{162}Dy$, $^{52}Cr$, and $^{56}Fe$.

Administration of the labeled antibody may be local or systemic and accomplished intravenously, intraarterially, via the spinal fluid or the like. Administration may also be intradermal or intracavitary, depending upon the body site under examination. After a sufficient time has lapsed for the monoclonal antibody or fragment thereof to bind with the diseased tissue, for example 30 minutes to 48 hours, the area of the subject under investigation is examined by routine imaging techniques such as MRI, SPECT, planar scintillation imaging and emerging imaging techniques, as well. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue may be determined.

It will be apparent to those of skill in the art that a similar approach may be used to radio-image the production of the encoded prostate disease marker proteins in human patients. The present invention provides methods for the in vivo diagnosis of prostate cancer in a patient. Such methods generally comprise administering to a patient an effective amount of a prostate cancer specific antibody, which antibody is conjugated to a marker, such as a radioactive isotope or a spin-labeled molecule, that is detectable by non-invasive methods. The antibody-marker conjugate is allowed sufficient time to come into contact with reactive antigens that be present within the tissues of the patient, and the patient is then exposed to a detection device to identify the detectable marker.

5. Kits

In still further embodiments, the present invention concerns immunodetection kits for use with the immunodetection methods described above. As the encoded proteins or peptides may be employed to detect antibodies and the corresponding antibodies may be employed to detect encoded proteins or peptides, either or both of such components may be provided in the kit. The immunodetection kits will thus comprise, in suitable container means, an encoded protein or peptide, or a first antibody that binds to an encoded protein or peptide, and an immunodetection reagent.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

E. Detection and Quantitation of RNA Species

One embodiment of the instant invention comprises a method for identification of prostate cancer cells in a biological sample by amplifying and detecting nucleic acids corresponding to prostate cancer cell markers. The biological sample may be any tissue or fluid in which prostate cancer cells might be present. Various embodiments include bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, lymph fluid, ascites, serous fluid, pleural effusion, sputum, cerebrospinal fluid, lacrimal fluid, stool or urine.

Nucleic acid used as a template for amplification is isolated from cells contained in the biological sample, according to standard methodologies. (Sambrook et al., 1989) The nucleic acid may be genomic DNA or fractionated or whole cell RNA Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to prostate cancer-specific markers are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with a statistically significant reference group of normal patients and prostate cancer patients. In this way, it is possible to correlate the amount of marker detected with various clinical states.

1. Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

2. Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared which are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art. The most preferred methods of RT-PCR are as described herein in Example 1.

Another method for amplification is the ligase chain reaction ("LCR"), disclosed in European Application No. 320 308, incorporated herein by reference in its entirely. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA which has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention. Walker et al., Proc. Nat'l Acad. Sci. USA 89:392–396 (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences may also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS), including nucleic acid sequence based amplification (NASBA) and 3SR. Kwoh et al., *Proc. Nat'l Acad. Sci. USA* 86:1173 (1989); Gingeras et al., PCT Application WO 88/10315, incorporated herein by reference in their entirety. In NASBA, the nucleic acids may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., European Application No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR-" Frohman, M. A., In: *PCR PROTOCOLS: A GUIDE TO METHODS AND APPLICATIONS*, Academic Press, N.Y. (1990) and Ohara et al., *Proc. Nat'l Acad. Sci. USA,* 86:5673–5677 (1989), each herein incorporated by reference in their entirety.

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., *Genomics* 4:560 (1989), incorporated herein by reference in its entirety.

3. Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook-et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

4. Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and may be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

5. Kit Components

All the essential materials and reagents required for detecting prostate disease markers in a biological sample may be assembled together in a kit. The kit generally will comprise preselected primer pairs for one or more specific markers. For example a kit may include primers to detect RNA markers of normal tissue, BPH tissue, confined tumor tissue or metastatically progressive tumor tissue, or any combination of these. Also included may be enzymes suitable for amplifying nucleic acids including various polymerases (RT, Taq, etc.), deoxynucleotides and buffers to provide the necessary reaction mixture for amplification. Preferred kits may also comprise primers for the detection of a control, non-differentially expressed RNA such as β-actin, for example.

The kits generally will comprise, in suitable means, distinct containers for each individual reagent and enzyme as well as for each marker primer pair. Preferred pairs of primers for amplifying nucleic acids are selected to amplify the sequences designated herein as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45, SEQ ID NO:46 or SEQ ID NO:47.

In certain embodiments, kits will comprise hybridization probes specific for differentially expressed markers. The probes are designed to hybridize to a sequence or a complement of a sequence designated herein as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45, SEQ ID NO:46 or SEQ ID NO:47. Such kits generally will comprise, in suitable means for close confinement, distinct containers for each individual reagent and enzyme as well as for each marker hybridization probe.

F. Use of RNA Fingerprinting to Identify Markers of Prostate Disease

RNA fingerprinting is a means by which RNAs isolated from many different tissues, cell types or treatment groups may be sampled simultaneously to identify RNAs whose relative abundances vary. Two forms of this technology were developed simultaneously and reported in 1992 as RNA fingerprinting by differential display (Liang and Pardee, 1992; Welsh et al., 1992). (See also Liang and Pardee, U.S. Pat. No. 5,262,311, incorporated herein by reference in its entirety.) Both techniques were utilized in the studies described below. Some of the studies described herein were performed similarly to Donahue et al., *J Biol. Chem.* 269: 8604–8609, 1994.

All forms of RNA fingerprinting by PCR are theoretically similar but differ in their primer design and application. The most striking difference between differential display and other methods of RNA fingerprinting is that differential display utilizes anchoring primers that hybridize to the poly A tails of mRNAs. As a consequence, the PCR products amplified in differential display are biased towards the 3' untranslated regions of mRNAs.

The basic technique of differential display has been described in detail (Liang and Pardee, 1992). Total cell RNA is primed for first strand reverse transcription with an anchoring primer composed of oligo dT. The oligo dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR techniques, utilizing the same primers. The resulting DNA fingerprint is analyzed by gel electrophoresis and ethidium bromide staining or autoradiography. A side by side comparison of fingerprints obtained from different cell derived RNAs using the same oligonucleotide primers identifies mRNAs that are differentially expressed.

RNA fingerprinting technology has been demonstrated as being effective in identifying genes that are differentially expressed in cancer (Liang et al., 1992; Wong et al., 1993; Sager et al., 1993; Mok et al., 1994; Watson et al., 1994; Chen et al., 1995; An et al., 1995). The present invention utilizes the RNA fingerprinting technique to identify genes that are differentially expressed in prostate cancer. These studies utilized RNAs isolated from tumor tissues and tumor-derived cell lines that behave as tumors cells with different metastatic potential.

The underlying concept of these studies was that genes that are differentially expressed in cells with different metastatic potentials may be used as indicators of metastatic potential. Since metastasis is a prerequisite for prostate cancer progression to life threatening pathologies, indicators of metastatic potential are likely to be indicators of pathological potential.

G. Design and Theoretical Considerations for Relative Quantitative RT-PCR

Reverse transcription (RT) of RNA to cDNA followed by relative quantitative PCR (RT-PCR) may be used to determine the relative concentrations of specific mRNA species in a series of total cell RNAs isolated from normal, benign and cancerous prostate tissues. By determining that the concentration of a specific mRNA species varies, it is shown that the gene encoding the specific mRNA species is differentially expressed. This technique may be used to confirm that mRNA transcripts shown to be differentially regulated by RNA fingerprinting are differentially expressed in prostate cancer progression.

In PCR, the number of molecules of the amplified target DNA increase by a factor approaching two with every cycle of the reaction until some reagent becomes limiting. Thereafter, the rate of amplification becomes increasingly diminished until there is not an increase in the amplified target between cycles. If one plots a graph on which the cycle number is on the X axis and the log of the concentration of the amplified target DNA is on the Y axis, one observes that a curved line of characteristic shape is formed by connecting the plotted points. Beginning with the first cycle, the slope of the line is positive and constant. This is said to be the linear portion of the curve. After some reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR is directly proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is only true in the linear range portion of the PCR reaction.

The final concentration of the target DNA in the plateau portion of the curve is determined by the availability of reagents in the reaction mix and is independent of the original concentration of target DNA Therefore, the one condition that must be met before the relative abundances of an mRNA species may be determined by RT-PCR for a collection of RNA populations is that the concentrations of the amplified PCR products must be sampled when the PCR reactions are in the linear portion of their curves.

A second condition that must be met for an RT-PCR study to successfully determine the relative abundances of a particular mRNA species is that relative concentrations of the amplifiable cDNAs must be normalized to some independent standard. The goal of an RT-PCR study is to determine the abundance of a particular mRNA species relative to the average abundance of all mRNA species in the sample. In the studies described below, mRNAs for β-actin, asparagine synthetase and lipocortin II were used as external and internal standards to which the relative abundance of other mRNAs are compared.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons may be made between RNA samples.

The discussion above describes the theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies described below were performed using a more conventional relative quantitative RT-PCR with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This is very important since this assay measures absolute mRNA abundance. Absolute mRNA abundance may be used as a measure of differential gene expression only in normalized samples. While empirical determination of the linear range of the amplification curve and normalization of cDNA preparations are tedious and time consuming processes, the resulting RT-PCR assays may be superior to those derived from the relative quantitative RT-PCR with an internal standard.

One reason for this is that without the internal standard/competitor, all of the reagents may be converted into a single PCR product in the linear range of the amplification curve, increasing the sensitivity of the assay. Another reason is that with only one PCR product, display of the product on an electrophoretic gel or some other display method becomes less complex, has less background and is easier to interpret.

H. Diagnosis and Prognosis of Human Cancer

In certain embodiments, the present invention allows the diagnosis and prognosis of human prostate cancer by screening for marker nucleic acids. The field of cancer diagnosis and prognosis is still uncertain. Various markers have been proposed to be correlated with metastasis and malignancy. They may be classified generally as cytologic, protein or nucleic acid markers.

Cytologic markers include such things as "nuclear roundedness" (Diamond et al., 1982) and cell ploidy. Protein markers include prostate specific antigen (PSA) and CA125. Nucleic acid markers have included amplification of Her2/neu, point mutations in the p53 or ras genes, and changes in the sizes of triplet repeat segments of particular chromosomes.

All of these markers exhibit certain drawbacks, associated with false positives and false negatives. A false positive result occurs when an individual without malignant cancer exhibits the presence of a "cancer marker". For example, elevated serum PSA has been associated with prostate carcinoma. However, it also occurs in some individuals with non-malignant, benign hyperplasia of the prostate. A false negative result occurs when an individual actually has cancer, but the test fails to show the presence of a specific marker. The incidence of false negatives varies for each marker, and frequently also by tissue type. For example, ras point mutations have been reported to range from a high of 95 percent in pancreatic cancer to a low of zero percent in some gynecologic cancers.

Additional problems arise when a marker is present only within the transformed cell itself. Ras point mutations may only be detected within the mutant cell, and are apparently not present in, for example, the blood serum or urine of individuals with ras-activated carcinomas. This means that, in order to detect a malignant tumor, one must take a sample of the tumor itself, or its metastatic cells. Since the object of cancer detection is to identify and treat tumors before they metastasize, essentially one must first identify and sample a tumor before the presence of the cancer marker can be detected.

Finally, specific problems occur with markers that are present in normal cells but absent in cancer cells. Most tumor samples will contain mixed populations of both normal and transformed cells. If one is searching for a marker that is present in normal cells, but occurs at reduced levels in transformed cells, the "background" signal from the normal cells in the sample may mask the presence of transformed cells.

The ideal cancer marker would be one that is present in malignant cancers, and either missing or else expressed at significantly lower levels in benign tumors and normal cells. Further, since any single marker would typically be present only in some proportion of malignant cancers, it is better to have a number of such markers for each cancer type. The present invention addresses this need for prostate cancer by identifying several new nucleic acid markers that are expressed at much higher levels in malignant prostate carcinoma than in benign or normal prostate. In particular, the results for markers UC Band #28 (SEQ ID NO:3) and UC Band #33 (SEQ ID NO:5), discussed in Examples 2 and 4 below, are quite promising in that these markers are apparently only overexpressed in malignant tumors and are present at very low levels in benign or normal prostate. Further, these markers are significantly elevated in a high percentage of human prostate cancers examined to date.

It is anticipated that in clinical applications, human tissue samples will be screened for the presence of the markers of prostate disease identified herein. Such samples could consist of needle biopsy cores, surgical resection samples, lymph node tissue, or serum. In certain embodiments, nucleic acids would be extracted from these samples and amplified as described above. Some embodiments would utilize kits containing pre-selected primer pairs or hybridization probes. The amplified nucleic acids would be tested for the markers by, for example, gel electrophoresis and ethidium bromide staining, or Southern blotting, or a solid-phase detection means as described above. These methods are well known within the art. The levels of selected markers detected would be compared with statistically valid groups of metastatic, non-metastatic malignant, benign or normal prostate samples. The diagnosis and prognosis of the individual patient would be determined by comparison with such groups.

Another embodiment of the present invention involves application of RT-PCR techniques to detect circulating prostate cancer cells (i.e., those that have already metastasized), using probes and primers selected from sequences or their complements designated herein as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45, SEQ ID NO:46 or SEQ ID NO:47. Similar techniques have been described in PCT Patent Application No. WO 94/10343, incorporated herein by reference.

In this embodiment, metastatic prostate cancer cells are detected in hematopoietic samples by amplification of prostate cancer-specific nucleic acid sequences. Samples taken from blood or lymph nodes are treated as described below to purify total cell RNA. The isolated RNA is reverse transcribed using a reverse transcriptase and primers selected to bind under high stringency conditions to a nucleic acid sequence to the sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:45, SEQ ID NO:46 or SEQ ID NO:47. Following reverse transcription, the resulting cDNAs are amplified using standard PCR techniques (described below) and a thermostable DNA polymerase.

The presence of amplification products corresponding to prostate cancer-marker nucleic acids may be detected by several alternative means. In one embodiment, the amplification product may be detected by gel electrophoresis and ethidium bromide staining. Alternatively, following the gel electrophoresis step the amplification product may be detected by standard Southern blotting techniques, using an hybridization probe selected to bind specifically to a prostate cancer-marker nucleic acid sequence. Probe hybridization may in turn be detected by a standard labelling means, for example, by incorporation of [$^{32}$P]-nucleotides followed by autoradiography. The amplification products may alternatively be detected using a solid phase detection system as described above, utilizing a prostate cancer-marker specific hybridization probe and an appropriate labelling means. The presence of prostate cancer-marker nucleic acids in blood or lymph node samples may be taken as indicative of a patient with metastatic prostate cancer.

I. Targeted Inhibition of Prostate Cancer Markers

In principal, the prostate cancer markers identified in the present invention may serve as targets for therapeutic intervention in prostate cancer. One of the identified genes, cyclin A, has been described as a target for a number of agents that inhibit tumor cell growth by promoting differentiation or inhibiting cell division. For example, L-tyrosine has been reported to promote increased melanogenesis and replicative senescence in the B16 melanoma cell line, correlated with a decrease in cyclin A activity. (Rieber & Rieber, 1994) Suramin is an antitumor agent that reduces the expression of cyclin A in the DU-145 prostate carcinoma cell line. (Qiao et al., 1994) Rapamycin inhibits cell proliferation in the YAC-1 T cell lymphoma and also inhibits cyclin A mRNA production. (Dumont et al., 1994) It is not clear if these inhibitors are acting directly on cyclin A, or somewhere upstream in a signal transduction/phosphorylation cascade pathway. However, inhibitors of cyclin A should inhibit cell proliferation and decrease tumor growth. Such inhibitors may have utility as therapeutic agents for the treatment of prostate cancer.

Inhibitors could also potentially be designed for the previously unreported prostate cancer markers identified in the present invention. This is complicated by the fact that no specific function has been identified for most of these gene products, and no data is available on their three-dimensional structures.

Identification of protein function may be extrapolated, in some cases, from the primary sequence data, provided that sequence homology exists between the unknown protein and a protein of similar sequence and known function. Proteins tend to occur in large families of relatively similar sequence and function. For example, a number of the serine proteases, like trypsin and chymotrypsin, have extensive sequence homologies and relatively similar three-dimensional structures. Other general categories of homologous proteins include different classes of transcriptional factors, membrane receptor proteins, tyrosine kinases, GTP-binding proteins, etc. The putative amino acid sequences encoded by the prostate cancer marker nucleic acids of the present invention may be cross-checked for sequence homologies versus the protein sequence database of the National Biomedical Research Fund. Homology searches are standard techniques for the skilled practitioner.

Even three-dimensional structure may be inferred from the primary sequence data of the encoded proteins. Again, if homologies exist between the encoded amino acid sequences and other proteins of known structure, then a model for the structure of the encoded protein may be designed, based upon the structure of the known protein. An example of this type of approach was reported by Ribas de Pouplana and Fothergill-Gilmore (Biochemistry 33: 7047–7055, 1994). These authors developed a detailed three-dimensional model for the structure of Drosophila alcohol dehydrogenase, based in part upon sequence homology with the known structure of 3α, 20-β-hydroxysteroid dehydrogenase. Once a three-dimensional model is available, inhibitors may be designed by standard computer modeling techniques. This area has been recently reviewed by Sun and Cohen (Gene 137: 127–132, 1993), herein incorporated by reference.

Antisense constructs

The term "antisense" is intended to refer to polynucleotide molecules complementary to a portion of a RNA marker of prostate disease as defined herein. "Complementary" polynucleotides are those which are capable of base-pairing according to the standard Watson-Crick complementarity rules. That is, the larger purines will base pair with the smaller pyrmidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal including a human subject.

The intracellular concentration of monovalent cation is approximately 160 mM (10 mM Na$^+$; 150 mM K$^+$). The intracellular concentration of divalent cation is approximately 20 mM (18 mM Mg$^+$; 2 mM Ca$^{++}$). The intracellular protein concentration, which would serve to decrease the volume of hybridization and, therefore, increase the effective concentration of nucleic acid species, is 150 mg/ml. Constructs can be tested in vitro under conditions that mimic these in vivo conditions.

Antisense constructs may be designed to bind to the promoter and other control regions, exons, introns or even exon-intron boundaries of a gene. It is contemplated that the most effective antisense constructs for the present invention will include regions complementary to the mRNA start site, or to those sequences identified herein as prostate disease markers. One can readily test such constructs simply by testing the constructs in vitro to determine whether levels of the target protein are affected. Similarly, detrimental non-specific inhibition of protein synthesis also can be measured by determining target cell viability in vitro.

As used herein, the terms "complementary" or "antisense" mean polynucleotides that are substantially complementary over their entire length and have very few base mismatches. For example, sequences of fifteen bases in length may be termed complementary when they have a complementary nucleotide at thirteen or fourteen nucleotides out of fifteen. Naturally, sequences which are "completely complementary" will be sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

As stated above, although the antisense sequences may be full length cDNA copies, or large fragments thereof they also may be shorter fragments, or "oligonucleotides," defined herein as polynucleotides of 50 or less bases. Although shorter oligomers (8–20) are easier to make and increase in vivo accessibility, numerous other factors are involved in determining the specificity of base-pairing. For example, both binding affinity and sequence specificity of an oligonucleotide to its complementary target increase with increasing length. It is contemplated that oligonucleotides of 8, 9, 10, 11, 12, 13, 14, 15, 16, 17, 18, 19, 20, 25, 30, 35, 40, 45, 50 or 100 base pairs will be used. While all or part of the gene sequence may be employed in the context of antisense construction, statistically, any sequence of 14 bases long should occur only once in the human genome and, therefore, suffice to specify a unique target sequence.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" is refers to an RNA-based enzyme capable of targeting and cleaving particular base sequences in both DNA and RNA Ribozymes can either be targeted directly to cells, in the form of RNA oligonucleotides incorporating ribozyme sequences, or introduced into the cell as an expression vector encoding the desired ribozymal RNA. Ribozymes may be used and applied in much the same way as described for antisense polynucleotide. Ribozyme sequences also may be modified in much the same way as described for antisense polynucleotide. For example, one could incorporate non-Watson-Crick bases, or make mixed RNA/DNA oligonucleotides, or modify the phosphodiester backbone, or modify the 2'-hydroxy in the ribose sugar group of the RNA.

Alternatively, the antisense oligo- and polynucleotides according to the present invention may be provided as RNA via transcription from expression constructs that carry nucleic acids encoding the oligo- or polynucleotides. Throughout this application, the term "expression construct" is meant to include any type of genetic construct containing a nucleic acid encoding an antisense product in which part or all of the nucleic acid sequence is capable of being transcribed. Typical expression vectors include bacterial plasmids or phage, such as any of the pUC or Bluescript™ plasmid series or, as discussed further below, viral vectors adapted for use in eukaryotic cells.

In preferred embodiments, the nucleic acid encodes an antisense oligo- or polynucleotide under transcriptional control of a promoter. A "promoter" refers to a DNA sequence recognized by the synthetic machinery of the cell or introduced synthetic machinery, required to initiate the specific transcription of a gene. The phrase "under transcriptional control" means that the promoter is in the correct location and orientation in relation to the nucleic acid to control RNA polymerase initiation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding the inhibitory peptide is not believed to be important, so long as it is capable of expressing the peptide in the targeted cell. Thus, where a human cell is targeted, it is preferable to position the nucleic acid coding the inhibitory peptide adjacent to and under the control of a promoter that is active in the human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of various proteins. The use of other viral or mammalian cellular or bacterial phage promoters which are well-known in the art to achieve expression of peptides according to the present invention is contemplated as well, provided that the levels of expression are sufficient for a given purpose.

By employing a promoter with well-known properties, the level and pattern of expression of an antisense oligo- or polynucleotide can be optimized. Further, selection of a promoter that is regulated in response to specific physiologic signals can permit inducible expression of an inhibitory protein. For example, a nucleic acid under control of the human PAI-1 promoter results in expression inducible by tumor necrosis factor. Additionally any promoter/enhancer combination (as per the Eukaryotic Promoter Data Base EPDB) also could be used to drive expression of a nucleic acid according to the present invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

In certain embodiments of the invention, the delivery of a nucleic acid in a cell may be identified in vitro or in vivo by including a marker in the expression construct. The marker would result in an identifiable change to the transfected cell permitting easy identification of expression. Enzymes such as herpes simplex virus thymidine kinase (tk) (eukaryotic) or chloramphenicol acetyltransferase (CAT) (prokaryotic) may be employed.

One also may include a polyadenylation signal to effect proper polyadenylation of the transcript. The nature of the polyadenylation signal is not believed to be crucial to the successful practice of the invention, and any such sequence may be employed. For example, the SV40, β-globin or adenovirus polyadenylation signal may be employed. Also contemplated as an element of the expression cassette is a terminator. These elements can serve to enhance message levels and to minimize read through from the cassette into other sequences.

Liposomal formulations

In certain broad embodiments of the invention, the antisense oligo- or polynucleotides and/or expression vectors may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are cationic lipid-nucleic acid complexes, such as lipofectamine-nucleic acid complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacterial promoter is employed in the DNA construct, it also will be desirable to include within the liposome an appropriate bacterial polymerase.

"Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform, chloroform/methanol or t-butanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules will form a bilayer, known as a lamella, of the arrangement XY–YX.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be reconstituted in a solution of nucleic acid and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentration and stored at 4° C. until use.

In a preferred embodiment, the lipid dioleoylphosphatidylchoine is employed. Nuclease-resistant oligonucleotides were mixed with lipids in the presence of excess t-butanol. The mixture was vortexed before being frozen in an acetone/dry ice bath. The frozen mixture was lyophilized and hydrated with Hepes-buffered saline (1 mM Hepes, 10 mM NaCl, pH 7.5) overnight, and then the liposomes were sonicated in a bath type sonicator for 10 to 15 min. The size of the liposomal-oligonucleotides typically ranged between 200–300 nm in diameter as determined by the submicron particle sizer autodilute model 370 (Nicomp, Santa Barbara, Calif.).

Alternative Delivery Systems

Adenoviruses: Human adenoviruses are double-stranded DNA tumor viruses with genome sizes of approximate 36 kB (Tooze, 1981). As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

As only a small portion of the viral genome appears to be required in cis (Tooze, 1981), adenovirus-derived vectors offer excellent potential for the substitution of large DNA fragments when used in connection with cell lines such as 293 cells. Ad5-transformed human embryonic kidney cell lines (Graham, et al., 1977) have been developed to provide the essential viral proteins in trans.

Particular advantages of an adenovirus system for delivering foreign proteins to a cell include (i) the ability to substitute relatively large pieces of viral DNA by foreign DNA, (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kB of foreign DNA and can be grown to high titers in 293 cells (Stratford-Perricaudet and Perricaudet, 1991). Surprisingly persistent expression of transgenes following adenoviral infection has also been reported.

Other Viral Vectors as Expression Constructs. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1998; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-viral Methods. Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), lipofectamine-DNA complexes, and receptor-mediated transfection (Wu and Wu, 1987; Wu and Wu, 1988). Some of these techniques may be successfully adapted for in vivo or ex vivo use.

In one embodiment of the invention, the expression construct may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding an antisense prostate marker construct may also be transferred in a similar manner in vivo.

Pharmaceutical Compositions and Routes of Administration

Where clinical application of liposomes containing antisense oligo- or polynucleotides or expression vectors is undertaken, it will be necessary to prepare the liposome complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention comprise an effective amount of the antisense expression vector encapsulated in a liposome as discussed above, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxyvropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration and the potency, stability and toxicity of the particular therapeutic substance. For the instant application, it is envisioned that the amount of therapeutic composition comprising a unit dose will range from about 5–30 mg of polynucleotide.

The following examples are included to demonstrate preferred embodiments of the invention. It should be appreciated by those of skill in the art that the techniques disclosed in the examples which follow represent techniques discovered by the inventors to function well in the practice of the invention, and thus may be considered to constitute preferred modes for its practice. However, those of skill in the art should, in light of the present disclosure, appreciate that many changes may be made in the particular embodiments which are disclosed and still obtain a like or similar result without departing from the spirit and scope of the invention.

J. Materials and Methods

1. Application of RNA fingerprinting to discover biomarkers for prostate cancers RNA fingerprinting (according to Liang and Pardee, 1992; Welsh et al., 1992; Liang and Pardee, 1993) was applied to nucleic acids isolated from primary human prostate tumors or from prostate tumor derived cell lines that behave as tumor cells with different metastatic potential. The human prostate cancer cell lines examined in these studies were LnCaP, PC-3(p), PC-3(ml), and DU-145. These cell lines vary in their metastatic potentials. LnCaP is only slightly metastatic while the other three cell lines are very aggressive and highly metastatic. The primary human prostate tumors used were of varying degrees of malignancy.

The cell lines were propagated in RPMI-1640 (GIBCO-BRL, Inc.) supplemented with 10% fetal bovine serum, 5 units/ml penicillin G, 5 μg/ml streptomycin, and Fungizone according to the supplier's directions. All antibiotics were purchased from GIBCO-BRL, Inc. Cells were harvested in late log phase of growth. RNA was isolated by the guanidinium thiocyanate method (Chomczynski and Sacchi 1987). RNA was also isolated from solid prostate tumors by guanidinium thiocyanate extraction (Chomczynski and Sacchi, 1987), after the tumors were frozen and ground to a powder in liquid nitrogen.

After RNA isolation, the nucleic acids were precipitated with ethanol. The precipitates were pelleted by centrifugation and redissolved in water. The redissolved nucleic acids were then digested with RNase-free DNase I (Boehringer Mannheim, Inc.) following the manufacturer's instructions, followed by organic extraction with phenol:chloroform:isoamyl alcohol (25:24:1) and reprecipitation with ethanol.

The DNase I treated RNA was then pelleted by centrifugation and redissolved in water. The purity and concentration of the RNA in solution was estimated by determining optical density at wave lengths of 260 nm and 280 nm (Sambrook et al., 1989). A small aliquot of the RNA was also separated by gel electrophoresis in a 3% formaldehyde gel with MOPS buffer (Sambrook et al., 1989) to confirm the estimation of concentration and to determine if the ribosomal RNAs were intact. This RNA, hereafter referred to as total cell RNA, was used in the studies described below.

2. Methods Utilized in the Differential Display Technique

There were two kinds of RNA fingerprinting studies performed with the total cell RNA. The first of these kinds of studies followed the differential display protocol of Liang and Pardee (1992) except that it was modified by using 5' biotinylated primers for nonisotopic PCR product detection.

In these studies, 0.2 μg of total cell RNA was primed for reverse transcription with an anchoring primer composed of oligo dT, then two arbitrarily chosen nucleotides. The anchoring primers used in these studies were further modified to be biotinylated at the 5' end.

Reverse transcription was performed with 200 units of MMLV (Moloney Murine Leukemia Virus) reverse transcriptase (GIBCO/BRL) in the presence of 50 mM Tris-HCl (pH 8.3), 75 mM KCl, 3 mM $MgCl_2$, 10 mM DTT, 500 μM dNTP, 1 μM biotinylated anchored primer and 1 U/μl RNase inhibitor. The reaction mixture was incubated at room temperature for 10 minutes, then at 37° C. for 50 minutes. After reverse transcription the enzyme was denatured by heating to 65° C. for 10 minutes.

One tenth of the resulting reverse transcription reactions were then amplified by PCR using the same anchoring primer as was used in the reverse transcription step and a second oligonucleotide of arbitrarily chosen sequences. The PCR reaction contained 10 mM Tris-HCl (pH 8.3), 50 mM KCl, 20 μM dNTP, 1.5 μM $MgCl_2$, 200 nM arbitrary decamer, 1 μM biotinylated anchored primer, and 1 unit of Taq DNA polymerase (Boehringer Mannheim) in a 40 μl volume. The amplification was performed in a thermal cycler (MJ Research) for 30 cycles with denaturing at 94° C. for 30 sec, annealing at 40° C. for 2 min. and extending at 72° C. for 30 sec.

The PCR products were then separated on a 6% TBE-urea sequencing gel (Sambrook et al., 1989) and detected by chemiluminescent reaction using the Seq-Lights™ detection system (Tropix, Inc). Differentially appearing PCR products were excised from the gels, reamplified using the same primers used in the original amplification, and cloned using the TA cloning strategy (Invitrogen, Inc. and Promega, Inc.).

3. Methods Utilized in the RNA Fingerprinting Technique

The second type of RNA fingerprinting studies performed more closely resembled the protocol of Welsh et al. (1992). This approach used a variation of the above as modified by the use of agarose gels and non-isotopic detection of bands by ethidium bromide staining (An et al., 1995). Total RNAs were isolated from the frozen prostate tissues or cultured cells as described (Chomczynski & Sacchi, 1987). Ten micrograms of total cellular RNAs were treated with 5 units of RNAse-free DNAse I (GIBCO/BRL) in 20 mM Tris-HCl (pH 8.4), 50 mM KCl, 2 mM $MgCl_2$, and 20 units of RNAse inhibitor (Boehringer Mannheim). After extraction with phenol/chloroform and ethanol precipitation, the RNAs were redissolved in DEPC-treated water.

Two μg of each total cell RNA sample was reverse transcribed into cDNA using randomly selected hexamer primers and MMLV reverse transcriptase (GIBCO/BRL). PCR was performed using one or two arbitrarily chosen oligonucleotide primers (10–12mers). PCR conditions were: 10 mM Tris-HCl (pH 8.3), 50 mM KCl, 1.5 mM $MgCl_2$, 50 μM dNTPs, 0.2 μM of primer(s), 1 unit of Taq DNA polymerase (GIBCO/BRL) in a final volume of 20 μl. The amplification parameters included 35 cycles of reaction with 30 sec denaturing at 94° C., 90 sec annealing at 40° C., and 60 sec extension at 72° C. A final extension at 72° C. was performed for 15 min. The resulting PCR products were resolved into a fingerprint by size separation by electrophoresis through 2% agarose gels in TBE buffer (Sambrook et al., 1989). The fingerprints were visualized by staining with ethidium bromide. No reamplification was performed.

Differentially appearing PCR products, that might represent differentially expressed genes, were excised from the gel with a razor blade, purified from the agarose using the Geneclean kit (Bio 101, Inc.), eluted in water and cloned directly into plasmid vectors using the TA cloning strategy (Invitrogen, Inc., and Promega, Inc.). These products were not reamplified after the initial PCR fingerprinting protocol.

4. Confirmation of Differential Expression by Relative Quantitative RT-PCR: Protocols for RT-PCR a. Reverse transcription Five μg of total cell RNA from each tissue sample was reverse transcribed into cDNA. Reverse transcription was performed with 400 units of MMLV reverse transcriptase (GIBCO/BRL) in the presence of 50 mM Tris-HCl (pH 8.3), 75 mM KCl 3 mM MgCl$_2$, 10 mM DTT, 500 μM dNTP, 50 ng random hexamers per microgram of RNA, and 1 U/μl RNase inhibitor. The reaction volume was 60 μl. The reaction mixture was incubated at room temperature for 10 minutes, then at 37° C. for 50 minutes. After reverse transcription the enzyme was denatured by heating to 65° C. for 10 minutes. After heat denaturation the samples were diluted with water to a final volume of 300 μl.

RT-PCR was utilized to examine mRNAs for differential expression. The sequences of oligonucleotides used as primers to direct the amplification of the various cDNA fragments are presented in Table 2.

b. Relative Quantitative RT-PCR With an Internal Standard

The concentrations of the original total cell RNAs were determined by measurement of OD$_{260/280}$ (Sambrook et al., 1989) and confirmed by examination of ribosomal RNAs on ethidium bromide stained agarose gels. It is required that all quantitative PCR reactions be normalized for equal amounts of amplifiable cDNA after the reverse transcription is completed. One solution to this is to terminate the reactions by driving the PCR reactions into plateau phase. This approach was utilized in some studies because it is quick and efficient. Lipocortin II was used as the internal standard or competitor. These PCRs were set up as:

Reagents: 200 μM each dNTP, 200 nM each oligonucleotide primer, 1×PCR buffer (Boehringer Mannheim including 1.5 mM MgCl$_2$), 3 μl diluted cDNA, and 2.5 units of Taq DNA polymerase/100 μl of reaction volume.

Cycling parameters: 30 cycles of 94° C. for 1 min; 55° C. for 1 min; and 72° C. for two min. Thermocyclers were either the MJ research thermocycler or the Stratagene Robocycler.

c. Relative Quantitative RT-PCR with an External Stand

There are three potential difficulties with the relative quantitative RT-PCR strategy described above. First, the internal standard must be roughly 4–10 times more abundant that the target for this strategy to normalize the samples. Second, because most of the PCR products are templated from the more abundant internal standard, the assay is less than optimally sensitive. Third, the internal standard must be truly unvarying. The result is that while the strategy described above is fast, convenient and applicable to samples of varying quality, it lacks sensitivity to modest changes in abundances.

To address these issues, a normalization was performed using both the β-actin and asparagine synthetase mRNAs as external standards. These PCR reactions were performed with sufficient cycles to observe the products in the linear range of their amplification curves. Photographic negatives of gels of ethidium bromide stained PCR products were produced for each study. These negatives were scanned and quantified using a BioRad densitometer. The quantified data was then normalized for variations in the staring concentrations of amplifiable cDNA by comparing the quantified data from each study with that derived from a similar study which amplified a cDNA fragment copied from the β-actin mRNA. Quantified data that had been normalized to beta actin were converted into bar graph representations.

K. EXAMPLES

Example 1

Relative Quantitative Reverse Transcriptase-Polymerase Chain Reaction-A method to evaluate novel genes (ESTs) as diagnostic biomarkers.

The reverse transcription-polymerase chain reaction (RT-PCR) protocols described in the following example were developed as a means to determine the relative abundances of mRNA species that are expressed in various tissues, organs and cells. The protocols used to meet this need must be robust, reproducible, relatively quantitative, sensitive, conservative in its use of resources, rapid and have a high throughput rate. Relative quantitative RT-PCR has the technical features that, in theory, meet all of these criteria. In practice there are six important barriers to implementing an RT-PCR based assay that compares the relative abundances of mRNA species. The protocol described herein addresses each of these six barriers and has permitted the realization of the potential of RT-PCR for this application. Although the present example is drawn to the identification and confirmation of differential expression in various physiological states in prostate tissue, the methods described herein may be applied to any type of tissue to provide a sensitive method of identifying differential expression.

The large majority of the candidate genes examined by this method are partial cDNA fragments that have been identified by RNA fingerprinting methodologies. This necessitated development of a relatively quantitative approach to independently confirm the differential expression of the mRNAs from which these partial cDNA fragments were derived. The key objective of the described screening protocol is the assessment of changes in the relative abundances of mRNA.

The gene discovery program described in the present disclosure is focused on analysis of human tissue and confirmation must be performed on the same biological material. Access to human tissue for isolation of RNA is limited. This limitation is especially problematic in Northern blots, the traditional means to determine differential gene expression. Northern blots typically consume roughly 20 μg of RNA per examined tissue per gene identified. This means that for the average size of tissue sample available, only 1–5 Northern blots can be performed before all of the RNA from a tissue sample is completely consumed. Clearly Northern blots are seriously limited for primary confirmation of discovered genes and consume extremely valuable biological resources required for gene discovery and characterization.

Because of such limitations on the amount of available tissue, and because of the need for high throughput and rapid turnaround of results, a two tiered assay protocol has been developed that is technologically grounded on reverse transcription (RT) of RNA into cDNA followed by amplification of specific cDNA sequences by polymerase chain reaction (PCR). This coupling of techniques is frequently referred to as RT-PCR.

One advantage of RT-PCR is that it consumes relatively small quantities of RNA. With 20 μg of RNA per examined sample, the amount of RNA required to perform a single Northern blot experiment, 50–200 RT-PCR assays can be performed with up to four data points per assay. Another advantage is a high throughput, eight independent experiments which examine eight different mRNA species for differential expression can be performed simultaneously in a single PCR machine with 96 wells. A single individual skilled in this technique can thereby examine and evaluate eight genes per day without significant time constraints. By comparison, even if RNA of sufficient quality and quantity were available to do this number of Northern blots, a similarly skilled individual performing Northern blots would be hard pressed to examine and evaluate eight genes per week. In addition to the lower throughput rate of Northern blots, eight Northern blots per week would require the consumption of about 400 μCi of $^{32}$P per week. While not dangerous to use in the hands of a skilled individual, $^{32}P$ is certainly inconvenient to use. RT-PCR avoids the use of radioactive materials.

An additional advantage of RT-PCR over Northern blots as a technological platform for evaluating the relative expression of mRNA species is that RT-PCR is much less sensitive to differences in quality of the RNA being examined. The human tissues described herein were removed from patients for treatment purposes and were only incidentally saved for further studies. Hence the RNA, an extremely labile molecule, is expected to be at least partially degraded. Because the RNA is separated by size on a gel in the Northern blot assay, partially degraded RNA appears as a smear, rather than discrete bands. By contrast, RT-PCR amplifies only a section or domain of an RNA molecule, and as long as that portion is intact, the size or degradation state of the entire molecule is irrelevant. As a result, RNAs that are identical except that they vary by degree of partial degradation will give much more variable signals in a Northern blot than they will in an RT-PCR When samples are of variable quality, as is often the case in human studies, the relative sensitivities of the techniques to variation in sample quality is an important consideration.

In the practice of this method, total cell RNA is first converted into cDNA using reverse transcriptase primed with random hexamers. This protocol results in a cDNA population in which each RNA has contributed according to its relative proportion in original total cell RNA. If two RNA species differ by ten fold in their original relative abundances in the total cell RNA, then the cDNA derived from these two RNAs will also differ by ten fold in their relative abundances in the resulting population of cDNA. This is a conservation of relative proportionality in the conversion of RNA to cDNA.

Another consideration is the relative rates of amplification of a targeted cDNA by PCR. In theory, the amount of an amplified product synthesized by PCR will be equal to $M(E^C)$. Where M is the mass of the targeted cDNA molecules before the beginning of PCR and C is the number of PCR cycle performed. E is an efficiency of amplification factor. This factor is complex and varies between 1 and 2. The important consideration in this assay is that over most of a PCR amplification, E will be nearly constant and nearly equal to 2. In PCR reactions that are identical in every way except the cDNAs being used as templates are derived from different total cell RNAs, then E will have the same value in each reaction. If a cDNA target has an initial mass of $M_1$ in one PCR reaction and a mass of $M_2$ in another PCR reaction and if E has the same value in each reaction, then after C cycles of PCR there will be a mass of $M_1(E^C)$ of the amplified target in the first reaction and a mass of $M_2(E^C)$ of the amplified target in the second reaction. The ratios of these masses is unaltered by PCR amplification. That is $M1/M2=[M_1(E^C)]/M_2(E^C)$. Hence, there is a conservation of relative proportionality of amplified products during PCR. Since both reverse transcription and PCR can be performed in such a way as to conserve proportionality, it is possible to compare the relative abundance of an mRNA species in two or more total cell RNA populations by first converting the RNA to cDNA and then amplifying a fragment of the cDNA derived from the specific mRNA by PCR. The ratio of the amplified masses of the targeted cDNA is very close to or identical to the ratios of the mRNAs in the original total cell RNA populations.

Six major challenges or barriers to be overcome in order to best use RT-PCR to quantitate the relative abundances of RNA are as follows:

1.) Degradation of RNA must be minimized during RNA preparation.
2.) Genomic DNA must be eliminated.
3.) RNA must be free of contaminants that might interfere with reverse transcription.
4.) The efficiency of RT is variable. cDNAs, not RNA, must be normalized for equal concentrations of amplifiable cDNA.
5.) Limited linear range requires multiple sampling points in any amplification curve.
6.) Tube to tube variability in PCR It is the development of techniques to overcome these barriers and to provide a sensitive and accurate method of quantitative RT-PCR that is applicable to any tissue type or physiological state that is a part of the present invention.

The first three barriers to successful RT-PCR are all related to the quality of the RNA used in this assay. The protocols described in this section address the first two barriers as described in the last section. These are the requirements that degradation of RNA must be minimized during RNA preparation and that genomic DNA must be eliminated from the RNA.

Two preferred methods for RNA isolation are the guanididium thiocyanate method, which is well known in the art, and kits for RNA isolation manufactured by Qiagen, Inc. (Chatworth, Calif.), with the kits being the most preferred for convenience. Four protocols are performed on the RNA isolated by either method (or any method) before the RNA is be used in RT-PCR.

The first of these four protocols is digestion of the RNAs with DNaseI to remove all genomic DNA that was co-isolated with the total cell RNA. Prior to DNaseI digestion, the RNA is in a particulate suspension in 70% ethanol. Approximately 50 μg of RNA (as determined by $OD_{260/280}$) is removed from the suspension and precipitated. This RNA is resuspended in DEPC treated sterile water. To this is added 10× DNaseI buffer (200 mM Tris-HCl; pH 8.4, 20 mM $MgCl_2$, 500 mM KCl), 10 units of RNase Inhibitor (GIBCO-BRL Cat#15518-012) and 20 units of DNaseI (GBICO-BRL Cat#18068-015). The volume is adjusted to 50 μl with additional DEPC treated water. The reaction is incubated at 37° C. for 30 minutes. After DNaseI digestion the RNAs are organic solvent-extracted with phenol and chloroform followed by ethanol precipitation. This represents the second ethanol precipitation of the isolated RNA. Empirical observations suggest that this repeated precipitation improves RNA performance in the RT reaction to follow.

Following DNaseI digestion, an aliquot of the RNA suspension in ethanol is removed and divided into thirds. A different procedure is performed on each one of the aliquot thirds. These three procedures are: (1). An $OD_{260/280}$ is obtained using a standard protocol and is used to estimate the amount of RNA present and its likely quality. (2). An aliquot is run out on an agarose gel, and the RNA is stained with ethidium bromide. Observation that both the 28S and 18S RNAs are visible as discreet bands and that there is little staining above the point at which the 28S rRNA migrates indicate that the RNA is relatively intact. While it is not critical to assay performance that the examined RNAs be completely free of partial degradation, it is important to determine that the RNA is not so degraded as to significantly effect the appearance of the 28S rRNA. (3). The total cell RNAs are run using a PCR-based test that confirms that the DNaseI treatment actually digested the contaminating genomic DNA to completion. It is very important to confirm complete digestion of genomic DNA because genomic DNA may act as a template in PCR reactions resulting in false positive signals in the relative quantitative RT-PCR assay described below. The assay for contaminating genomic DNA utilizes gene specific oligonucleotides that flank a 145 nucleotide long intron (intron #3) in the gene encoding Prostate Specific Antigen (PSA). This is a single copy gene with no psuedogenes. It is a member of the kallikrien gene family of serine proteases, but the oligonucleotides used in this assay are specific to PSA. The sequences of these oligonucleotides are:

5'CGCCTCAGGCTGGGGCAGCATT 3' (SEQ ID NO:79) and

5'ACAGTGGAAGAGTCTCATTCGAGAT 3' (SEQ ID NO:80).

In the assay for contaminating genomic DNA, 500 ng to 1.0 µg of each of the DNaseI treated RNAs are used as templates in a standard PCR (35–40 cycles under conditions describe below) in which the oligonucleotides described above are used as primers. Human genomic DNA is used as the appropriate positive control. This DNA may be purchased from a commercial vender. A positive signal in this assay is the amplification of a 242 nucleotide genomic DNA specific PCR product from the RNA sample being tested as visualized on an ethidium bromide stained electrophoretic gel. There should be no evidence of genomic DNA as indicated by this assay in the RNAs used in the RT-PCR assay described below. Evidence of contaminating genomic DNA results in redigestion of the RNA with DNaseI and reevaluation of the DNase treated RNA by determining its $OD_{260/280}$ ratio, examination on electrophoretic gel and retesting for genomic DNA contamination using the described PCR assay.

The standard conditions used for PCR (as mentioned in the last paragraph) are:

1× GIBCO-BRL PCR reaction buffer [20 mM Tris-Cl (pH 8.4), 50 mM KCl]

1.5 mM $MgCl_2$

200 µM each of the four dNTPs 200 nM each oligonucleotide primer concentration of template as appropriate 2.5 units of Taq polymerase per 100 µl of reaction volume.

Using these conditions, PCR is performed with 35–40 cycles of:

94° C. for 45 sec

55°–60° C. for 45 sec

72° C. for 1:00 minute.

The protocols described in the above section permit isolation of total cellular RNA that overcomes two of the six barriers to successful RT-PCR, i.e. the RNA is acceptably intact and is free from contaminating genomic DNA.

Reverse transcriptases, also called RNA dependent DNA polymerases, as applied in currently used molecular biology protocols, are known to be less processive than other commonly used nucleic acid polymerases. It has been observed that not only is the efficiency of conversion of RNA to cDNA relatively inefficient, there is also several fold variation in the efficiency of cDNA synthesis between reactions that use RNAs as templates that otherwise appear indistinguishable. The sources of this variation are not well characterized, but empirically, it has been observed that the efficiencies of some reverse transcription (RT) reactions may be improved by repeated organic extractions and ethanol precipitations. This implies that some of the variation in RT is due to contaminates in the RNA templates. In this case, the DNaseI treatment described above may be aiding the efficiency of RT by subjecting the RNA to an additional cycle of extraction with phenol and chloroform and ethanol precipitation. Contamination of the template RNA with inhibitors of RT is an important barrier to successful RT that is partially overcome by careful RNA preparation and repeated organic extractions and ethanol precipitations.

Reverse transcription reactions are performed using the Superscript™ Preamplification System for First Strand cDNA Synthesis kit which is manufactured by GIBCO-BRL LifeTechnologies (Gaithersburg, Md.). Superscript™ is a cloned form of M-MLV reverse transcriptase that has been deleted for its endogenous RNaseH activity in order to enhance its processivity. In the present example, the published protocols of the manufacturer are used for cDNA synthesis primed with random hexamers. cDNA synthesis may also be primed with a mixture of random hexamers (or other small oligonucleotides of random sequence) and oligo dT. The addition of oligo dT increases the efficiency of conversion of RNA to cDNA proximal to the polyA tail. As template, either 5 or 10 micrograms of RNA is used (depending on availability). After the RT reaction has been completed according to the protocol provided by GIBCO-BRL, the RT reaction is diluted with water to a final volume of 100 µl.

Even with the best prepared RNA and the most processive enzyme, there may be significant variation in the efficiency of RT. This variation would be sufficiently great that cDNA made in different RTs could not be reliably compared. To overcome this possible variation, cDNA populations made from different RT reactions may be normalized to contain equal concentrations of amplifiable cDNA synthesized from mRNAs that are known not to vary between the physiological states being examined. In the present examples, cDNAs made from total cell RNAs are normalized to contain equal concentrations of amplifiable β-actin cDNA.

One µl of each diluted RT reaction is subjected to PCR using oligonucleotides specific to β-actin as primers. These primers are designed to cross introns, permitting the differentiation of cDNA and genomic DNA. These β-actin specific oligonucleotides have the sequences:

5'CGAGCTGCCTGACGGCCAGGTCATC 3' (SEQ ID NO:81) and

5' GAAGCATTTGCGGTGGACGATGGAG 3' (SEQ ID NO:82)

PCR is performed under standard conditions as described previously for either 19 or 20 cycles. The resulting PCR product is 415 nucleotides in length. The product is examined by PCR using agarose gel electrophoresis followed by staining with ethidium bromide. The amplified cDNA fragment is then visualized by irradiation with ultra violet light using a transilluminator. A white light image of the illuminated gel is captured by an IS-1000 Digital Imaging System manufactured by Alpha Innotech Corporation. The captured image is analyzed using either version 2.0 or 2.01 of the software package supplied by the manufacturer to determine the relative amounts of amplified β-actin cDNA in each RT reaction.

To normalize the various cDNAs, water is added to the most concentrated cDNAs as determined by the assay described in the last paragraph. PCR using 1 µl of the newly rediluted and adjusted cDNA is repeated using the β-actin oligonucleotides as primers. The number of cycles of PCR must be increased to 21 or 22 cycles in order to compensate for the decreased concentrations of the newly diluted cDNAs. With this empirical method the cDNAs can be adjusted by dilution to contain roughly equal concentrations of amplifiable cDNA. Sometimes this process must be repeated to give acceptable final normalization. By dividing the average optical density of all observed bands by that of a particular band, a normalization statistic can be created that will permit more accurate comparisons of the relative abundances of RNAs examined in the normalized panel of cDNAs. A representative gel is shown if FIG. 12. An analysis of the data is shown in Table 4.

Figure 12:
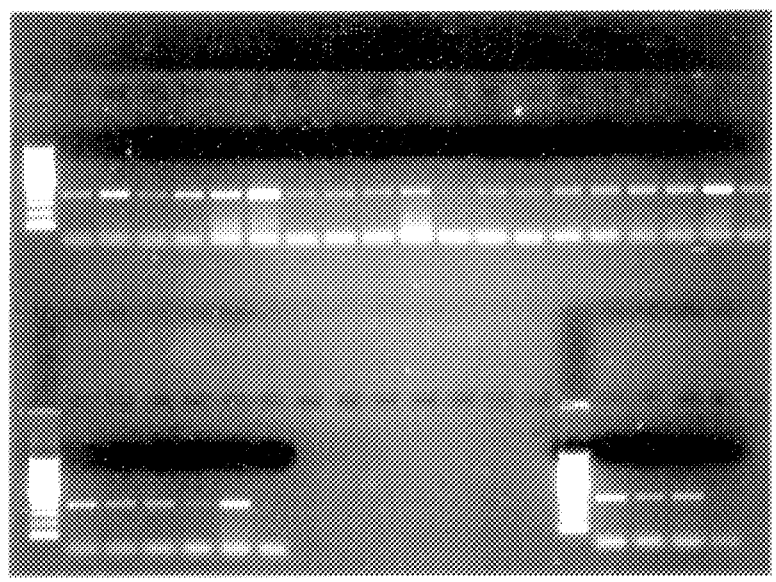
FIG. 12. Amplification of $\beta$-actin cDNA from 25 cDNAs synthesized from various prostate tissues. The physiological states of these tissue, being either normal prostates, glands with BPH or prostate tumors are given in Table 4. Also included on this image molecular weight markers displayed as "ladders" and three isolated bands representing the PCR products from pools of (left to right) normal, BPH and prostate cancers.
Figure 13:
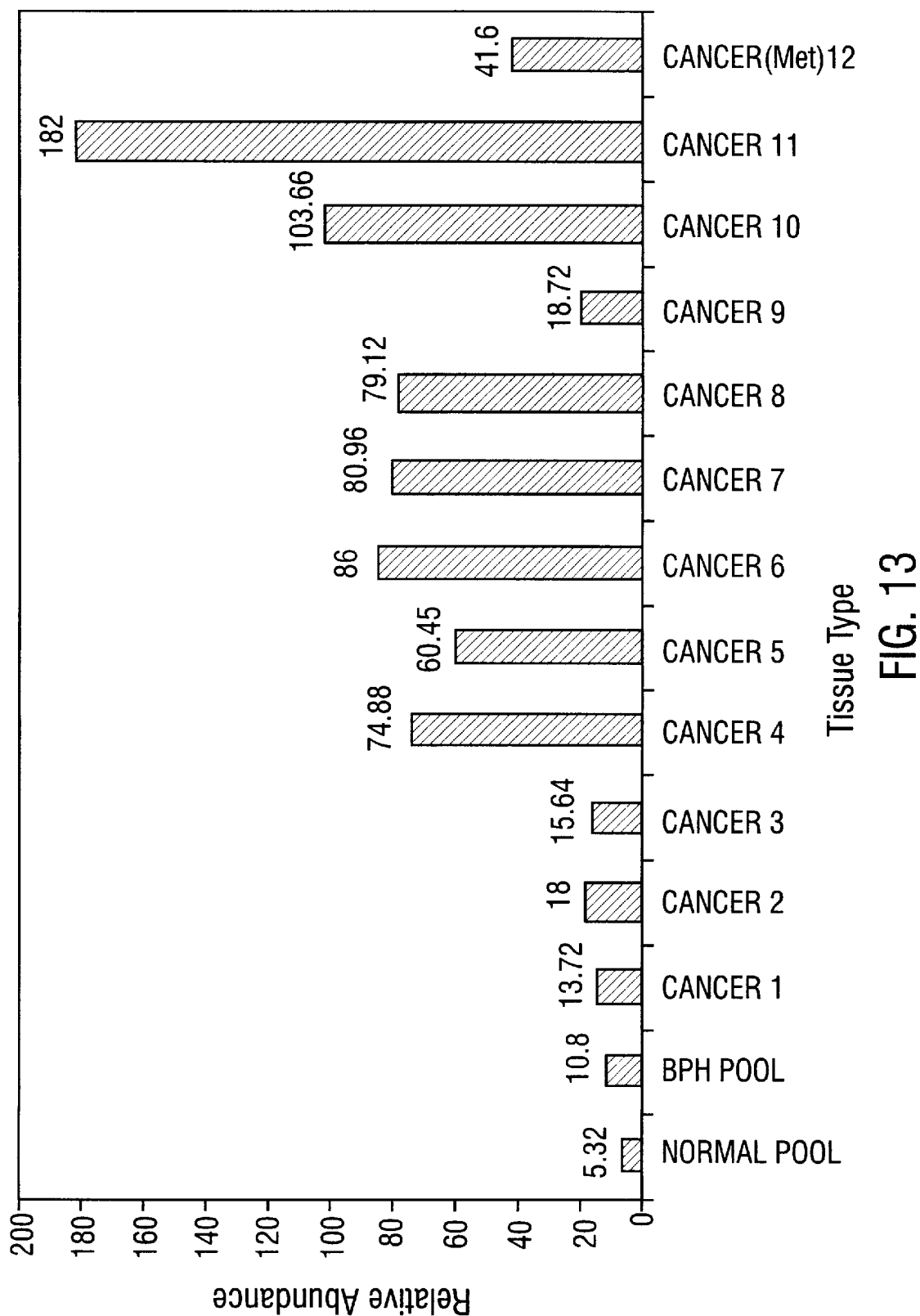
FIG. 13 Amplification of a cDNA fragment derived from the UC42 mRNA in the individual prostate cancers described in Table 4. Little are no detectable expression can be seen for this mRNA in either a pool of normal prostates or a pool of prostate glands with BPH. Strong signals from 7 of the 10 examined cancers indicates very significant induction of this gene in many prostate tumors. The normalized data is displayed graphically.

Once the normalization statistics are derived, PCR may be performed using different gene specific oligonucleotides as primers to determine the relative abundances of other mRNAs as represented as cDNAs in the normalized panel of diluted RT reaction products. In FIG. 13, data derived from PCR products amplified from the same RT reactions as described in FIG. 12 are shown. In this study, the differential abundance of a previously undescribed mRNA species is shown. From previous studies it was known that this mRNA was not significantly expressed in normal prostates or glands with BPH. It is clear from this data that this previously unknown gene, named UC42 (SEQ ID NO:18), is not significantly expressed in the average normal prostate, nor in glands with BPH. Among the examined tumors, most show very strong expression of UC42. The intensities of the bands produced from the PCR amplification of the UC42 cDNA fragment were then measured using the IS 1000 image analysis system. The data is shown in Table 4. The relative intensities of the UC42 bands is then adjusted and normalized to β-actin expression by multiplying the intensity quantities by the normalization statistics derived as shown in Table 4. These normalized values represent the relative abundances UC42 mRNA in the surveyed tissues. The derived normalized values are represented graphically in FIG. 13.

UC42 is an example of differential expression with a high level of induction in most prostate tumors relative to normal prostates and those with BPH. Most mRNA species are not as differentially expressed as is UC42. An example of this is the mRNA encoding the transmembrane tyrosine kinase receptor, Hek, that is significantly up regulated in BPH as compared to normal prostates.

Figure 14:
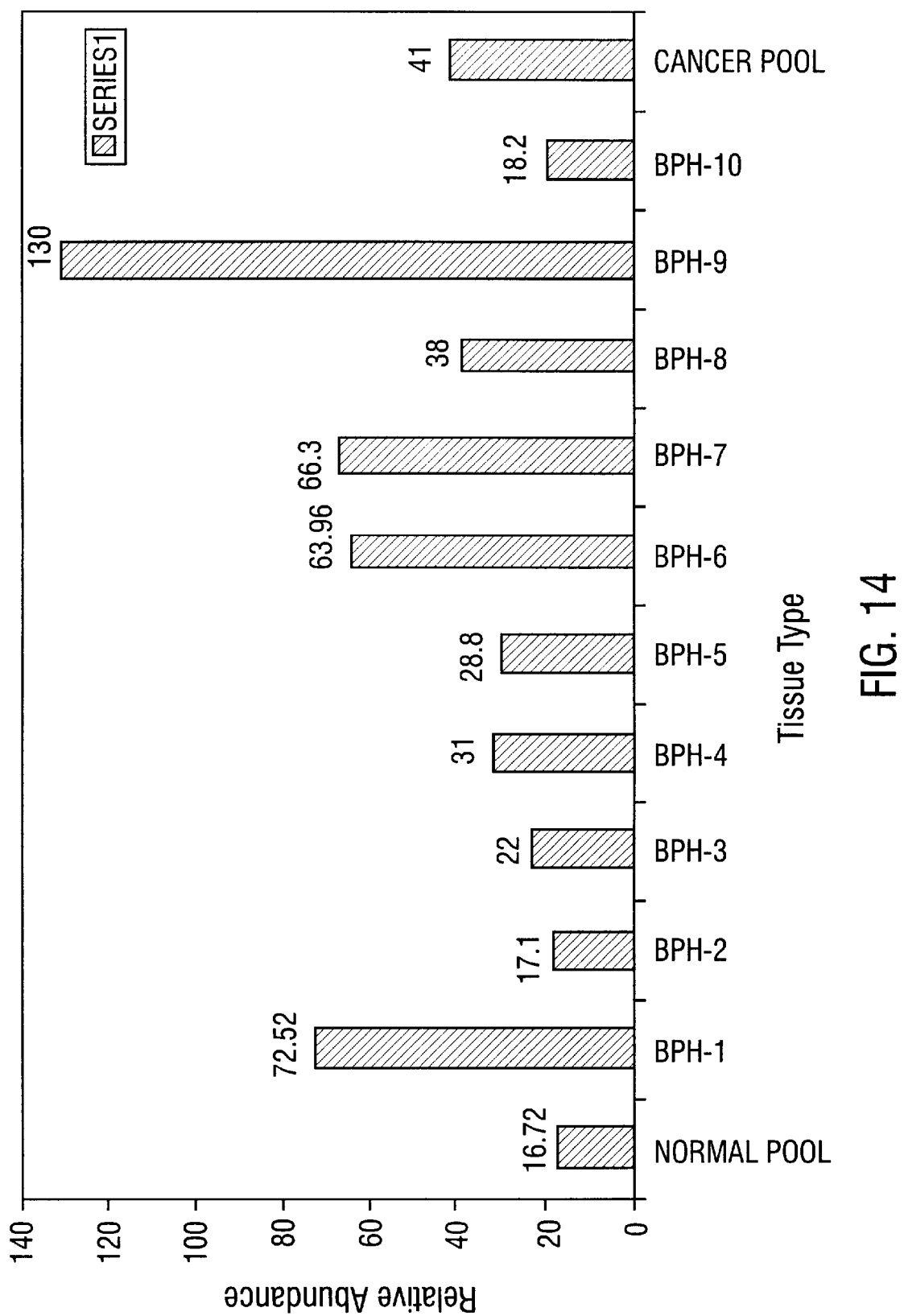
FIG. 14 Amplification of a cDNA fragment derived from the Hek (UC205) mRNA in the individual prostate cancers described in Table 4. Many, but not all, prostate glands with BPH are seen to have higher levels of expression of Hek than seen in a pool of normal glands. Examination of a gel also indicated that some of the PCRs are not in the linear phase of their amplification curves. Data was captured on the IS 1000 and normalized as described in Table 4.

In an examination of the relative abundance levels of Hek mRNA, the normal and tumor specimens were examined as pools. Low level expression was observed in the pool of normal prostate tissues relative to that observed in BPH. By normalizing these values to the β-actin standard using the normalization statistics, it is possible to quantify this difference in the relative abundances of Hek mRNA. These normalized data are displayed graphically in the bar graph shown in FIG. 14. Similar to the observations made for UC42, most but not all of the BPH specimens showed elevated abundances of Hek mRNA relative to a pool of normal prostates. On average, the abundance of Hek mRNA was observed to be 2.9 fold higher in the BPH specimens than in an average normal prostate gland as represented by the pool of normal glands.

While these observations are consistent with many similar studies that examined Hek expression using other tissue samples and cDNAs, they vary from observations described in the next section in which an RT-PCR assay is discussed that uses pooled cDNAs and is more likely to capture data from PCRs while in the linear portions of their amplification curves. It was fairly obvious from the data obtained in the Hek study that at least some of the RT-PCR reactions were not in the linear portions of their amplification curves when the data was captured. This was concluded from observation that the intensity of the bands from BPH9 slightly decreased from a sample taken at 35 to a sample taken at 40 cycles. To a lesser extent this was true for other samples as well. This is a strong indication that the PCRs had left the linear portions of their amplification curves. While this observation limits the qualitative value of this experiment, it does not necessarily limit the ability of the assay to determine qualitative differences in mRNA abundances. The error caused by observing PCRs after the linear portion of PCR is in the direction of quantitatively underestimating mRNA abundance differences. It is still valid to conclude that Hek is up regulated in many prostate glands with BPH even if the absolute fold increase in abundance can not be determined. By looking at individuals, it is possible to examine questions as to what portion of individuals of a particular physiologic class, i.e. individuals with BPH, similarly regulate the mRNA being examined. To determine quantitative differences in mRNA expression, it is necessary that the data is collected in the linear portion of the respective PCR amplification curves. This requirement is met in the assay described in following paragraphs.

The last two barriers to RT-PCR are addressed in the sections that follow involving the use of pooled cDNAs as templates in RT-PCR. In practice, the protocols using pooled templates are usually performed before the protocol described above.

There are two additional barriers to relative mRNA quantitation with RT-PCR that frequently compromise interpretations of results obtained by this method. The first of these involves the need to quantify the amplification products while the PCR is still in the linear portion of the process where "E" behaves as a constant and is nearly equal to two. In the "linear" portion of the amplification curve, the log of the mass of the amplified product is directly proportional to the cycle number. At the end of the PCR process, "E" is not constant. Late in PCR, "E" declines with each additional cycle until there is no increase in PCR product mass with additional cycles. The most important reason why the efficiency of amplification decreases at high PCR cycle number, may be that the concentration of the PCR products becomes high enough that the two strands of the product begin to anneal to each other with a greater efficiency than that at which the oligonucleotide primers anneal to the individual product strands. This competition between the PCR product strands and the oligonucleotide primers creates a decrease in PCR efficiency. This part of the PCR where the efficiency of amplification is decreased is called the "plateau" phase of the amplification curve. When "E" ceases to behave as a constant and the PCR begins to move towards the plateau phase, the conservation of relative proportionality of amplified products during PCR is lost. This creates an error in estimating the differences in relative abundance of an mRNA species occurring in different total cell RNA populations. This error is always in the same direction, in that it causes differences in relative mRNA abundances to appear less than they actually are. In the extreme case, where all PCRs have entered the plateau phase, this effect will cause differentially expressed mRNAs to appear as if they are not differentially expressed at all.

To control for this type of error, it is important that the PCR products be quantified in the linear portion of the amplification curve. This is technically difficult because currently used means of DNA quantitation are only sensitive enough to quantify the PCR products when they are approaching concentrations at which the product strands begin to compete with the primers for annealing. This means that the PCR products can only be detected at the very end of the linear range of the amplification curve. Predicting in advance at what cycle number the PCR products should be quantified is technically difficult.

Practically speaking, it is necessary to sample the PCR products at a variety of cycle numbers that are believed to span the optimum detection range in which the products are abundant enough to detect, but still in the linear range of the amplification curve. It is impractical to do this in a study that involves large numbers of samples because the number of different PCR reactions and/or number of different electrophoretic gels that must be run becomes prohibitively large.

To overcome these limitations, a two tiered approach has been designed to relatively quantitate mRNA abundance levels using RT-PCR. In the first tier, pools of cDNAs produced by combining equal amounts of normalized cDNA are examined to determine how mRNA abundances vary in the average individual with a particular physiological state. This reduces the number of compared samples to a very small number such as two to four. In the studies described herein, three pools are examined. These are pools of normal prostates, those with BPH and a variety of prostate tumors. Each pool may contain a large number of individuals. While this approach does not discriminate differences between individuals, it can easily discern broad patterns of differential expression. The great advantage of examining pooled cDNAs is that it permits many duplicate PCR reactions to be simultaneously set up.

The individual duplicates can be harvested and examined at different cycle numbers of PCR. In studies described below, four duplicate PCR reactions were set up. One duplicate was collected at 31, 34, 37, and 40 PCR cycles. Occasionally, PCR reactions were also collected at 28 cycles. Examining the PCRs at different cycle numbers yielded the following benefits. It is very likely that at least one of the RT-PCRs will be in the optimum portion of the amplification curves to reliably compare relative mRNA abundances. In addition, the optimum cycle number will be known, so that studies with much larger sample sizes, such as the studies with UC42 and Hek described above, are much more likely to succeed. This is the second tier of a two tiered approach that has been taken to relatively quantitate mRNA abundance levels using RT-PCR. Doing the RT-PCR with the pooled samples permits much more efficient application of RT-PCR to the samples derived from individuals. A further benefit, also as discussed below, tube to tube variability in PCR can be discounted and controlled because most studies yield multiple data points due to duplication.

Like the previously described protocol involving individuals, the first step in this protocol is to normalize the pooled samples to contain equal amounts of amplifiable cDNA. This is done using oligonucleotides that direct the amplification of β-actin. In this example, a PCR amplification of a cDNA fragment derived from the β-actin mRNA from pools of normal prostates, glands with BPH and prostate tumors was performed. This study was set up as four identical PCR reactions. The products of these PCRs were collected and electrophoresed after 22, 25, 28 and 31 PCR cycles. Quantitation of these bands using the IS 1000 system shows that the PCRs are still in the linear ranges of their amplification curves at 22, 25 and 28 cycles but that they have left linearity at 31 cycles. This is known because the ratios of the band intensities remain constant and internally consistent for the data obtained from 22, 25 and 28 cycles, but these ratios become distorted at 31 cycles. This quantitation will also permit the derivation of normalizing statistics for the three pools relative to each other in exactly the same manner as was done previously for individuals (Table 4).

This study is then repeated using gene specific primers for a gene other than β-actin. For purposes of comparison, the mRNAs examined were the same as were previously shown, UC42 and Hek. As was done previously for the samples derived from individuals, the intensities of the relevant bands were quantitated using the IS 1000 and normalized to the β-actin signals. UC42 is abundantly expressed in prostate tumors as indicated by the PCR. This fragment entered stationary phase even at 31 cycles of PCR. UC42 is, therefore, close to being transcriptionally silent in normal prostates and those with BPH and is abundantly "turned on" in many prostate tumors. This is shown by there being no signal for UC42 mRNA in either normal or BPH at any cycle number up to 40. Clearly, UC42 is abundantly differentially expressed in prostate cancer and is a likely candidate for being an informative biomarker for this disease.

For Hek, the data deserves more interpretation. While the Hek derived PCR product was observable at 34 cycles of PCR, the Hek PCR product was not nearly as abundant as that of UC42. At 40 cycles, the Hek derived PCR product was present as a bold band in the PCRs using either the pooled BPH samples or pooled prostate tumor samples as templates. The Hek band obtained when a pool of normal prostates is examined is barely visible. It is clear that Hek is more abundantly expressed in BPH and prostate tumors than it is in normal glands. Quantitation and normalization of this data as described previously was performed and shown in the bar graph in FIG. 15.

Figure 15:
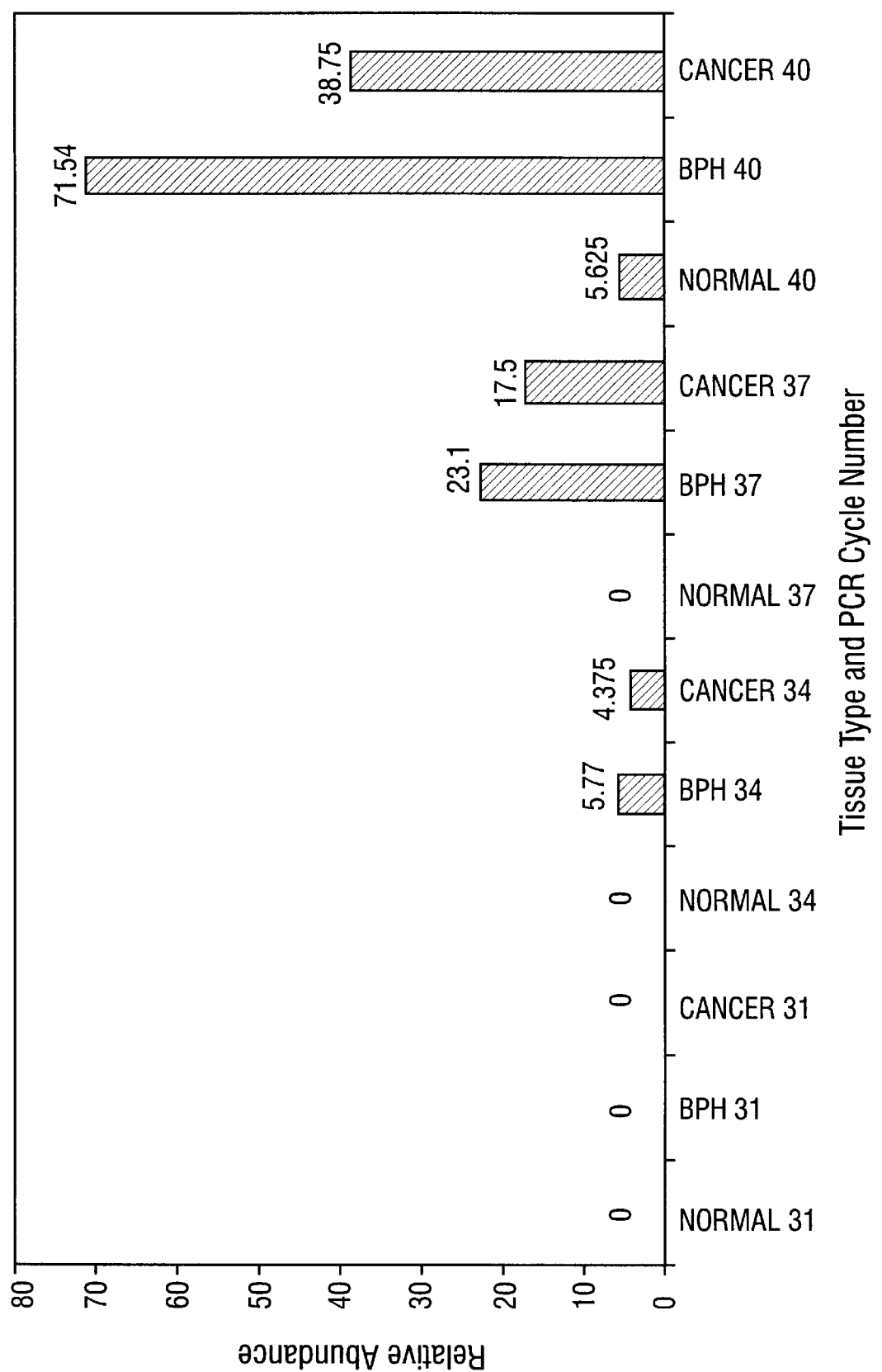
FIG. 15. β-actin normalization of pooled cDNAs. Pools of cDNAs synthesized from either normal prostates (N), prostate glands with BPH (B) or prostate tumors (C) were used as templates for β-actin cDNA amplification. Four identical sets of PCRs were set up. These were stopped and examined after differing numbers of PCR cycles. The data for the 22 cycles were numerically captured on by the IS1000 and used to derive normalizing statistics. The normalizing statistics are obtained by dividing the average intensity of the three captured bands by the value of the three bands separately. These normalizing statistics were then used to normalize the data obtained from the mRNA of Hek (UC205). Hek mRNA is more abundant in the BPH and prostate cancer pools than in the pool of normal prostates. At 34 and 37 cycles, the PCRs for the BPH and cancer pools are observed in the linear phase of their amplifcation curves. The data was normalized to the β-actin data.

The central question to be answered in analyzing this data is whether the PCRs have been examined in the linear portions of their amplification curves. A test for this can be devised by determining if the proportionality of the PCR products has been conserved as PCR cycle number has increased. At 34 cycles, the Hek product is observed at 5.77 and 4.375 relative abundance units respectively for the pooled BPH and cancer samples as shown in FIG. 15. The ratio of these values is 1.32. Similarly, at 37 cycles the values for BPH and cancer are 23.1 and 17.5. The ratio of these values is also 1.32. This is strong evidence that the PCRs were in the linear portions of their amplification curves when these observations were made. (This is better conservation of proportionality than is frequently observed. In some studies, data was excepted when the rations were similar but not identical.) This conservation of proportionality is lost at 40 cycles. The ratio of the BPH and cancer values has increased to 1.85. This indicates that these PCRs are nearing the plateau phases of their amplification curves. Further evidence that the plateau phase is nearing can be directly observed in the relative increases in the numerical data observed in this study. From 34 to 37 cycles of PCR the mass of the observed PCR products increased 4.0 fold in both the BPH and cancer reactions. Similar calculations of the increase in signals between 37 and 40 cycles indicate a 3.1 fold increase in the BPH reactions and only a 2.2 fold increase for the cancer reactions. In both cases, "E" is declining, and the reactions are nearing their plateau phases.

For the reactions that attempted to amplify Hek cDNA from a pool of normal prostates, a band was only observed at 40 cycles. Since the BPH and cancer reactions had left their linear phases, direct numerical quantitation of the fold increase in abundance between normal, BPH and cancer is not possible. It is, however, valid to conclude that Hek mRNA is more abundant in samples derived from BPH or prostate tumors than it is in normal prostate glands. It may also be true that Hek is more abundant in the average BPH specimen than it is in the average prostate tumor. This has been observed in many studies including the one shown here, but the difference in relative expression of Hek between BPH and prostate cancers is always small, as it is here. It is possible that the higher levels of expression in the tumor pool relative to normal prostates may be due to BPH tissue contaminating the tumor specimens. Alternatively, it may be due to higher Hek expression in the tumors themselves. Examination of tissue by in situ hybridization or by immunohistochemical methods may be required to distinguish between these possibilities.

The final major barrier to quantifying relative mRNA abundances with RT-PCR is tube to tube variability in PCR. This can result from many factors, including unequal heating and cooling in the thermocycler, imperfections in the PCR tubes and operator error. To control for this source of variation, the Cole-Parmer digital thermocouple Model #8402-00 was used to calibrate the thermocyclers used in these studies. Only slight variations in temperature were observed. To rigorously demonstrate that PCR tube to tube variability was not a factor in the studies described above, 24 duplicate PCRs for β-actin using the same cDNA as template were performed. These PCR tubes were scattered over the surface of a 96 well thermocycler, including the corners of the block where it might be suspected the temperature might deviate from other areas. Tubes were collected at various cycle numbers. Nine tubes were collected at 21 cycles. Nine tubes were collected at 24 cycles, and six tubes were collected at 27 cycles. Quantitation of the intensities of the resulting bands with the IS 1000 system determined that the standard error of the mean of the PCR product abundances was ±13%. This is an acceptably small number to be discounted as a major source of variability in an RT-PCR assay.

The RT-PCR protocol examining pooled cDNAs is internally controlled for tube to tube variability that might arise from any source. By examining the abundance of the PCR products at several different cycle numbers, it can be determined that the mass of the expected PCR product is increasing appropriately with increasing PCR cycle number. Not only does this demonstrate that the PCRs are being examined in the linear phase of the PCR, where the data is most reliable, it demonstrates that each reaction with the same template is consistent with the data from the surrounding cycle numbers. If there was an unexplained source of variation, the expectation that PCR product mass would increase appropriately with increasing cycle number would not be met. This would indicate artifactual variation in results. Internal duplication and consistency of the data derived from different cycle numbers controls for system derived variation in tube to tube results.

As described in the preceding paragraphs, the RT-PCR protocol using pooled cDNA templates overcomes the last two barriers to effective relative quantitative RT-PCR. These barriers are the need examine the PCR products while the reactions are in the linear portions of their amplification curves and the need to control tube to tube variation in PCR. The described protocol examines PCR products at three to four different cycle numbers. This insures that the PCRs are quantitated in their linear ranges and, as discussed in the last paragraph, controls for possible tube to tube variation. One final question is whether β-actin is an appropriate internal standard for mRNA quantitation. β-actin has been used by many investigators to normalize mRNA levels. Others have argued that β-actin is itself differentially regulated and therefore unsuitable as an internal normalization standard. In the protocols described herein differential regulation of β-actin is not a concern. More than fifty genes have been examined for differential expression using these protocols. Fewer than half were actually differentially expressed. The other half were regulated similarly to β-actin within the standard error of 13%. Either all of these genes are coordinately differentially regulated with β-actin, or none of them are differentially regulated. The possibility that all of these genes could be similarly and coordinately differentially regulated with β-actin seems highly unlikely. This possibility has been discounted.

β-actin has also been criticized by some as an internal standard in PCRs because of the large number of pseudogenes of β-actin that occur in mammalian genomes. This is not a consideration in the described assays because all of the RNAs used herein are demonstrated to be free of contaminating genomic DNA by a very sensitive PCR based assay. In addition, the cycle number of PCR needed to detect β-actin cDNA from the diluted RT reactions, usually between 19 and 22 cycles, is sufficiently low to discount any contribution that genomic DNA might make to the abundance of amplifiable β-actin templates.

TABLE 4

Raw Numerical Data Captured on the IS1000 and Normalization by Comparison to B-Actin

| Type of Tissue | Raw Data B-Actin | Raw Data corrected for background | Normalizing Statistic | Raw Data for UC42 | Normalized Data for UC42 | Raw Data for Hek (UC205) | Normalized Data for Hek (Uc205) |
| --- | --- | --- | --- | --- | --- | --- | --- |
| Normal Pool 1 | 16 | 11 | 1.42 | | | | |
| Normal Pool 2 | 35 | 30 | 0.52 | | | | |
| Total normal Pool | 25.5 | 20.5 | 0.76 | 7 | 5.32 | 22 | 16.72 |
| BPH1 | 13 | 8 | 1.96 | | | 37 | 72.52 |
| BPH2 | 27 | 22 | 0.71 | | | 10 | 17.1 |
| BPH3 | 36 | 31 | 0.5 | | | 44 | 22 |
| BPH4 | | | 1 | | | 31 | 31 |
| BPH5 | 18 | 13 | 1.2 | | | 24 | 28.8 |
| BPH6 | 15 | 10 | 1.56 | | | 41 | 63.96 |
| BPH7 | 17 | 12 | 1.3 | | | 51 | 66.3 |
| BPH8 | 21 | 16 | 0.975 | | | 39 | 38 |
| BPH9 | 11 | 6 | 2.6 | | | 50 | 130 |
| BPH10 | 17 | 12 | 1.3 | | | 14 | 18.2 |
| BPH Pool | 19.4 | 14.4 | 1.08 | 10 | 10.8 | | |
| Cancer1 | 13 | 8 | 1.96 | 7 | 13.72 | | |
| Cancer2 | 18 | 13 | 1.2 | 15 | 18 | | |
| Cancer3 | 22 | 17 | 0.92 | 17 | 15.64 | | |
| Cancer4 | 25 | 20 | 0.78 | 96 | 74.88 | | |
| Cancer5 | 29 | 24 | 0.65 | 93 | 60.45 | | |

TABLE 4-continued

Raw Numerical Data Captured on the IS1000 and Normalization by Comparison to B-Actin

| Type of Tissue | Raw Data B-Actin | Raw Data corrected for background | Normalizing Statistic | Raw Data for UC42 | Normalized Data for UC42 | Raw Data for Hek (UC205) | Normalized Data for Hek (Uc205) |
|---|---|---|---|---|---|---|---|
| Cancer6 |  |  | 1 | 86 | 86 |  |  |
| Cancer7 | 22 | 17 | 0.92 | 88 | 80.96 |  |  |
| Cancer8 | 22 | 17 | 0.92 | 86 | 79.12 |  |  |
| Cancer9 | 15 | 10 | 1.56 | 12 | 18.72 |  |  |
| Cancer10 | 16 | 11 | 1.42 | 73 | 103.66 |  |  |
| Cancer11 | 11 | 6 | 2.6 | 70 | 182 |  |  |
| Cancer(Met)12 | 34 | 29 | 0.54 | 77 | 41.6 |  |  |
| Cancer Pool | 20.6 | 15.7 | 1 |  |  | 41 | 41 |
| No template | 5 | 0 |  |  |  |  |  |
| Background | 5 | 0 |  |  |  |  |  |
| Total | 497.9 | 377.9 |  |  |  |  |  |
| Average | 20.6 | 15.6 |  |  |  |  |  |

Example 2

Identification of Markers of Prostate Disease by RNA Fingerprinting

The technique of RNA fingerprinting was used to identify differentially expressed RNA species isolated from primary human prostate tumors or human prostate cancer cell lines grown in culture as described above. About 400 bands were observed in these studies. A number of these appeared to be differentially expressed, and were cloned as described above.

Slot blots of total cell RNA probed with riboprobes indicated that ten of the clones were differentially expressed. These ten cloned PCR products chosen for further analysis were named UC Band #4-2 (SEQ ID NO:6), UC Band #5-2 (A and B), UC Band #7-1, UC Band #8-1, UC Band #25 (SEQ ID NO:1), UC Band #27 (SEQ ID NO:2), UC Band #28 (SEQ ID NO:3), UC Band #31 (SEQ ID NO:4), UC Band #32 (SEQ ID NO:7) and UC Band #33 (SEQ ID NO:5).

Early studies were performed utilizing total cell RNA from isolated human prostate cell lines grown in tissue culture. Prostate disease markers identified in this series of studies include UC Band #4-2, UC Band #5-2 (A and B), UC Band #7-1 and UC Band #8-1. Riboprobes made from these clones were used as probes against Northern blots of the cell line derived total cell RNAs. UC Band #8-1 was only marginally differentially expressed and therefore not examined in the RT-PCR assay described below.

Later studies were performed using total cell RNA isolated from human prostate glands and primary human prostate tumor samples. The prostate disease markers discovered in this series of studies include UC Band #25 (SEQ ID NO:1), UC Band #28 (SEQ ID NO:3), UC Band #31 (SEQ ID NO:4), UC Band #32 (SEQ ID NO:7) and UC Band #33 (SEQ ID NO:5). Differential expression of these gene products in human prostate tumors compared with benign and normal prostate tissues was confirmed by quantitative RT-PCR, as described below.

DNA sequence determination indicated that UC Band #25 (SEQ ID NO:1), UC Band #27 (SEQ ID NO:2), UC Band #28 (SEQ ID NO:3), UC Band #31 (SEQ ID NO:4) and UC Band #33 (SEQ ID NO:5) were previously unknown genes. UC Band #4-2 (SEQ ID NO:6) was derived from the mRNA of α6-integrin. UC Band #32 (SEQ ID NO:7) was derived from the mRNA of fibronectin. The results with the latter two gene products are interesting because all of these genes have been previously identified as being differentially expressed in some cancers.

The α6-integrin is known in prostate cancer to be both up regulated and inappropriately distributed on the cell surface (Knox et al., 1994). Urinary fibronectin has been proposed as a potential biomarker for prostatic cancer (Webb & Lin, 1980.)

Figure 2:
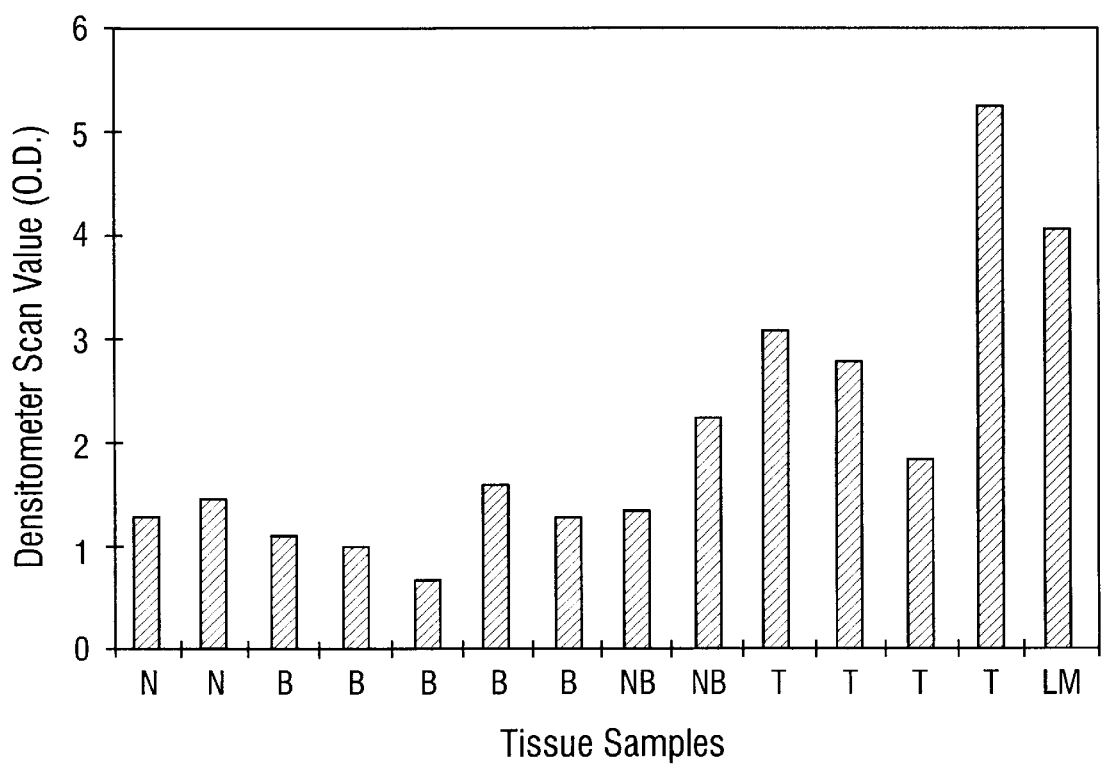
FIG. 2. Normalized quantitative RT-PCR of UC Band #27 (SEQ ID NO:2) shows that it is elevated in prostate cancers compared with normal or benign prostates. N=normal prostate, B=benign prostatic hyperplasia (BPH), NB=needle core biopsy of prostate cancer, T=primary prostate cancer, LM=metastatic lymph node prostate cancer, NC=negative control.
Figure 3:
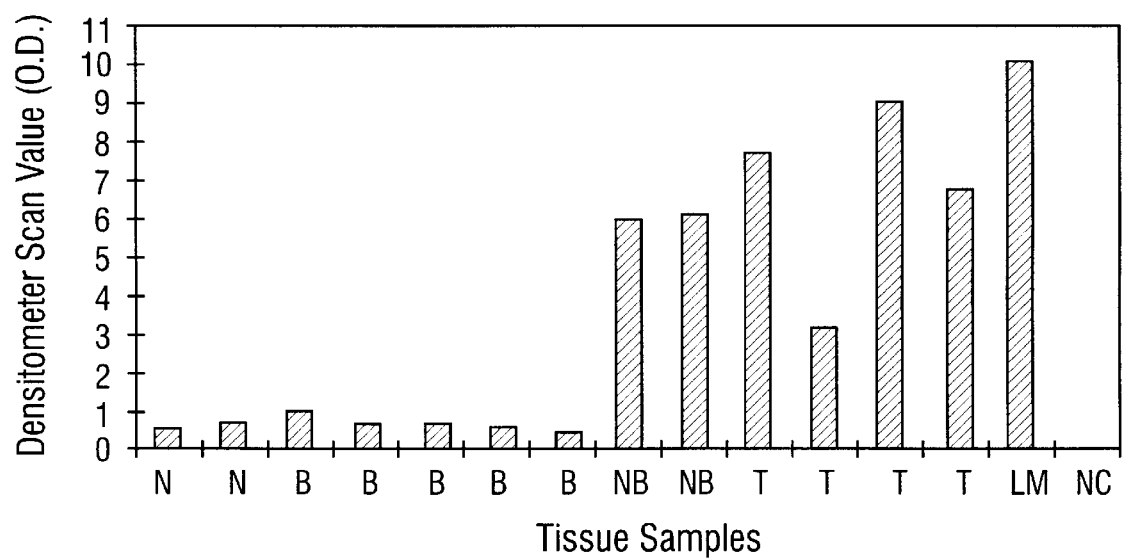
FIG. 3. Normalized quantitative RT-PCR of UC Band #28 (SEQ ID NO:3) shows that it is elevated in prostate cancers, particularly in metastatic prostate cancer, compared with normal or benign prostates. N=normal prostate, B=benign prostatic hyperplasia (BPH), NB=needle core biopsy of prostate cancer, T=primary prostate cancer, LM=metastatic lymph node prostate cancer, NC=negative control.
Figure 4:
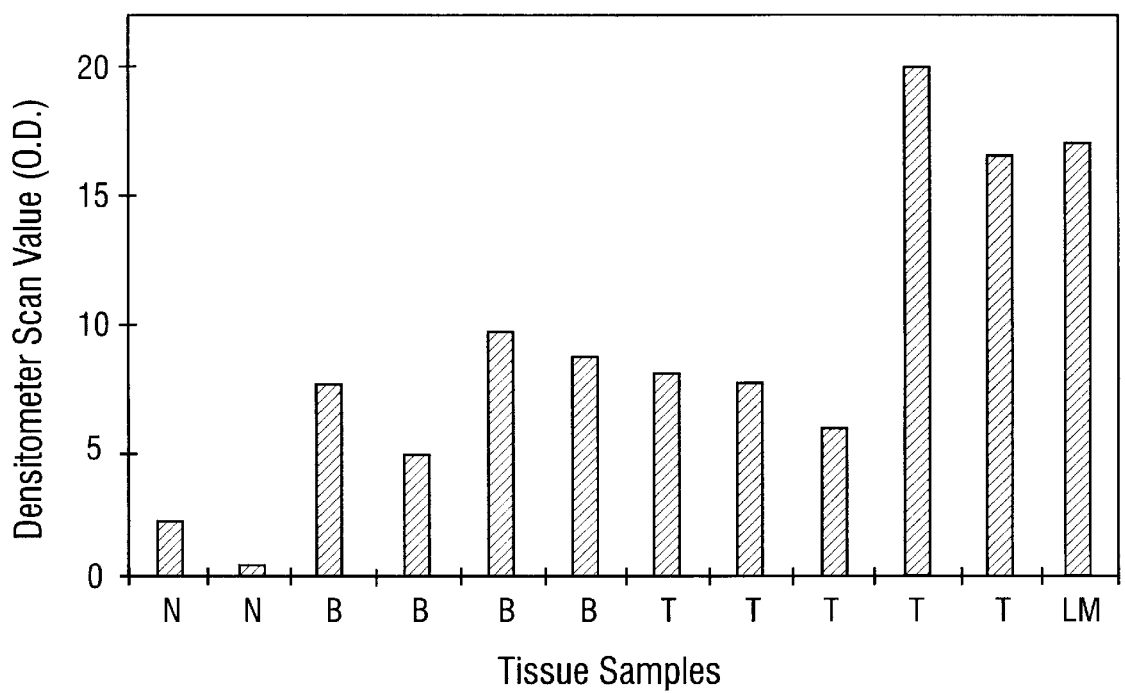
FIG. 4. Normalized quantitative RT-PCR of UC Band #31 (SEQ ID NO:4) shows that it is overexpressed in benign and malignant prostate compared with normal prostate. N=normal prostate, B=benign prostatic hyperplasia (BPH), NB=needle core biopsy of prostate cancer, T=primary prostate cancer, LM=metastatic lymph node prostate cancer, NC=negative control.

The levels of expression for UC Band #5-2 (A and B), UC Band #25, UC Band #27, UC Band #28, UC Band #31, UC Band #33, fibronectin and lipocortin II were analyzed by the quantitative RT-PCR protocol in samples of normal, benign and malignant prostate glands. The results for UC Band #25 (SEQ ID NO:1), (FIG. 1), UC Band #27 (SEQ ID NO:2), (FIG. 2), UC Band #28 (SEQ ID NO:3), (FIG. 3), UC Band #31 (SEQ ID NO:4), (FIG. 4), and UC Band #33 (SEQ ID NO:5), all show an increased level of expression in prostate carcinomas (NB, T and LM) compared with benign (B) and normal (N) prostate samples.

Figure 6:
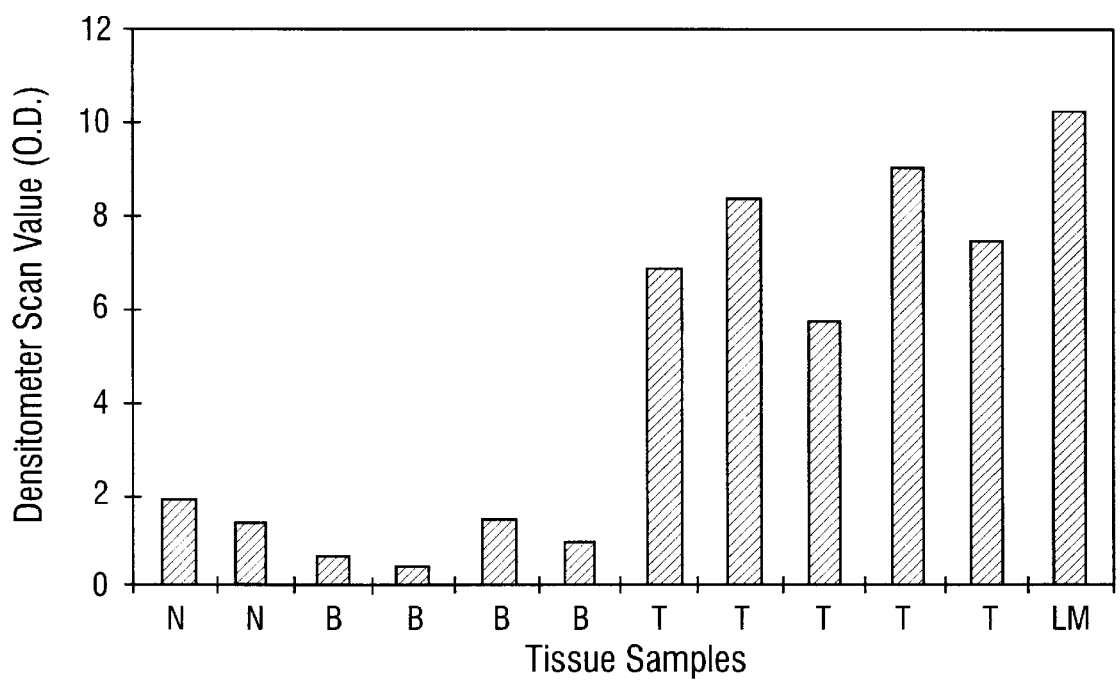
FIG. 6. Normalized quantitative RT-PCR of UC Band #33 (SEQ ID NO:5) shows that it is overexpressed in prostate cancers compared with normal or benign prostate. N=normal prostate, B=benign prostatic hyperplasia (BPH), NB=needle core biopsy of prostate cancer, T=primary prostate cancer, LM=metastatic lymph node prostate cancer, NC=negative control.

The results for UC Band #28 (FIG. 3) and UC Band #33 (FIG. 6) are particularly striking. These clones are expressed at very low levels in normal or benign prostate, and at significantly higher levels in metastatic and nonmetastatic prostate cancers. As such, they would provide excellent markers for the detection of malignant prostate tumors in biopsy samples containing a mixture of normal, benign and malignant prostate. The skilled practitioner will realize that all of these clones, particularly UC Band #28 and UC Band #33, have utility for the detection and diagnosis of prostate cancer, and such uses are included within the scope of the present invention.

Figure 5:
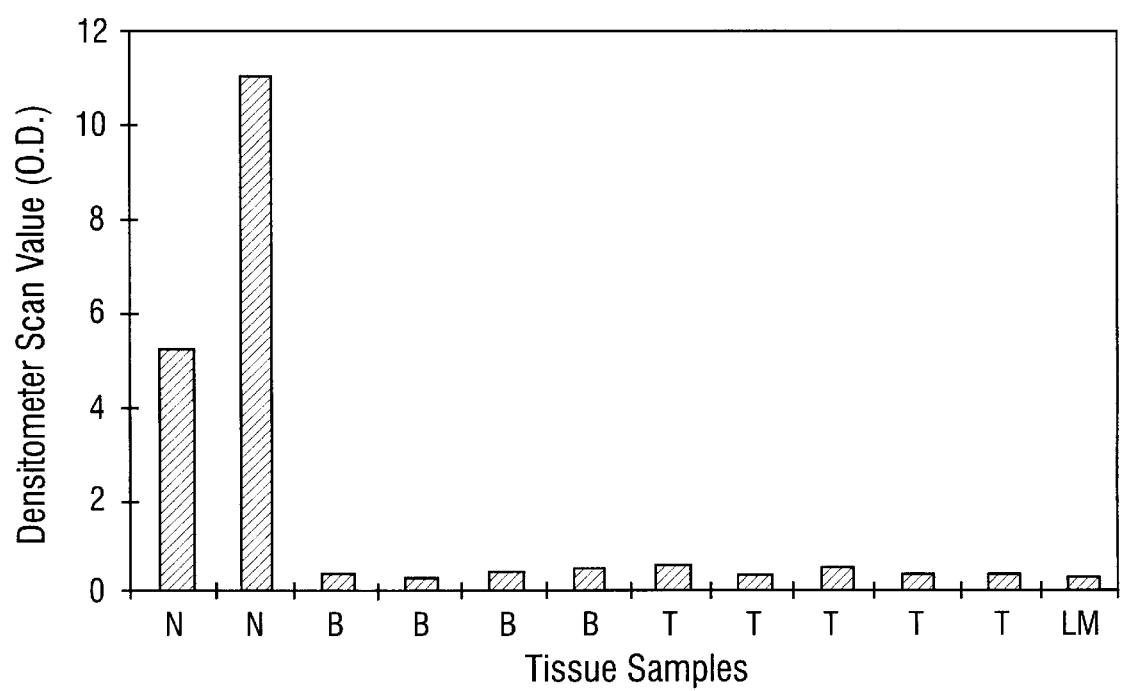
FIG. 5. Normalized quantitative RT-PCR of a sequence from the human fibronectin gene (SEQ ID NO:7) shows that it is down regulated in BPH and prostate cancer compared with normal prostate. N=normal prostate, B=benign prostatic hyperplasia (BPH), NB=needle core biopsy of prostate cancer, T=primary prostate cancer, LM=metastatic lymph node prostate cancer, NC=negative control.

The RT-PCR analysis for fibronectin (UC Band #32, FIG. 5) is also interesting. This marker appears to only be expressed in normal prostate samples, and is present at very low levels in either benign or malignant prostate (FIG. 5). The down regulation of fibronectin expression in BPH is a novel result. This observation is surprising in light of the previous report that fibronectin is a potential marker for prostate cancer. (Webb and Lin, 1980.) Those experienced in the art will realize that loss of fibronectin expression in BPH is of utility in diagnosing and detecting this condition in patients. The mRNAs for UC Band #5-2 (A and B) and lipocortin II, while differentially expressed in the cell lines were not differentially expressed in tumors.

Further RNA fingerprinting studies were done to identify genes that are differentially regulated at the level of mRNA transcription in normal prostate glands, glands with BPH, prostate tumors and metastases of prostate tumors. Differential expression was confirmed by relative quantitative RT-PCR. The oligonucleotides used are listed in Table 2. These studies resulted in the discovery of additional sequences that were differentially regulated. These sequences are designated herein as UC38, SEQ ID NO:10; UC40, SEQ ID NO:11; UC41, SEQ ID NO:12; UC42, SEQ ID NO:18; UC43, SEQ ID NO:19; UC45, UC46, UC47, matches GenBank Accession #M34840, prostatic acid phosphatase Nt 901-2095; UC201, SEQ ID NO:13; UC202, UC203, UC204 (matches GB#Z28521 and GB#D42055), SEQ ID NO:20; UC205 (Humhek, GB#H8394, sense strand), SEQ ID NO:14; UC206 (antisense strand), UC207 (sense strand), SEQ ID NO:15; UC208 (sense strand), UC209, SEQ ID NO:16; UC210 (sense strand), SEQ ID NO:17; UC211 (antisense strand), SEQ ID NO:21; UC212 (sense strand), SEQ ID NO:22; and UC213 (sense strand, matches GB#T07736), SEQ ID NO:23. Of these UC38, UC41, UC42, UC47 and UC211 are more abundant in tumors and are potential tumor markers. UC40, UC205 and UC207 are more abundant in BPH. UC43 is more abundant in normal and BPH glands and is a potential tumor suppressor. UC201 and UC210 are more abundant in some tumors and are potential progression markers. UC212 is more abundant in BPH and perhaps in some tumors. UC209 is down regulated in some tumors and is a possible suppressor of progression, and UC213 is down regulated in tumors.

Those experienced in the art will recognize that the genes and gene products (RNAs and proteins) for the above described markers of prostate disease and normal prostate marker are included within the scope of the invention herein described. Those experienced in the art will also recognize that the diagnosis and prognosis of prostatic cancer by detection of the nucleic acid products of these genes are included within the scope of the present invention.

3. Detection of Differentially Expressed RNA Species Using Primers Specific for TGF-β and Cyclin A Relative quantitative RT-PCR with an external standard proved to be a powerful means to examine mRNAs for differential expression in prostate cancer. Other genes were examined for differential expression by these means. These were selected because they were either known to be up regulated as a consequence of transformation or could be hypothesized to be up regulated as a consequence of transformation.

Figure 7:
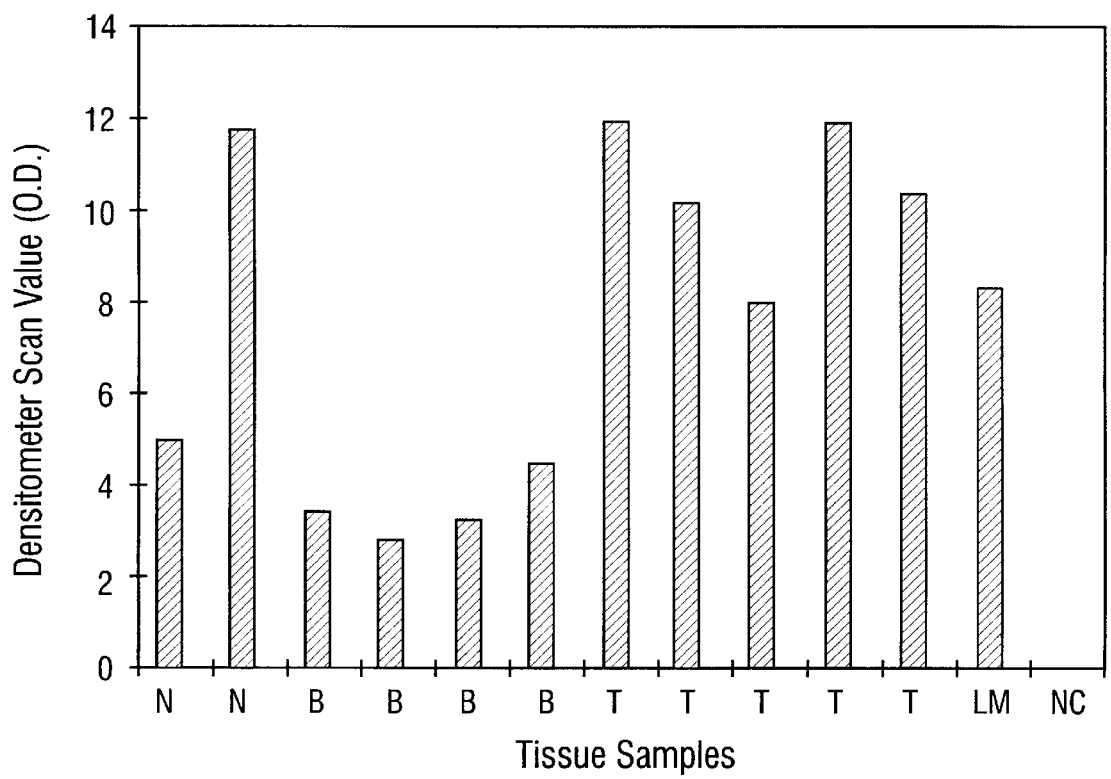
FIG. 7. Quantitative RT-PCR of TGF-$\beta$1 shows that it is overexpressed in prostate cancer compared to benign prostatic hyperplasia. N=normal prostate, B=benign prostatic hyperplasia (BPH), NB=needle core biopsy of prostate cancer, T=primary prostate cancer, LM=metastatic lymph node prostate cancer, NC=negative control.
Figure 8:
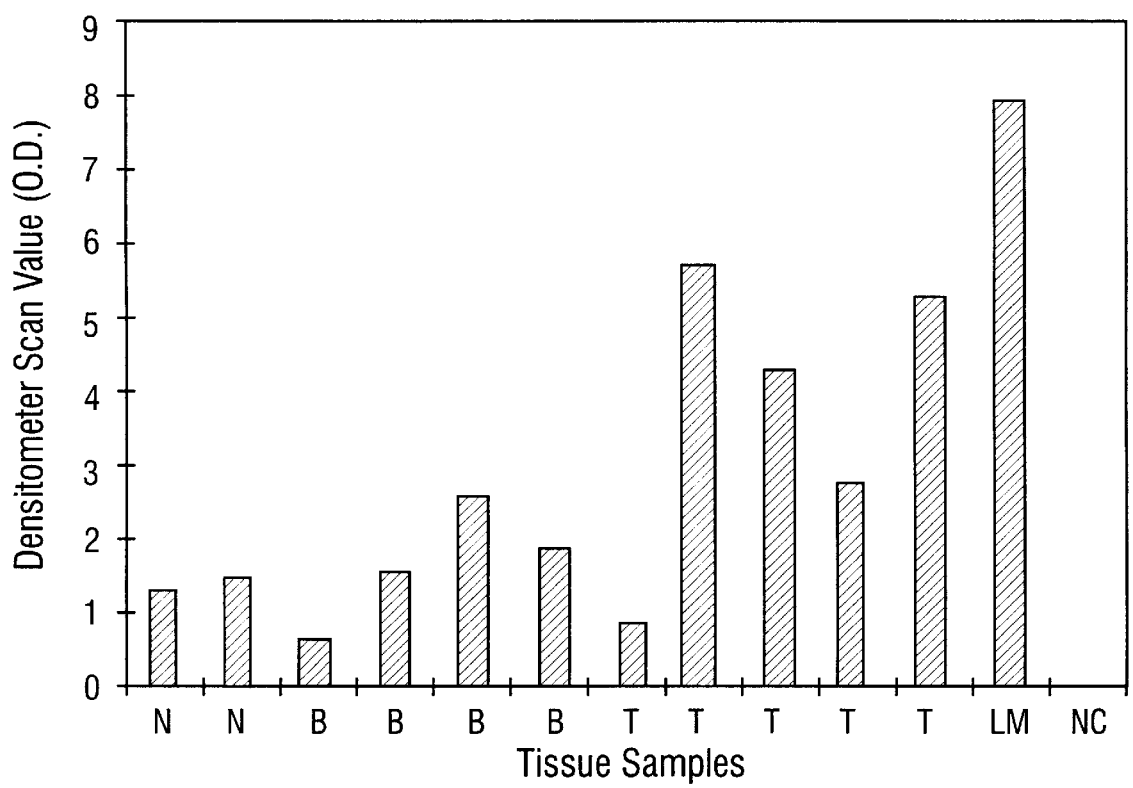
FIG. 8. Quantitative RT-PCR of Cyclin A (SEQ ID NO:8) shows that it is overexpressed in prostate cancer compared to normal prostate and benign prostatic hyperplasia. N=normal prostate, B=benign prostatic hyperplasia (BPH), NB=needle core biopsy of prostate cancer, T=primary prostate cancer, LM=metastatic lymph node prostate cancer, NC=negative control.

The results of two of these assays are included here. They show that TGF-β1 (FIG. 7) and cyclin A (FIG. 8) are both up regulated in prostate cancer relative to normal and benign glands. The cyclin A result is particularly interesting because this protein is known to be a positive regulator of cell cycle progression. It has occasionally been shown to be up regulated in some cancers, but this is the first observation of cyclin A being up regulated in most or all tumors derived from a single organ source (prostate). The sequence of cyclin A is identified as SEQ D NO:8. Those skilled in the art will recognize that the genes and gene products (RNAs and proteins), including the diagnosis and prognosis of prostatic cancer by detection of the RNA products for these two genes, are included within the scope of the invention herein described.

Figure 9A:
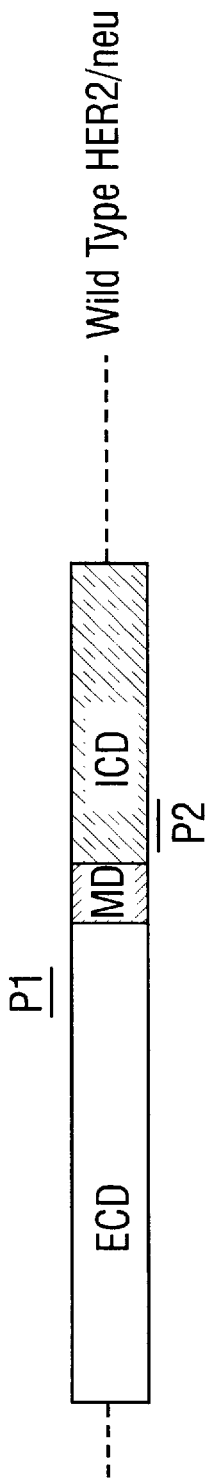
FIG. 9. Oligonucleotides used in RT-PCR investigations of Her2/neu and a truncated form of Her2neu. The binding sites for PCR primers are marked as P1 (Neu5'), P2 (Neu3') and P5 (NeuT3'). The truncated form of Her2/neu also contains the P1 binding site. The regions within the Her2/neu coding sequence are: ECD (extracellular domain), MD (membrane domain), and ICD (intracellular domain).
Figure 9B:
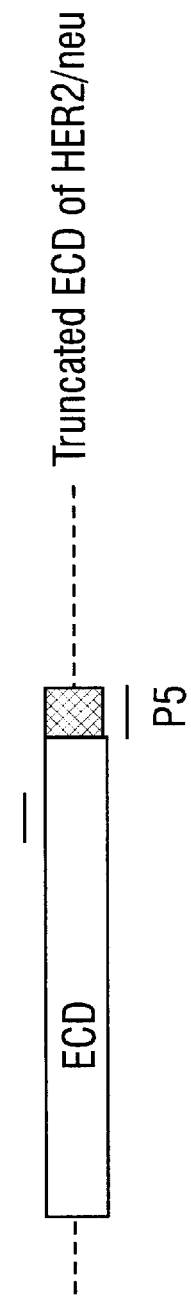

Example 4
Identification of Markers of prostate disease Using Probes Specific for a Truncated Form of Her2/neu In the studies described below, a relative quantitative version of RT-PCR was performed. The oligonucleotides used as primers to direct the amplification by PCR of the various cDNA fragments are given in Table 3. Briefly, three oligonucleotide primers were designed, which are identified in Table 3 as Neu5', SEQ ID NO:44; Neu3', SEQ ID NO:71; and NeuT3', SEQ ID NO:72. Neu5' anneals to antisense sequence for both the full length and truncated form of the Her2/neu mRNAs at a position 5' of an alternate RNA processing site (see FIG. 9). Neu3' anneals to the sense strand of the full length Her2/neu mRNA at a position just 3' of the transmembrane domain (FIG. 9).

In an RT-PCR assay using Neu5' and Neu3' as primers, a 350 base pair long amplification product was generated using the fill length mRNA as a template. Using these primers, a cDNA fragment can not be generated from the truncated mRNA because Neu3' will not anneal to this mRNA or its cDNA. The third oligonucleotide primer, NeuT3', anneals to the sense strand of the 3' untranslated region of the truncated form of the Her2/neu mRNA and cDNA (FIG. 9). In an RT-PCR assay using Neu5' and NeuT3' as primers, a 180 base pair long cDNA fragment was amplified using the truncated mRNA as a template. This primer pair can not direct the amplification of a fragment of the fill length Her2/neu mRNA because NeuT3' will not anneal to the full length transcript.

Figure 10:
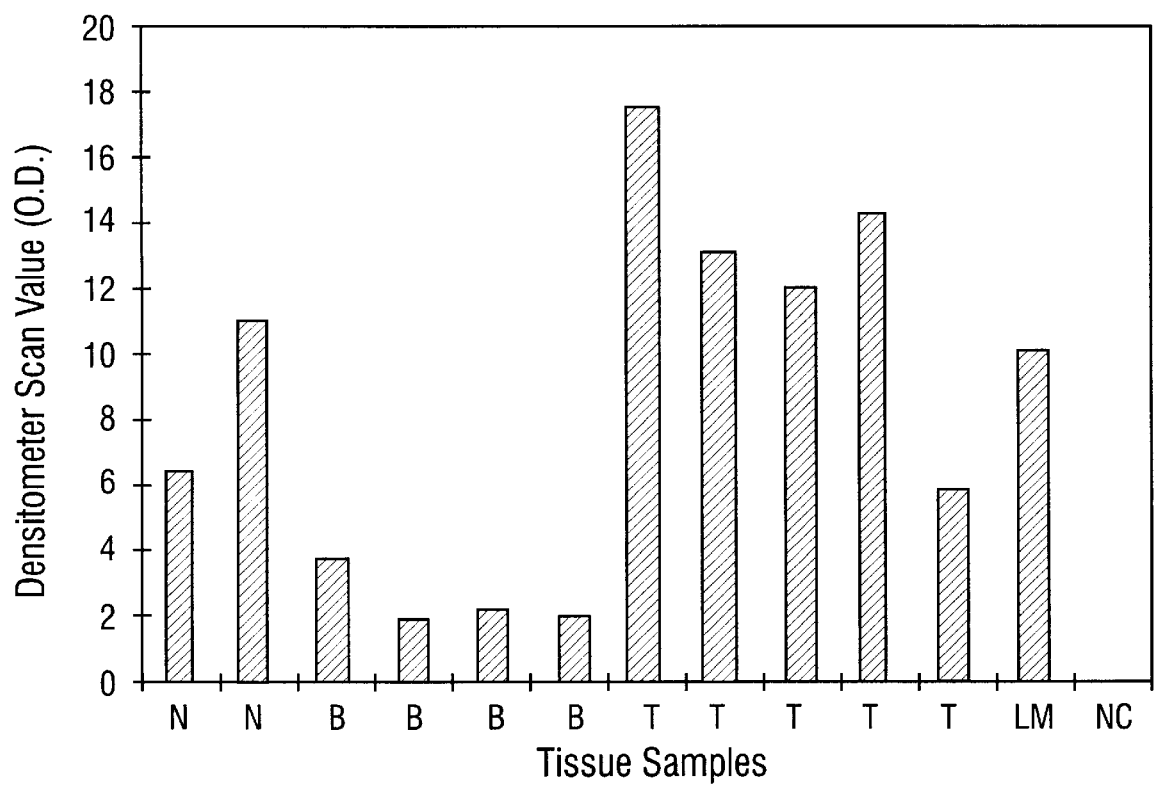
FIG. 10. Normalized quantitative RT-PCR for the full length Her2/neu transcript shows that it is overexpressed in prostate cancers compared to normal prostate and benign prostatic hyperplasia. N=normal prostate, B=benign prostatic hyperplasia (BPH), NB=needle core biopsy of prostate cancer, T=primary prostate cancer, LM=metastatic lymph node prostate cancer, NC=negative control.

The results of relative quantitative RT-PCR clearly showed that the relative abundance of the Her2/neu mRNA is increased in prostate cancers as compared to either normal prostate or benign prostatic hyperplasia (FIG. 10). These data were generated from a densitometry scan of a photographic negative of a photograph of an ethidium bromide stained gel. The raw densitometry scan data were then normalized to a similar scan of a PCR amplification from the same template of β-actin, a gene whose expression is not expected to vary as a function of transformation or tumor progression. The results are completely consistent with the increased abundance of Her2/neu protein in prostate tumors that was previously described in the literature reviewed above.

A relative quantitative RT-PCR assay examining the relative abundance of the truncated form of the Her2/neu mRNA (SEQ ID NO:9) in various prostate tissues was also performed. This assay was similar to that shown above for the fill length Her2/neu transcript. The data from this study was quantified and normalized to β-actin and is displayed in FIG. 11.

Figure 11:
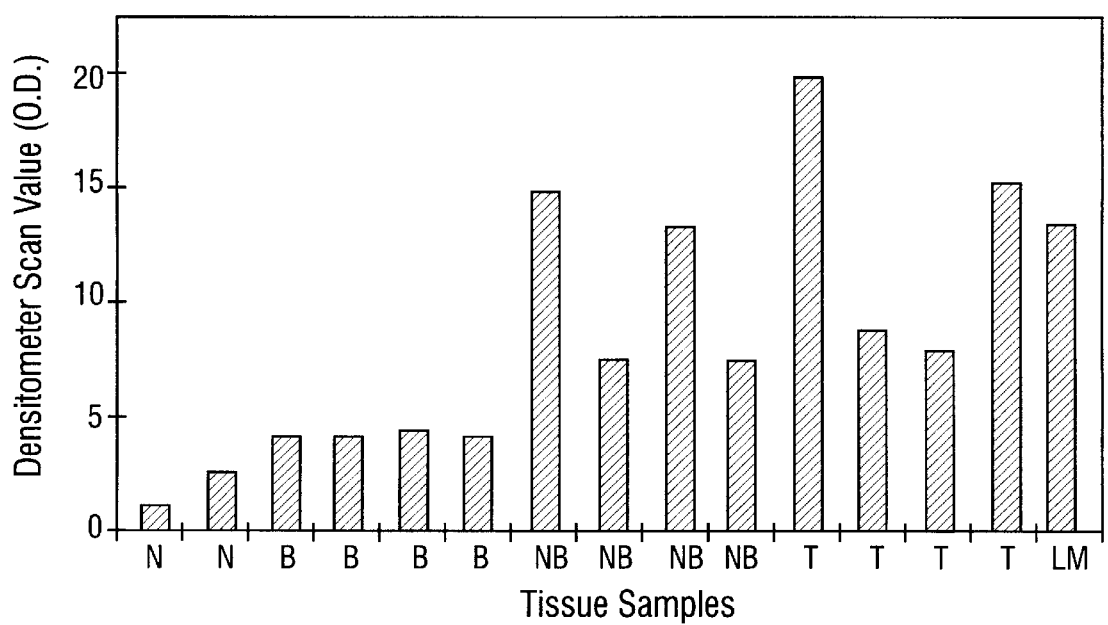
FIG. 11. Normalized quantitative RT-PCR for the truncated form of the Her2/neu transcript (SEQ ID NO:9) shows that it is overexpressed in prostate cancers compared to normal prostate and benign prostatic hyperplasia. N=normal prostate, B=benign prostatic hyperplasia (BPH), NB=needle core biopsy of prostate cancer, T=primary prostate cancer, LM=metastatic lymph node prostate cancer, NC=negative control.

As shown in FIG. 11, the relative abundance of this truncated transcript was significantly increased in prostate cancers as compared to normal and benign prostate. As discussed in a previous section, this truncated form of the Her2/neu mRNA has been previously described in breast ovarian and gastric tumors. This is the first report of differential expression of a truncated form of Her2/neu as a biomarker for prostate cancer.

As indicated in Scott et al. (1993), expression of this truncated Her2/neu mRNA may alter the cellular behavior of cancer cells to the detriment of patients. Those skilled in the art will recognize that therapeutic treatment of prostate cancer targeted towards the gene products (including mRNAs and proteins) of the truncated form of Her2/neu is included within the scope of this invention.

TABLE 1

Genes Whose mRNAs have Abundances that Vary in Prostate Cancer Relative to Normal and Benign Glands

| Name of cDNA Fragment | Sequence Determined | Confirmed by RT-PCR | Previously Known | SEQ ID NO: |
|---|---|---|---|---|
| UC Band #4-2 | Yes | Yes | α6-integrin | 6 |
| UC Band #25 | Yes | Yes | No | 1 |
| UC Band #27 | Yes | Yes | No | 2 |
| UC Band #28 | Yes | Yes | No | 3 |
| UC Band #31 | Yes | Yes | No | 4 |
| UC Band #32 | Yes | Yes | fibronectin | 7 |
| US Band #33 | Yes | Yes | No | 5 |
| Cyclin A | Yes | Yes | Cyclin A | 8 |
| Trunc. HER2/neu | Yes | Yes | Tru. HER2/neu | 9 |
| UC Band #38 | Yes | Yes | No | 10 |
| UC Band #40 | Yes | Yes | No | 11 |
| UC Band #41 | Yes | Yes | No | 12 |
| UC Band #42 | Yes | Yes. | No | 18 |
| UC Band #43 | Yes | Yes | No | 19 |
| UC Band #47 | Yes | Yes | Prostatic Acid Phosphatase | 47 |
| UC Band #201 | Yes | Yes | No | 13 |
| UC Band #204 | Yes | Yes | GB #Z28521 and GB #D42055 | 20 |
| UC Band #205 | Yes | Yes | Humhek | 14 |
| UC Band #207 | Yes | Yes | No | 15 |
| UC Band #209 | Yes | Yes | No | 16 |
| UC Band #210 | Yes | Yes | No | 17 |
| UC Band #211 | Yes | Yes | No | 21 |
| UC Band #212 | Yes | Yes | No | 22 |
| UC Band #213 | Yes | Yes | GB #T07736 | 23 |
| UC Band #214 | Yes | Yes | No | 45 |
| UC Band #215 | Yes | Yes | No | 46 |

TABLE 2

Oligonucleotides used in the relative quantitative RT-PCR portion of these studies.
Oligonucleotides used to examine the expression of genes:

UC Band #4-2 (α6 integrin) (SEQ D NO:6).

5' GGTCCGGATCCTTCAACTTGGACACTCGGGA 3', SEQ ID NO:24
5' ATCCTGAGATTCTGACTCAGGACA 3', SEQ ID NO:25
Cyclin A (SEQ ID NO:8)

5' TGCGTTCACCATTCATGTGGATGAAGCAG 3', SEQ ID NO:26
5' CTCCTACTTCAACTAACCAGTCCACGAG 3', SEQ ID NO:27
UC Band #25 (SEQ ID NO:1)

5' GATGCTTTGAAGTTATCTCTCTTGG 3', SEQ ID NO:28
5' ATCAGTGTGGCAGATATAATGGACC 3', SEQ ID NO:29
UC Band #27 (SEQ ID NO:2)

5' GCCCCAAATGCCAGGCTGCACTGAT 3', SEQ ID NO:30
5' GCCAGAAGACAAGAGTGTGAGCCTT 3', SEQ ID NO:31
UC Band #28 (SEQ ID NO:3)

5' GCTTCAGGGTGGTCCAATTAGAGTT 3', SEQ ID NO:32
5' TCCAACAACGACACATTCAGGAGTT 3', SEQ ID NO:33
UC Band #31 (SEQ ID NO:4)

5' GGACACAGAGTAAGATACCCACTGA 3', SEQ ID NO:34
5' CCTCGGTCTTTGGTCTTTGCATATC 3', SEQ ID NO:35
UC Band #32 (SEQ ID NO:7)

5' ACAAGGAAAGTGTCCCTATCTCTGA 3', SEQ ID NO:36
5' CTCGAGGTCTCCCACTGAAGTGCTC 3', SEQ ID NO:37
UC Band #33 (SEQ ID NO:5)

5'CACTGCACATTAAGATGGAGCCCGA 3', SEQ ID NO:38
5'CCTGTAGAAGTTCTGCTGCGTGTGG 3', SEQ ID NO:39

TABLE 2-continued

Oligonucleotides used in the relative quantitative RT-PCR portion of these studies.
Oligonucleotides used to examine the expression of genes:

UC Band #38 (SEQ ID NO:10)

5' TCGCTCCACATTCATCCTTTCT 3', SEQ ID NO:49
5' TGATCCCTGGGTGATATAGAGCATA 3', SEQ ID NO:50
UC Band #40 (SEQ ID NO:11)

5' GCCCCACATCTGAACAAGCTAATAA 3', SEQ ID NO:51
5' TGCGCCCTTCATACAGGCAGAGTTG 3', SEQ ID NO:52
UC Band #41 (SEQ ID NO:12)

5' CACGATGCCATTCTGCCATTTCTGT 3', SEQ ID NO:53
5' GGAAGAGATGGAATAGAAACTGTAA 3', SEQ ID NO:54
UC Band #42 (SEQ ID NO:18)

5' GGGACAGAAGGTGAGGGATGG 3', SEQ ID NO:55
5' AGACGGGATCTGGATTCAGTGAGAG 3', SEQ ID NO:56
UC Band #43 (SEQ ID NO:19)

5' CACTGGAACCAACAGGCCTGCCTCAAC 3', SEQ ID NO:57
5' CCGAGCCAATTGGTACAGGTCTGTTCTCCC 3', SEQ ID NO:58
UC Band #47 (SEQ ID NO:47)

5' CCTCAAGACTGGTCCACGGAGTGTATGA 3', SEQ ID NO:59
5' GGGTAATGGCCAAAGTATGTTCTCAAAGCA 3', SEQ ID NO:60
UC Band #201 (SEQ ID NO:13)

5' AAACAAACGTCTTTGGGTAAA 3', SEQ ID NO:61
5' CTGGACAAAGAGGAATATGA 3', SEQ ID NO:62
UC Band #204 (SEQ ID NO:20)

5' GCCCTTTATAAATACGATTAGTATGGAG 3', SEQ ID NO:63
5' TGTAGTTAGTGCAGCAAAAGGAAGA 3', SEQ ID NO:137
UC Band #205 (Humhek) (SEQ ID NO:14)

5' GATGTAATTAAAGCTGTAGATGAGGG 3', SEQ ID NO:65
5' GAATACTAACAATCTGCTCAAACTTGGG 3', SEQ ID NO:66
UC Band #207 (SEQ ID NO:15)

5' GCCAAATGGGTAGCATTGTTGCTCGG 3', SEQ ID NO:67
5' CAGAGTGGGGCAAGATACCCTTGAG 3', SEQ ID NO:68
UC Band #209 (SEQ ID NO:16)

5' AATGGAATTTCTTATGCCCTC 3', SEQ ID NO:69
5' CAATGCCAAGCACCCACTGATTC 3', SEQ ID NO:70
UC Band #210 (SEQ IDNO:17)

5' ACACAGACACACACATGCACACCA 3', SEQ ID NO:71
5' CCTACCTGTGCAGAAATCAA 3', SEQ ID NO:72
UC Band #211 (SEQ ID NO:21)

5' AGCAGCATAGCCTCTCTGAAACTC 3', SEQ ID NO:73
5' CCTTCTCATGTAGCCTGCAACCTGCTC 3', SEQ ID NO:74
UC Band #212 (SEQ ID NO:22)

5' CATTGGTGCAGCAGGTTTAGATGG 3', SEQ ID NO:75
5' GAGATATCAATTTATAAGCACCAAG 3', SEQ ID NO:76
UC Band #213 (SEQ ID NO:23)

5' ATCTCAATCATTGAGCCTGAAGG 3', SEQ ID NO:77
5' CAGCAGGTTGAGTGAGGGATTTGG 3', SEQ ID NO:78
Controls used to normalize relative quantitative RT-PCR β-actin 5' CGAGCTGCCTGACGGCCAGGTCATC 3', SEQ ID NO:40
5' GAAGCATTTGCGGTGGACGATGGAG 3', SEQ ID NO:41
Asparagine Synthetase (AS)

5' ACATTGAAGCACTCCGCGAC 3', SEQ ID NO:42
5' AGAGTGGCAGCAACCAAGCT 3', SEQ ID NO:43

TABLE 3

Oligonucleotide used for detection of the truncated Her2/neu mRNA.

NEUT3'

5" CCCCTTTTATAGTAAGAGCCCCAGA 3', SEQ ID NO:44

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention.

More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text.

Antibodies: A Laboratory Manual, Cold Spring Harbor Laboratory, Cold Spring Harbor Press, Cold Spring Harbor, N.Y., 1988.
Abbondanzo et al., *Breast Cancer Res. Treat.*, 16:182(#151), 1990.
Alcaraz et al., *Cancer Res.*, 55:3998–4002, 1994.
Allred et al., *Breast Cancer Res. Treat.*, 16:182(#149), 1990.
An et al., *Proc. Amer. Assn. Canc. Res.*, 36:82, 1995.
Bellus, *J. Macromol. Sci. Pure Appl. Chem.*, A31(1):1355–1376, 1994.
Bittner et al., *Methods in Enzymol.*, 153:516–544, 1987.
Bookstein et al., *Science*, 247:712–715, 1990a.
Bookstein et al., *Proc. Nat'l Acad. Sci. USA*, 87:7762–7767, 1990b.
Boring et al., *CA-Cancer J. Pract.*, 43:7–26, 1993.
Bova et al., *Cancer Res.*, 53:3869–3873, 1993.
Brown et al., *Breast Cancer Res. Treat.*, 16:192(#191), 1990.
Campbell, In: *Monoclonal Antibody Technology, Laboratory Techniques in Biochemistry and Molecular Biology*, Burden and Von Knippenberg, Eds., Vol. 13:75–83, Elsevier, Amsterdam, 1984.
Capaldi et al., *Biochem. Biophys. Res. Comm.*, 76:425, 1977.
Carter et al., *Proc. Nat'l Acad. Sci. USA*, 87:8751–8755, 1990.
Carter and Coffey, In: *Prostate Cancer: The Second Tokyo Symposium*, J. P. Karr and H. Yamanak (eds.), pp. 19–27, New York: Elsevier, 1989.
Carter and Coffey, *Prostate*, 16:39–48, 1990.
Chen et al., *Proc. Am. Urol. Assn.*, 153:267A, 1995.
Chinault and Carbon, *Gene*, 5:111–126, 1979.
Chomczynski and Sacchi, *Anal. Biochem.*, 162:156–159, 1987.
Colberre-Garapin et al., *J. Mol. Biol.*, 150:1, 1981.
Davey et al., EPO No. 329 822.
Dbom, *J. Cancer Res. Clin. Oncol.*, 106:210–218, 1983.
Diamond et al., *J. Urol.*, 128:729–734, 1982.
Donahue et al., *J. Biol. Chem.*, 269:8604–8609, 1994.
Dumont et al., *J. Immunol.*, 152:992–1003, 1994.
Freifelder, Physical Biochemistry Applications to Biochemistry and Molecular Biology, 2nd ed., Wm. Freeman and Co., New York, N.Y., 1982.
Frohlich et al., *Molec. Cell. Biol.*, 10:3216–3223, 1990.
Frohman, PCR PROTOCOLS: A GUIDE TO METHODS AND APPLICATIONS, Academic Press, N.Y., 1990.
Gefter et al., *Somatic Cell Genet.*, 3:231–236, 1977.
Gingeras et al., PCT Application WO 88/10315.
Goding, In: *Monoclonal Antibodies: Principles and Practice*, 2d ed., Orlando, Fla., Academic Press, pp. 60–61, 65–66, 71–74, 1986.
Hess et al., *J. Adv. Enzyme Reg.*, 7:149, 1968.
Hitzeman et al., *J. Biol. Chem.*, 255:2073, 1980.
Holland et al., *Biochemistry*, 17:4900, 1978.
Innis et al., PCR Protocols, Academic Press, Inc., San Diego Calif., 1990.
Inouye et al., *Nucleic Acids Res.*, 13:3101–3109, 1985.
Isaacs et al., *Seminars in Oncology*, 21:1–18, 1994.
Isaacs et al., *Cancer Res.*, 51:4716–4720, 1991.
Johnson et al., In: BIOTECHNOLOGY AND PHARMACY, Pezzuto et al., Eds., Chapman and Hall, New York, 1993.
Jones, *Genetics*, 85:12, 1977.
Kingsman et al., *Gene*, 7: 141, 1979.
Kohler and Milstein, *Nature*, 256:495–497, 1975.
Kohler and Milstein, *Eur. J. Immunol.*, 6:511–519, 1976.
Kwoh et al., *Proc. Nat. Acad. Sci. USA*, 86:1173, 1989.
Liang and Pardee, *Science*, 257:967–971, 1992.
Liang and Pardee, U.S. Pat. No. 5,262,311, 1993.
Liang et al., *Cancer Res.*, 52:6966–6968, 1992.
Lowy et al., *Cell*, 22:817, 1980.
Macoska et al., *Cancer Res.*, 54:3824–3830, 1994.
Miller et al., PCT Application WO 89/06700.
Mok et al., *Gynecol. Oncol.*, 52:247–252, 1994.
Morton et al., *Cancer*, 71:3737–3743, 1993.
Morton et al., *Cancer Res.*, 53:3585–3590, 1993.
Morton et al., In: CANCER MEDICINE (3rd Ed.), Holland, J. F., Frei III, E., Bast Jr., C. C. (eds), Lea and Febiger, Philadelphia, Pa., pp. 1793–1824, 1993.
Mulligan et al., *Proc. Nat'l Acad. Sci. USA*, 78:2072, 1981.
Nakamura et al., In: *Handbook of Experimental Immunology* (4th Ed.), Weir, E., Herzenberg, L. A, Blackwell, C., Herzenberg, L. (eds), Vol. 1, Chapter 27, Blackwell Scientific Publ., Oxford, 1987.
O'Hare et al., *Proc. Nat'l Acad. Sci. USA*, 78:1527, 1981.
Ohara et al., *Proc. Nat'l Acad. Sci. USA*, 86:5673–5677, 1989.
Partin et al., *Cancer Res.*, 53:744–746, 1993.
Pearsons et al., *J. Urol.*, 150:120–125, 1993.
Qiao et al., *Biochem. Biophys. Res. Comm.*, 201:581–588, 1994.
Ribas de Pouplana and Fothergill-Gilmore, *Biochemistry*, 33:7047–7055, 1994.
Rieber, M. and Rieber, M. S., *Cell Growth Diff.*, 5:1339–1346, 1994.
Sager et al., *FASEB J.*, 7:964–970, 1993.
Sambrook et al., (ed.), MOLECULAR CLONING, Cold Spring Harbor Laboratory Press, Cold Spring Harbor, N.Y., 1989.
Scott et al., *Molec. Cell. Biol.*, 13:2247–2257, 1993.
Slamon et al., *Science*, 224:256–262, 1984.
Smith, U.S. Pat. No. 4,215,051.
Stinchcomb et al., *Nature*, 282:39, 1979.
Sun and Cohen, *Gene*, 137:127–132, 1993.
Szybalska et al., *Proc. Nat'l Acad. Sci. USA*, 48:2026, 1962.
Takahashi et al., *Cancer Res.*, 54:3574–3579, 1994.
Tschemper et al., *Gene*, 10:157, 1980.
Umbas et al., *Cancer Res.*, 52:5104–5109, 1992.

Visakorpi et al., *Am. J. Pathol.,* 145:1–7, 1994.
Vishwanatha et al., *Carcinogenesis,* 14:2575–2579, 1993.
Walker et al., *Proc. Nat'l Acad. Sci. USA,* 89:392–396, 1992.
Watson et al., *Cancer Res.,* 54:4598–4602, 1994.
Webb and Lin, *Invest. Urol.,* 17:401–404, 1980.
Welsh et al., *Nucleic Acids Res.,* 20:4965–4970, 1992.
Welsh and McClelland, *Nucl. Acids. Res.,* 18:7213–7218, 1990.
Wiger et al., *Cell,* 11:223, 1977.
Wigler et al., *Proc. Nat'l Acad. Sci. USA,* 77:3567, 1980.
Wong et al., *Int. J. Oncol.,* 3:13–17, 1993.
Wu et al., *Genomics,* 4:560, 1989.

---

We claim:

1. A method for detecting prostate cancer or benign prostatic hyperplasia cells in a biological sample comprising:

a) providing nucleic acids from said sample;

b) amplifying said nucleic acids to form nucleic acid amplification products;

c) contacting said nucleic acid amplification products with an oligonucleotide probe that will hybridize under stringent conditions with an isolated nucleic acid having a sequence selected from a group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:23, SEQ ID NO:45 and SEQ ID NO:46;

d) detecting the nucleic acid amplification products which hybridize with said probe; and e) quantifying the amount of said nucleic acid amplification products that hybridize with said probe.

2. The method of claim 1, in which the sequence of said oligonucleotide probe is selected to bind specifically to a nucleic acid product of a known gene, said nucleic acid product selected from a group consisting of human Hek, cyclin A, fibronectin, and a truncated form of Her2/neu.

3. The method of claim 2, in which the sequence of said oligonucleotide probe is selected to bind specifically to a truncated nucleic acid product of the Her2/neu gene.

4. The method of claim 2, in which the sequence of said oligonucleotide probe is selected to bind specifically to a nucleic acid product of the cyclin A gene.

5. The method of claim 2, in which the sequence of said oligonucleotide probe is selected to bind specifically to a nucleic acid product of the fibronectin gene.

6. The method of claim 2, in which the sequence of said oligonucleotide probe is selected to bind specifically to a nucleic acid product of the human Hek gene.

7. A method for detecting prostate cancer or benign prostatic hyperplasia cells in a biological sample comprising:

a) providing nucleic acids from said sample;
  b) providing primers that will selectively amplify an isolated nucleic acid having a sequence selected from a group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:23, SEQ ID NO:45 and SEQ ID NO:46;
  c) amplifying said nucleic acids with said primers to form nucleic acid amplification products;
  d) detecting said nucleic acid amplification products; and
  e) quantifying the amounts of said nucleic acid amplification products formed.

8. The method of claim 7, in which said primers are selected to amplify a nucleic acid product of a known gene, said nucleic acid product selected from a group consisting of human Hek, cyclin A, fibronectin, and a truncated form of Her2/neu.

9. The method of claim 7 in which said primers are selected to amplify a truncated nucleic acid product of the Her2/neu gene.

10. The method of claim 7 in which said primers are selected to amplify a nucleic acid product of the cyclin A gene.

11. The method of claim 7 in which said primers are selected to amplify a nucleic acid product of the fibronectin gene.

12. The method of claim 7 in which said primers are selected to amplify a human Hek gene.

13. The method of claim 1, further comprising determining the prognosis of prostate cancer patients by quantifying the amount of nucleic acid amplification product binding to said probe.

14. The method of claim 1, further comprising determining the diagnosis of human prostate cancer by quantifying the amount of said nucleic acid amplification product binding to said probe.

15. The method of claim 7, further comprising determining the prognosis of prostate cancer patients by quantifying the amount of nucleic acid amplification products formed.

16. The method of claim 7, further comprising determining the diagnosis of human prostate cancer by quantifying the amount of said nucleic acid amplification products formed.

17. The method of claim 1, wherein the sequence is SEQ ID NO:1.

18. The method of claim 1, wherein the sequence is SEQ ID NO:2.

19. The method of claim 1, wherein the sequence is SEQ ID NO:3.

20. The method of claim 1, wherein the sequence is SEQ ID NO:4.

21. The method of claim 1, wherein the sequence is SEQ ID NO:5.

22. The method of claim 1, wherein the sequence is SEQ ID NO:6.

23. The method of claim 1, wherein the sequence is SEQ ID NO:7.

24. The method of claim 1, wherein the sequence is SEQ ID NO:8.

25. The method of claim 1, wherein the sequence is SEQ ID NO:9.

26. The method of claim 1, wherein the sequence is SEQ ID NO:10.

27. The method of claim 1, wherein the sequence is SEQ ID NO:11.

28. The method of claim 1, wherein the sequence is SEQ ID NO:12.

29. The method of claim 1, wherein the sequence is SEQ ID NO:13.

30. The method of claim 1, wherein the sequence is SEQ ID NO:14.

31. The method of claim 1, wherein the sequence is SEQ ID NO:15.

32. The method of claim 1, wherein the sequence is SEQ ID NO:16.

33. The method of claim 1, wherein the sequence is SEQ ID NO:17.

34. The method of claim 1, wherein the sequence is SEQ ID NO:19.

35. The method of claim 1, wherein the sequence is SEQ ID NO:20.

36. The method of claim 1, wherein the sequence is SEQ ID NO:21.

37. The method of claim 1, wherein the sequence is SEQ ID NO:22.

38. The method of claim 1, wherein the sequence is SEQ ID NO:23.

39. The method of claim 1, wherein the sequence is SEQ ID NO:45.

40. The method of claim 1, wherein the sequence is SEQ ID NO:46.

41. The method of claim 7, wherein the sequence is SEQ ID NO:1.

42. The method of claim 7, wherein the sequence is SEQ ID NO:2.

43. The method of claim 7, wherein the sequence is SEQ ID NO:3.

44. The method of claim 7, wherein the sequence is SEQ ID NO:4.

45. The method of claim 7, wherein the sequence is SEQ ID NO:5.

46. The method of claim 7, wherein the sequence is SEQ ID NO:6.

47. The method of claim 7, wherein the sequence is SEQ ID NO:7.

48. The method of claim 7, wherein the sequence is SEQ ID NO:8.

49. The method of claim 7, wherein the sequence is SEQ ID NO:9.

50. The method of claim 7, wherein the sequence is SEQ ID NO:10.

51. The method of claim 7, wherein the sequence is SEQ ID NO:11.

52. The method of claim 7, wherein the sequence is SEQ ID NO:12.

53. The method of claim 7, wherein the sequence is SEQ ID NO:13.

54. The method of claim 7, wherein the sequence is SEQ ID NO:14.

55. The method of claim 7, wherein the sequence is SEQ ID NO:15.

56. The method of claim 7, wherein the sequence is SEQ ID NO:16.

57. The method of claim 7, wherein the sequence is SEQ ID NO:17.

58. The method of claim 7, wherein the sequence is SEQ ID NO:19.

59. The method of claim 7, wherein the sequence is SEQ ID NO:20.

60. The method of claim 7, wherein the sequence is SEQ ID NO:21.

61. The method of claim 7, wherein the sequence is SEQ ID NO:22.

62. The method of claim 7, wherein the sequence is SEQ ID NO:23.

63. The method of claim 7, wherein the sequence is SEQ ID NO:45.

64. The method of claim 7, wherein the sequence is SEQ ID NO:46.

\* \* \* \* \*

SEQUENCE LISTING ( 1 ) GENERAL INFORMATION:

( i i i ) NUMBER OF SEQUENCES: 82

( 2 ) INFORMATION FOR SEQ ID NO: 1:

( i ) SEQUENCE CHARACTERISTICS:
        ( A ) LENGTH: 391 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GTCCAGTCGC  TCAGAAATTT  CCTTTGATGC  TTTGAAGTTA  TCTCTCTTGG  ATCTGCTTCC        60

TCCTTATCGT  CTCTACATCC  CAAGAACAGA  GAGTGAGTCT  TCTTTATTTT  CTTATCTCTG       120

TTTTTAGCAC  AGTATTTGAT  ATATAGTGTA  GATACTATAA  ATGCTTGCTA  AACTTTGTCA       180

AATTCCACAT  TTTTAAAATA  AAAATGAGAA  TGAGCTTGTA  GTCAACATGG  CGTTTGTAAG       240

TTTGGAGTCT  ATATATGGTA  GATATACATA  TTTTTAAATC  TAAGTGCAAC  TTTTCTCTTG       300

ATTATCTTGA  AATGCCTTAT  CATCTCCACA  TTTGCTGTAG  GCAGTAGTTT  AGTGGGTCCA       360

TTATATCTGC  CACACTGATT  GTCTTAAATA  A                                       391
```

( 2 ) INFORMATION FOR SEQ ID NO: 2:

( i ) SEQUENCE CHARACTERISTICS:
        ( A ) LENGTH: 614 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
CAGTAGTGGC  CCCAAATGCC  AGGCTGCACT  GATATTTATT  GGATATAAGA  CAAAGGGGCA        60

GGGTAAGGAA  TGTGAACCAT  CTCCAATAAT  AGGTAAGGTC  ACATGGGTCA  TGTGTCCACT       120

GGACAGGGGG  CCCTTCCCTG  CCTGGCAGCA  GAGGCAGAGA  GAGAGAGAAG  AGAGAGAGAC       180

AGCTTATGCC  ATTATTTCTG  CATATCAGAC  ATTTAGTACT  TTCACTAATT  TGCTCCTGCT       240

ATCTAAAAGG  CAGAGCCAGG  TATACAGGAT  GGAACATGAA  AGCGGACTAG  GAGCGTGACC       300

ACTGAAGCAC  AGCATCACAG  GGAGACAGGC  CTCTGGATAC  TGGCCGGGGG  GCCCTGACTG       360

ATGTCAAGGC  CCTCCACAAG  AGTGGAGGAG  TTAGTCTTCC  TCTAAACTCC  CCCGGGGAA        420

AGGGAGGCTC  CTTTTCCCAG  TCTGCTAAGT  AGTGGGTGTT  TTTCCTTGAC  ACTGATGCTA       480

CTGCTAGACC  ATGGTCCACT  TTGCAACAGG  CATCTTCCCA  GACACTGGTG  TTACTGCTAG       540

ACCAAGCCCT  CTGGTGGCCC  TGTCCGGGCA  TAAGAGAAGG  CTCACACTCT  TGTCTTCTGG       600

CCACTTCGCA  CTAT                                                            614
```

( 2 ) INFORMATION FOR SEQ ID NO: 3:

( i ) SEQUENCE CHARACTERISTICS:
        ( A ) LENGTH: 757 base pairs
        ( B ) TYPE: nucleic acid
        ( C ) STRANDEDNESS: single (D) TOPOLOGY: linear (xi) SEQUENCE DESCRIPTION: SEQ ID NO: 3:

| | | | | | | |
|---|---|---|---|---|---|---|
| ACAACGACAC | ATTCAGGAGT | TAAATATTTA | TCATCAAACA | TTGGATTTTT | CCTTAACGCT | 60 |
| AGAGATTGCT | ACAAATCTTC | TGAAGGGTCT | CAATGGCTTC | AGGCTAAGAA | GAGATTTCTC | 120 |
| CCTGTTATAA | GCAGCAAGAC | AAATTAGCCA | TTTCACTCTC | AAACTTCACT | AATGATCACA | 180 |
| TTCTTTCCAA | AAGGAACTCT | AGAAGACCAA | ATGCCCCGAG | TTAAGAACAT | CAAAACTAAC | 240 |
| CATCTGAAGA | AACTTCCCAA | GTGTAAGACT | CTGCCATTAA | AACATTACCG | AGAGGGGACT | 300 |
| CAAACAGTCT | TTTCTTCCCT | TTGTCGTGTT | TCTTTGCTCC | CAGACCCAAG | GCACTTGGCG | 360 |
| GACAGTACTT | GATACAATAA | TTTAAAAAGC | ACCACTCCCT | TCCCACTTTG | TAAATACCCA | 420 |
| GAACTCTAAT | TGGACCACCC | TGAAGCTTAG | GACCTACCAG | CCATACAAAT | AGTAAACTCT | 480 |
| GTCCACGATT | CACTCATCTG | TGTATTTTCT | ATAGATGTTT | ACTAGGCGTT | TGTTATATAA | 540 |
| AAATACCCCG | GCCAGGCACG | GTGGCTCACG | CCTGTAATCC | CAGCACTTTG | GGAGGTGGGT | 600 |
| GGATCACCTG | AGGTCGGGAG | TTCGAGACCA | GCCTGACCAG | CATGGTGGAA | CCCCCATCTC | 660 |
| TACTAAAAAC | ACAAAAAATT | AGCCGGGCGT | GGTGGCACAT | GCCTGTAATC | CCAGCTACTC | 720 |
| AGGAGGCTGA | GGCGGAGAAT | TGCTTGAACC | CGGAAGG | | | 757 |

(2) INFORMATION FOR SEQ ID NO: 4:

(i) SEQUENCE CHARACTERISTICS:
(A) LENGTH: 673 base pairs
(B) TYPE: nucleic acid
(C) STRANDEDNESS: single
(D) TOPOLOGY: linear (xi) SEQUENCE DESCRIPTION: SEQ ID NO: 4:

| | | | | | | |
|---|---|---|---|---|---|---|
| CAGGACACAG | AGTAAGATAC | CCACTGACTT | CTTGTGGTCT | ACTTCCTGGG | TGTTGTTTCA | 60 |
| ATGGGCTTTG | TTATAACAGG | ACTAGTCTTC | TGTAAATACA | ACTTGGTAAA | TAGGATGAAA | 120 |
| CATAACTTTG | CGACAATTCA | GTAGAAATAG | GCATACAAAC | CTGGGCCTGA | TGACACTCAC | 180 |
| CTCCCCTTGG | CTATAAACAT | TACCCTACCT | GTTAAGTCAG | TAATCCTTTG | GGAGAGCGCT | 240 |
| TACTGAGTAT | CTATGATATG | CAAAGACCAA | AGACCGAGGG | GGATCCCTGG | TGTAGAGCAA | 300 |
| GCACACACCT | GGTTATTAGC | TACCTGCCAC | CCTGCTGGGC | ATGCAACATA | CATTGTCTCA | 360 |
| AATTCTAACC | ACCCTGCAAG | GCAAGCTTCC | TTGTTCTTTT | AAAGAAGAAA | AGTAGACCAG | 420 |
| CAAGATTGAT | TTGCTCAAGA | TTACACAGCC | TGGAATCTTG | TCATGGGCAT | GTCTGACTCT | 480 |
| GATAGCAATA | CCCTCAAAGA | AACTGTCAGA | GAAGACTCAA | TAAGAAGAAA | GTTGAGATAC | 540 |
| AGAAACCAAC | AGGAGAAGGT | AATTCAGAAA | TTCAAACAGA | GTGGGTGTGA | TGGGAAGAAT | 600 |
| TCATTAATAA | GAAGGTACCT | CTGTAGAAAA | ATCTTACCAG | ACAGTCTGGA | AGTGAAGGAA | 660 |
| ACAGCCAATA | GTC | | | | | 673 |

(2) INFORMATION FOR SEQ ID NO: 5:

(i) SEQUENCE CHARACTERISTICS:
(A) LENGTH: 358 base pairs
(B) TYPE: nucleic acid
(C) STRANDEDNESS: single
(D) TOPOLOGY: linear (xi) SEQUENCE DESCRIPTION: SEQ ID NO: 5:

| | | | | | | |
|---|---|---|---|---|---|---|
| GTCACTGCAC | ATTAAGATGG | AGCCCGAAGA | GCCACACTCC | GAGGGGGCAT | CGCAGGAGGA | 60 |
| TGGGGCTCAA | GGTGCCTGGG | GCTGGGCACC | CCTAAGTCAC | GGCTCTAAGG | AGAAAGCTCT | 120 |

| | | | | | | |
|---|---|---|---|---|---|---|
| CTTCCTGCCC | GGCGGAGCCC | TCCCCTCCCC | CCGGATCCCC | GTGCTTTCCC | GAGAGGGGAG | 180 |
| GACCAGAGAC | CGGCAGATGG | CTGCAGCGCT | CCTCACTGCC | TGGTCCCAGA | TGCCAGTGAC | 240 |
| TTTCGAGGAT | GTGGCCTTGT | ACCTCTCCCG | GGAGGAGTGG | GGACGGCTGG | ACCACACGCA | 300 |
| GCAGAACTTC | TACAGGGAAT | GTCCTGCAGA | AGAAAAATGG | GCTGTCACTG | GGCTTTCC | 358 |

( 2 ) INFORMATION FOR SEQ ID NO: 6:

( i ) SEQUENCE CHARACTERISTICS:
        ( A ) LENGTH: 1450 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

| | | | | | | |
|---|---|---|---|---|---|---|
| ATTTGGTTTT | AAGTACAACT | GAAGTCACCT | TTGACACCCC | ATATCTGGAT | ATTAATCTGA | 60 |
| AGTTAGAAAC | AACAAGCAAT | CAAGATAATT | TGGCTCCAAT | TACAGCTAAA | GCAAAAGTGG | 120 |
| TTATTGAACT | GCTTTTATCG | GTCTCGGGAG | TTGCTAAACC | TTCCCAGGTG | TATTTTGGAG | 180 |
| GTACAGTTGT | TGGCGAGCAA | GCTATGAAAT | CTGAAGATGA | AGTGGGAAGT | TTAATAGAGT | 240 |
| ATGAATTCAG | GGTAATAAAC | TTAGGTAAAC | CTCTTACAAA | CCTCGGCACA | GCAACCTTGA | 300 |
| ACATTCAGTG | GCCAAAGAA | ATTAGCAATG | GGAAATGGTT | GCTTTATTTG | GTGAAAGTAG | 360 |
| AATCCAAAGG | ATTGGAAAAG | GTAACTTGTG | AGCCACAAAA | GGAGATAAAC | TCCCTGAACC | 420 |
| TAACGGAGTC | TCACAACTCA | AGAAAGAAAC | GGGAAATTAC | TGAAAAACAG | ATAGATGATA | 480 |
| ACAGAAAATT | TTCTTTATTT | GCTGAAAGAA | AATACCAGAC | TCTTAACTGT | AGCGTGAACG | 540 |
| TGAACTGTGT | GAACATCAGA | TGCCCGCTGC | GGGGGCTGGA | CAGCAAGGCG | TCTCTTATTT | 600 |
| TGCGCTCGAG | GTTATGGAAC | AGCACATTTC | TAGAGGAATA | TTCCAAACTG | AACTACTTGG | 660 |
| ACATTCTCAT | GCGAGCCTTC | ATTGATGTGA | CTGCTGCTGC | CGAAAATATC | AGGCTGCCAA | 720 |
| ATGCAGGCAC | TCAGGTTCGA | GTGACTGTGT | TTCCCTCAAA | GACTGTAGCT | CAGTATTCGG | 780 |
| GAGTACCTTG | GTGGATCATC | CTAGTGGCTA | TTCTCGCTGG | GATCTTGATG | CTTGCTTTAT | 840 |
| TAGTGTTTAT | ACTATGGAAG | TGTGGTTTCT | TCAAGAGAAA | TAAGAAAGAT | CATTATGATG | 900 |
| CCACATATCA | CAAGGCTGAG | ATCCATGCTC | AGCCATCTGA | TAAAGAGAGG | CTTACTTCTG | 960 |
| ATGCATAGTA | TTGATCTACT | TCTGTAATTG | TGTGGATTCT | TTAAACGCTC | TAGGTACGAT | 1020 |
| GACAGTGTTC | CCCGATACCA | TGCTGTAAGG | ATCCGGAAAG | AAGAGCGAGA | GATCAAAGAT | 1080 |
| GAAAGTATA | TTGATAACCT | TGAAAAAAAA | CAGTGGATCA | CAAAGTGGAA | CAGAAATGAA | 1140 |
| AGCTACTCAT | AGCGGGGGCC | TAAAAAAAAA | AAAGCTTCAC | AGTACCCAAA | CTGCTTTTTC | 1200 |
| CAACTCAGAA | ATTCAATTTG | GATTTAAAAG | CCTGCTCAAT | CCCTGAGGAC | TGATTTCAGA | 1260 |
| GTGACTACAC | ACAGTACGAA | CCTACAGTTT | TAACTGTGGA | TATTGTTACG | TAGCCTAAGG | 1320 |
| CTCCTGTTTT | GCACAGCCAA | ATTTAAAACT | GTTGGAATGG | ATTTTTCTTT | AACTGCCGTA | 1380 |
| ATTTAACTTT | CTGGGTTGCC | TTTGTTTTTG | GCGTGGCTGA | CTTACATCAT | GTGTTGGGGA | 1440 |
| AGGGCCTGCC | | | | | | 1450 |

( 2 ) INFORMATION FOR SEQ ID NO: 7:

( i ) SEQUENCE CHARACTERISTICS:
        ( A ) LENGTH: 610 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

| | | | | | | |
|---|---|---|---|---|---|---|
| CTGGAGTACA | ATGTCAGTGT | TTACACTGTC | AAGGATGACA | AGGAAAGTGT | CCCTATCTCT | 60 |
| GATACCATCA | TCCCAGCTGT | TCCTCCTCCC | ACTGACCTGC | GATTCACCAA | CATTGGTCCA | 120 |
| GACACCATGC | GTGTCACCTG | GGCTCCACCC | CCATCCATTG | ATTTAACCAA | CTTCCTGGTG | 180 |
| CGTTACTCAC | CTGTGAAAAA | TGAGGAAGAT | GTTGCAGAGT | TGTCAATTTC | TCCTTCAGAC | 240 |
| AATGCAGTGG | TCTTAACAAA | TCTCCTGCCT | GGTACAGAAT | ATGTAGTGAG | TGTCTCCAGT | 300 |
| GTCTACGAAC | AACATGAGAG | CACACCTCTT | AGAGGAAGAC | AGAAACAGG | TCTTGATTCC | 360 |
| CCAACTGGCA | TTGACTTTTC | TGATATTACT | GCCAACTCTT | TTACTGTGCA | CTGGATTGCT | 420 |
| CCTCGAGCCA | CCATCACTGG | CTACAGGATC | CGCCATCATC | CCGAGCACTT | CAGTGGGAGA | 480 |
| CCTCGAGAAG | ATCGGGTGCC | CCACTCTCGG | AATTCCATCA | CCCTCACCAA | CCTCACTCCA | 540 |
| GGCACAGAGT | ATGTGGTCAG | CATCGTTGCT | CTTAATGGCA | GAGAGGAAAG | TCCCTTATTG | 600 |
| ATTGGCCAAC | | | | | | 610 |

(2) INFORMATION FOR SEQ ID NO: 8:

(i) SEQUENCE CHARACTERISTICS:
        (A) LENGTH: 1649 base pairs
        (B) TYPE: nucleic acid
        (C) STRANDEDNESS: single
        (D) TOPOLOGY: linear (xi) SEQUENCE DESCRIPTION: SEQ ID NO: 8:

| | | | | | | |
|---|---|---|---|---|---|---|
| CGGCAGCCAG | CCTATTCTTT | GGCCGGGTCG | GTGCGAGTGG | TCGGCTGGGC | AGAGTGCACG | 60 |
| CTGCTTGGCG | CCGCAGGTGA | TCCCGCCGTC | CACTCCCGGG | AGCAGTGATG | TTGGGCAACT | 120 |
| CTGCGCCGGG | GCCTGCGACC | CGCGAGGCGG | GCTCGGCGCT | GCTAGCATTG | CAGCAGACGG | 180 |
| CGCTCCAAGA | GGACCAGGAG | AATATCAACC | CGGAAAAGGC | AGCGCCCGTC | CAACAACCGC | 240 |
| GGACCCGGGC | CGCGCTGGCG | GTACTGAAGT | CCGGGACCCC | GCGGGGTCTA | GCGCAGCAGC | 300 |
| AGAGGCCGAA | GACGAGACGG | GTTGCACCCC | TTAAGGATCT | TCCTGTAAAT | GATGAGCATG | 360 |
| TCACCGTTCC | TCCTTGGAAA | GCAAACAGTA | AACAGCCTGC | GTTCACCATT | CATGTGGATG | 420 |
| AAGCAGAAAA | AGAAGCTCAG | AAGAAGCCAG | CTGAATCTCA | AAAAATAGAG | CGTGAAGATG | 480 |
| CCCTGGCTTT | TAATTCAGCC | ATTAGTTTAC | CTGGACCCAG | AAAACCATTG | GTCCCTCTTG | 540 |
| ATTATCCAAT | GGATGGTAGT | TTTGAGTCAC | CACATACTAT | GGACATGTCA | ATTGTATTAG | 600 |
| AAGATGAAAA | GCCAGTGAGT | GTTAATGAAG | TACCAGACTA | CCATGAGGAT | ATTCACACAT | 660 |
| ACCTTAGGGA | AATGGAGGTT | AAATGTAAAC | CTAAAGTGGG | TTACATGAAG | AAACAGCCAG | 720 |
| ACATCACTAA | CAGTATGAGA | GCTATCCTCG | TGGACTGGTT | AGTTGAAGTA | GGAGAAGAAT | 780 |
| ATAAACTACA | GAATGAGACC | CTGCATTTGG | CTGTGAACTA | CATTGATAGG | TTCCTGTCTT | 840 |
| CCATGTCAGT | GCTGAGAGGA | AAACTTCAGC | TTGTGGGCAC | TGCTGCTATG | CTGTTAGCCT | 900 |
| CAAAGTTTGA | AGAAATATAC | CCCCAGAAG | TAGCAGAGTT | TGTGTACATT | ACAGATGATA | 960 |
| CCTACACCAA | GAAACAAGTT | CTGAGAATGG | AGCATCTAGT | TTTGAAAGTC | CTTACTTTTG | 1020 |
| ACTTAGCTGC | TCCAACAGTA | AATCAGTTTC | TTACCCAATA | CTTTCTGCAT | CAGCAGCCTG | 1080 |
| CAAACTGCAA | AGTTGAAAGT | TTAGCAATGT | TTTTGGGAGA | ATTAAGTTTG | ATAGATGCTG | 1140 |
| ACCCATACCT | CAAGTATTTG | CCATCAGTTA | TTGCTGGAGC | TGCCTTTCAT | TTAGCACTCT | 1200 |
| ACACAGTCAC | GGGACAAAGC | TGGCCTGAAT | CATTAATACG | AAAGACTGGA | TATACCCTGG | 1260 |
| AAAGTCTTAA | GCCTTGTCTC | ATGGACCTTC | ACCAGACCTA | CCTCAAAGCA | CCACAGCATG | 1320 |
| CACAACAGTC | AATAAGAGAA | AAGTACAAAA | ATTCAAAGTA | TCATGGTGTT | TCTCTCCTCA | 1380 |
| ACCCACCAGA | GACACTAAAT | CTGTAACAAT | GAAAGACTGC | CTTTGTTTTC | TAAGATGTAA | 1440 |

```
ATCACTCAAA  GTATATGGTG  TACAGTTTTT  AACTTAGGTT  TTTAATTTTA  CAATCATTTC    1500

TGAATACAGA  AGTTGTGGCC  AAGTACAAAT  TATGGTATCT  ATTACTTTTT  AAATGGTTTT    1560

AATTTGTATA  TCTTTTGTAT  ATGTATCTGT  CTTAGATATT  TGGCTAATTT  TAAGTGGTTT    1620

TGTTAAAGTA  TTAATGATGC  CAGCTGCCG                                         1649
```

( 2 ) INFORMATION FOR SEQ ID NO: 9:

( i ) SEQUENCE CHARACTERISTICS:
        ( A ) LENGTH: 175 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

```
ACCCACTCGT  GAGTCCAACG  GTCTTTTCTG  CAGAAAGGAG  GACTTTCCTT  TCAGGGGTCT     60

TTCTGGGGCT  CTTACTATAA  AAGGGGACCA  ACTCTCCCTT  TGTCATATCT  TGTTTCTGAT    120

GACAAAAAAT  AACACATTGT  TAAAATTGTA  AAATTAAAAC  ATGAAATATA  AATTA         175
```

( 2 ) INFORMATION FOR SEQ ID NO: 10:

( i ) SEQUENCE CHARACTERISTICS:
        ( A ) LENGTH: 166 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

```
GTTTCGCTCC  ACATTCATCC  TTTCTTACTG  GGCACTGATG  TTGAGAGCAT  CAGGCAGGGT     60

ATAATGTTAT  GTTGCAGTAA  CAAACACCCT  CAATATCTCA  GTGGCTTAAA  ATGACAACGA    120

TCTTTTTTTT  GTTTGTTTGT  TTATGCTCTA  TATCACCCAG  GGATCA                    166
```

( 2 ) INFORMATION FOR SEQ ID NO: 11:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

```
TGCTCTGCCC  CACATCTGAA  CAAGCTAATA  AGAAAGCCCG  ATGTTCTTTC  CTTTGGTGCC     60

ATTGGGAAAT  TCAAACCATG  CACAACTCTG  CCTGTATGAA  GGGCGCA                   107
```

( 2 ) INFORMATION FOR SEQ ID NO: 12:

( i ) SEQUENCE CHARACTERISTICS:
        ( A ) LENGTH: 183 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

```
CAACCTTAGC  CCCTCTCCTC  TTCTTCACGA  TGCCATTCTG  CCATTTCTGT  TTTGTGGTAG     60

ACAGGTTGGC  CCAGGCACTC  TAAGGCCCAG  GCTGGCACAG  GTTGGCCCAG  GCACTTCAAG    120

CCTAAGTCCA  TTTACAGTTT  CTATTCCATC  TCTTCCTAAA  GAAGAGGAGA  GGGGCTAAGG    180

TTG                                                                       183
```

( 2 ) INFORMATION FOR SEQ ID NO: 13:

( i ) SEQUENCE CHARACTERISTICS:
    ( A ) LENGTH: 92 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 13:

```
AAACAAACGT  CTTTGGGTAA  AATTCTATTT  CTTTTAATGT  TTTAAAATAT  TTGTAGTCAC      60

TAATTGTAAG  TCATATTCCT  CTTTGTCCAG  CT                                      92
```

( 2 ) INFORMATION FOR SEQ ID NO: 14:

( i ) SEQUENCE CHARACTERISTICS:
        ( A ) LENGTH: 182 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

```
GATGTAATTA  AAGCTGTAGA  TGAGGGCTAT  CGACTGCCAC  CCCCCATGGA  CTGCCCAGCT      60

GCCTTGTATC  AGCTGATGCT  GGACTGCTGG  CAGAAAGACA  GGAACAACAG  ACCCAAGTTT     120

GAGCAGATTG  TTAGTATTCT  GGACAAGCTT  ATCCGGAATC  CCGGCAGCCT  GAAGGATCAT     180

CA                                                                        182
```

( 2 ) INFORMATION FOR SEQ ID NO: 15:

( i ) SEQUENCE CHARACTERISTICS:
        ( A ) LENGTH: 174 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

```
GCCAAATGGG  TAGCATTGTT  GCTCGGCCTT  CTAGTCTGCC  AGTAGGAAAG  TCCAACCATT      60

AGGTCGGGGA  AGAAGGGTCT  GGATTTGGTT  GACAATGGTT  GGATGGGGGA  TAGAAGCAGA     120

GAGAGAGAGG  GAGGGCAGCT  CAAGGGTATC  TTGCCCCACT  CTGTTTATGC  TGAT           174
```

( 2 ) INFORMATION FOR SEQ ID NO: 16:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

```
CACCTAACAA  TATATCAATT  TTTAAAAAT   GGAATTTCTT  ATGCCCTCTT  TATTTATGGA      60

CATGTATGTC  CATAATGGGA  GACGTTTTCT  TTGGACTGAT  GCTTAATCA   GTGGGTGCTT     120

GGCATTGCTG  AT                                                            132
```

( 2 ) INFORMATION FOR SEQ ID NO: 17:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

```
CAGACACACA  CATGCACACC  ATTCTAGAAT  GCTTCCTTAA  AAGAAGGAGG  GTTGCCCTAG      60

TCTCAAAATC  TTAAAAGCCA  TATGTGCATT  GATTTCTGCA  CAGGTAGGCA  ATTTGTGATT    120
```

TTATTTTTCC TTATG                                                                            135

( 2 ) INFORMATION FOR SEQ ID NO: 18:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 18:

AGGGAACGAG  GCCTTGGAGA  GTGATGCTGA  GAAGCTGAGC  AGCACAGACA  ACGAGGATGA      60

GGAGCTGGGG  ACAGAAGGTG  AGGGATGGCT  GCCCTCAGCC  TACGTGTCCC  TGTCTGCATG     120

TCTTTCTTGG  CTTCTGAGCT  TTGAGGCTGC  CTGTGCTTAT  GGAGACAGCT  GTCTCCAGTT     180

CAGCAGGGTC  CTGGGACCTG  TCTGCTGGAC  AGCGGCTCTG  GATGAGAGGG  TCTCCAGTGT     240

TGGATGAAAT  GGCAGAGCTC  TCACTGAATC  CAGATCCCGT  CTGTTTCTC   CCCATCTCTT     300

TTGGTGGTGT  GAGAAAATGG  AAATCCCTAT  AGGTTTTCC   TAGTTCTAGA  ATTCTTAAAG     360

AATAGGAAGA  AAAATTAAGA  TTTCTTAGAG  TTCAAGTTCA  AAATTTCTTA  GAGTT          415

( 2 ) INFORMATION FOR SEQ ID NO: 19:

( i ) SEQUENCE CHARACTERISTICS:
        ( A ) LENGTH: 471 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 19:

GCCCCAAATG  CCAGGCTGCA  CTGATCTCAT  GTCTGTGTCA  CTGGAACCAA  CAGGCCTGCC      60

TCAACCACTG  TCCACCTGCA  CATCTGAGAG  GCTGGCAGGT  CACCAGGGCT  AGCCGTGCAC     120

GTCAGTTCCT  GGGAAGAAAG  TAGAATGTGA  ATCATCTTCT  CTCAAACGCC  TATCAAAAGC     180

CCAGCTGAGA  TCAATAATTT  GGTGGGAGAA  CAGACCTGTA  CCAATTGGCT  CGGTGTTTGG     240

TGGGGTATTG  TAAATTTGGA  TCCTAAATCA  AAGGGTATCC  CTAGAAGGAC  CCACATGGAA     300

TGGCCTCCTC  CTAAACATCC  CTCCATGTTG  GTACTTCCTG  ACTCTTTTCC  AGCAATCTCA     360

AAGCACAAGA  AGCAGTGGTG  GGAACCCAGG  CCTGGCATCT  TGTTGGAGCC  CATGGTTGGG     420

GGGTAGGAGC  AACTTTACAG  GCCATCAATT  ATGCCCTAT   ACGCACCTCC  C              471

( 2 ) INFORMATION FOR SEQ ID NO: 20:

( i ) SEQUENCE CHARACTERISTICS:
        ( A ) LENGTH: 209 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 20:

GCCCTTTATA  AATACGATTA  GTATGGAGAA  TTGATACATT  AACAGTTAGC  TTTATAAATT      60

GACAGATTTC  TAAATTAACC  TATGGTCCAC  AAATCAAGTT  CTATCACTAT  TTCCTGCCAC     120

CAAAATCAGT  GATGAAGCCT  CTCCCACACT  AAATGAAGAG  TGGCGAGGGA  CAGAATTCCA     180

CTTGTCTTCC  TTTTGCTGCA  CTAACTACA                                          209

( 2 ) INFORMATION FOR SEQ ID NO: 21:

( i ) SEQUENCE CHARACTERISTICS:
        ( A ) LENGTH: 407 base pairs
        ( B ) TYPE: nucleic acid
        ( C ) STRANDEDNESS: single ( D ) TOPOLOGY: linear ( x i ) SEQUENCE DESCRIPTION: SEQ ID NO: 21:

| | | | | | | |
|---|---|---|---|---|---|---|
| CAAGCAGCAT | AGCCTCTCTG | AAACTCAATT | TCCTCACATT | TATAAATGAG | CTTTTATATT | 60 |
| ATTTACAAAC | CTACCTCATA | GAGCAGGTTG | CAGGCTACAT | GAGAAGGTGC | AAGTTCAATG | 120 |
| CCAAGCAGGG | TCCTAGTATT | TAATAAAAGC | TCAATAAATA | TTCATTTTCT | TCTTTCCTTC | 180 |
| TCTTACTTGA | AGTATAACAT | TTGATAATGA | ATTTTCTCAT | TGCAACAATA | ACACCCCTTC | 240 |
| CACTGAGGGA | TTTGTATCCC | TGCTTAAGAA | GCTATTAGTA | TTCTACAGCA | GGACTCACCC | 300 |
| CACACAATCT | TGGCAGGAAT | ACATCCCTCT | ACCTCTCTGG | TCAATAACCT | GCCTGGCCTG | 360 |
| TGACCCCAGG | CTTCCTGGAG | AAGCACCAAG | TCCTCCCAGT | TTCCCCC | | 407 |

( 2 ) INFORMATION FOR SEQ ID NO: 22:

( i ) SEQUENCE CHARACTERISTICS:
    ( A ) LENGTH: 267 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 22:

| | | | | | | |
|---|---|---|---|---|---|---|
| CATTGGTGCA | GCAGGTTTAG | ATGGCTATGT | GCTAGAGTAT | TGCTTTGAAG | GAAGTAAGTA | 60 |
| CAACCAGTAG | ATAAAATGAA | TACTGTCATC | AATAGGTGAG | ATATGTCCCT | CCCCTTTCTG | 120 |
| TTGTCTCTCT | TTCTTGAGAA | CGCATCACCT | TCCTACGAAA | ATAAGATCAA | GCCAAACGTC | 180 |
| ATCCTTCTGA | GATGTATATA | AACTAAGCCC | TTTTTAGTA | CTTGGTGCTT | ATAAATTGAT | 240 |
| ATCTCAAAAG | TATCTTGGCT | AGGCTGC | | | | 267 |

( 2 ) INFORMATION FOR SEQ ID NO: 23:

( i ) SEQUENCE CHARACTERISTICS:
    ( A ) LENGTH: 333 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 23:

| | | | | | | |
|---|---|---|---|---|---|---|
| CATAGTCCAG | GAGCAGAGTT | AGCCAGAATT | GCCTCCTGCT | GCCCCAGCTT | AGAGAGCTCC | 60 |
| CATCTCAATC | ATTGAGCCTG | AAGGCTTCAA | GCCCAAAATG | CAACAAGACC | CCCAGCCTAC | 120 |
| ATTTCTCAGC | TCCCCTGGAG | CCAGTGATCC | TGTAACGCTG | CTGGAGGTCA | GTCTGAGCTA | 180 |
| CCAAGACTGT | CCCTAGACAA | AGGTGGGAGT | CCCCCACACT | GCCAAGACCA | AATCCCTCAC | 240 |
| TCAACCTGCT | GAGGTGTTGG | ATGGGAAAC | AAGAGGCAAA | ACTGAGGCAC | CTGATGCATT | 300 |
| CAGCCCTGCT | TGTGCAGAAG | TGCATTGACT | GCC | | | 333 |

( 2 ) INFORMATION FOR SEQ ID NO: 24:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 24:

| | | | |
|---|---|---|---|
| GGTCCGGATC | CTTCAACTTG | GACACTCGGG | A | 31 |

( 2 ) INFORMATION FOR SEQ ID NO: 25:

( i ) SEQUENCE CHARACTERISTICS:
    ( A ) LENGTH: 24 base pairs (B) TYPE: nucleic acid
(C) STRANDEDNESS: single
(D) TOPOLOGY: linear (xi) SEQUENCE DESCRIPTION: SEQ ID NO: 25:

ATCCTGAGAT TCTGACTCAG GACA 24

(2) INFORMATION FOR SEQ ID NO: 26:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO: 26:

TGCGTTCACC ATTCATGTGG ATGAAGCAG 29

(2) INFORMATION FOR SEQ ID NO: 27:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO: 27:

CTCCTACTTC AACTAACCAG TCCACGAG 28

(2) INFORMATION FOR SEQ ID NO: 28:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 28:

GATGCTTTGA AGTTATCTCT CTTGG 25

(2) INFORMATION FOR SEQ ID NO: 29:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 29:

ATCAGTGTGG CAGATATAAT GGACC 25

(2) INFORMATION FOR SEQ ID NO: 30:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 30:

GCCCCAAATG CCAGGCTGCA CTGAT 25

(2) INFORMATION FOR SEQ ID NO: 31:

(i) SEQUENCE CHARACTERISTICS:
(A) LENGTH: 25 base pairs
(B) TYPE: nucleic acid
(C) STRANDEDNESS: single -continued (D) TOPOLOGY: linear (xi) SEQUENCE DESCRIPTION: SEQ ID NO: 31:

GCCAGAAGAC AAGAGTGTGA GCCTT 25

(2) INFORMATION FOR SEQ ID NO: 32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 32:

GCTTCAGGGT GGTCCAATTA GAGTT 25

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 33:

TCCAACAACG ACACATTCAG GAGTT 25

(2) INFORMATION FOR SEQ ID NO: 34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 34:

GGACACAGAG TAAGATACCC ACTGA 25

(2) INFORMATION FOR SEQ ID NO: 35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 35:

CCTCGGTCTT TGGTCTTTGC ATATC 25

(2) INFORMATION FOR SEQ ID NO: 36:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 36:

ACAAGGAAAG TGTCCCTATC TCTGA 25

(2) INFORMATION FOR SEQ ID NO: 37:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (x i) SEQUENCE DESCRIPTION: SEQ ID NO: 37:

CTCGAGGTCT CCCACTGAAG TGCTC 25

(2) INFORMATION FOR SEQ ID NO: 38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (x i) SEQUENCE DESCRIPTION: SEQ ID NO: 38:

CACTGCACAT TAAGATGGAG CCCGA 25

(2) INFORMATION FOR SEQ ID NO: 39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (x i) SEQUENCE DESCRIPTION: SEQ ID NO: 39:

CCTGTAGAAG TTCTGCTGCG TGTGG 25

(2) INFORMATION FOR SEQ ID NO: 40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (x i) SEQUENCE DESCRIPTION: SEQ ID NO: 40:

CGAGCTGCCT GACGGCCAGG TCATC 25

(2) INFORMATION FOR SEQ ID NO: 41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (x i) SEQUENCE DESCRIPTION: SEQ ID NO: 41:

GAAGCATTTG CGGTGGACGA TGGAG 25

(2) INFORMATION FOR SEQ ID NO: 42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO: 42:

ACATTGAAGC ACTCCGCGAC 20

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO: 43:

| AGAGTGGCAG CAACCAAGCT | 20 |

( 2 ) INFORMATION FOR SEQ ID NO: 44:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 44:

| CCCCTTTTAT AGTAAGAGCC CCAGA | 25 |

( 2 ) INFORMATION FOR SEQ ID NO: 45:

( i ) SEQUENCE CHARACTERISTICS:
        ( A ) LENGTH: 369 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 45:

| CCATAAGAGA AATGATTGGT AGGTTTGCAT GAAATTTTAA AATTTCCTGT GGCGTAAGGC | 60 |
| ATCCCATAAC GAAGCCAAAA GGTGAGTGAT AGACTGGGAG AAATAACTGC CAGACGTTGC | 120 |
| CAGACAAAGA TTTCATATTT CTAATATGCT AGAGTACCTT TAATTTGATA AGAAAAGAT | 180 |
| AAGCAATCCT GTAATAAAAT GGACATTTTA CAAGGAGTG CTTGCAAATG GCCAGTGAAT | 240 |
| TTATGCAAAT ATGTTCAGGG AAATAGGAAT GAAAACGAGA TTCCACTTTT TCATCATCCA | 300 |
| TTTGATTGGC AAGAAATTTT TAAAAGAGTA ATACCTAGTG AATCACTCAT GTAGGAAAAT | 360 |
| GGGTTGGTG | 369 |

( 2 ) INFORMATION FOR SEQ ID NO: 46:

( i ) SEQUENCE CHARACTERISTICS:
        ( A ) LENGTH: 301 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION:212
        ( D ) OTHER INFORMATION:/mod_base=OTHER
            / note= "N = A, C, G or T"

( x i ) SEQUENCE DESCRIPTION: SEQ ID NO: 46:

| GCCCTTGAAG AGTGTAACCA AGAAGCATCT CTCAATCAAT GAACCTGAGA CAGCCTGTTC | 60 |
| ACTTCTGACC ATCATTCTTG TCCTTTAGAT CTCAGTTTCA AATTCATTTC TTCTAGACAT | 120 |
| TCATCTCTTC CCATGTTTAA TCTGGAACCA TCTACCCTTC CACCAGACCA ATTATCCTGG | 180 |
| CAAATTAATG TAATAGACCA GTATTAATTA TNTGGTTGTA TGTCTTAACA ACATTCTAGG | 240 |
| TGCTGTGCCA AAAACAAATG AATAGCAACA CAAGGTCTTC TTGGTTACAC TCTTCAAGGG | 300 |
| C | 301 |

( 2 ) INFORMATION FOR SEQ ID NO: 47:

( i ) SEQUENCE CHARACTERISTICS:
        ( A ) LENGTH: 3061 base pairs
        ( B ) TYPE: nucleic acid
        ( C ) STRANDEDNESS: single
        ( D ) TOPOLOGY: linear ( i x ) FEATURE:
        ( A ) NAME/KEY: CDS (B) LOCATION:15..1172

(xi) SEQUENCE DESCRIPTION: SEQ ID NO: 47:

```
CGGCTCTCCT CAAC ATG AGA GCT GCA CCC CTC CTC CTG GCC AGG GCA GCA           50
                Met Arg Ala Ala Pro Leu Leu Leu Ala Arg Ala Ala
                 1            5                        10

AGC CTT AGC CTT GGC TTC TTG TTT CTG CTT TTT TTC TGG CTA GAC CGA           98
Ser Leu Ser Leu Gly Phe Leu Phe Leu Leu Phe Phe Trp Leu Asp Arg
             15                  20                  25

AGT GTA CTA GCC AAG GAG TTG AAG TTT GTG ACT TTG GTG TTT CGG CAT          146
Ser Val Leu Ala Lys Glu Leu Lys Phe Val Thr Leu Val Phe Arg His
         30                  35                  40

GGA GAC CGA AGT CCC ATT GAC ACC TTT CCC ACT GAC CCC ATA AAG GAA          194
Gly Asp Arg Ser Pro Ile Asp Thr Phe Pro Thr Asp Pro Ile Lys Glu
 45                  50                  55                  60

TCC TCA TGG CCA CAA GGA TTT GGC CAA CTC ACC CAG CTG GGC ATG GAG          242
Ser Ser Trp Pro Gln Gly Phe Gly Gln Leu Thr Gln Leu Gly Met Glu
                 65                  70                  75

CAG CAT TAT GAA CTT GGA GAG TAT ATA AGA AAG AGA TAT AGA AAA TTC          290
Gln His Tyr Glu Leu Gly Glu Tyr Ile Arg Lys Arg Tyr Arg Lys Phe
             80                  85                  90

TTG AAT GAG TCC TAT AAA CAT GAA CAG GTT TAT ATT CGA AGC ACA GAC          338
Leu Asn Glu Ser Tyr Lys His Glu Gln Val Tyr Ile Arg Ser Thr Asp
         95                 100                 105

GTT GAC CGG ACT TTG ATG AGT GCT ATG ACA AAC CTG GCA GCC CTG TTT          386
Val Asp Arg Thr Leu Met Ser Ala Met Thr Asn Leu Ala Ala Leu Phe
110                 115                 120

CCC CCA GAA GGT GTC AGC ATC TGG AAT CCT ATC CTA CTC TGG CAG CCC          434
Pro Pro Glu Gly Val Ser Ile Trp Asn Pro Ile Leu Leu Trp Gln Pro
125                 130                 135                 140

ATC CCG GTG CAC ACA GTT CCT CTT TCT GAA GAT CAG TTG CTA TAC CTG          482
Ile Pro Val His Thr Val Pro Leu Ser Glu Asp Gln Leu Leu Tyr Leu
                145                 150                 155

CCT TTC AGG AAC TGC CCT CGT TTT CAA GAA CTT GAG AGT GAG ACT TTG          530
Pro Phe Arg Asn Cys Pro Arg Phe Gln Glu Leu Glu Ser Glu Thr Leu
            160                 165                 170

AAA TCA GAG GAA TTC CAG AAG AGG CTG CAC CCT TAT AAG GAT TTT ATA          578
Lys Ser Glu Glu Phe Gln Lys Arg Leu His Pro Tyr Lys Asp Phe Ile
        175                 180                 185

GCT ACC TTG GGA AAA CTT TCA GGA TTA CAT GGC CAG GAC CTT TTT GGA          626
Ala Thr Leu Gly Lys Leu Ser Gly Leu His Gly Gln Asp Leu Phe Gly
190                 195                 200

ATT TGG AGT AAA GTC TAC GAC CCT TTA TAT TGT GAG AGT GTT CAC AAT          674
Ile Trp Ser Lys Val Tyr Asp Pro Leu Tyr Cys Glu Ser Val His Asn
205                 210                 215                 220

TTC ACT TTA CCC TCC TGG GCC ACT GAG GAC ACC ATG ACT AAG TTG AGA          722
Phe Thr Leu Pro Ser Trp Ala Thr Glu Asp Thr Met Thr Lys Leu Arg
                225                 230                 235

GAA TTG TCA GAA TTG TCC CTC CTG TCC CTC TAT GGA ATT CAC AAG CAG          770
Glu Leu Ser Glu Leu Ser Leu Leu Ser Leu Tyr Gly Ile His Lys Gln
            240                 245                 250

AAA GAG AAA TCT AGG CTC CAA GGG GGT GTC CTG GTC AAT GAA ATC CTC          818
Lys Glu Lys Ser Arg Leu Gln Gly Gly Val Leu Val Asn Glu Ile Leu
        255                 260                 265

AAT CAC ATG AAG AGA GCA ACT CAG ATA CCA AGC TAC AAA AAA CTT ATC          866
Asn His Met Lys Arg Ala Thr Gln Ile Pro Ser Tyr Lys Lys Leu Ile
270                 275                 280

ATG TAT TCT GCG CAT GAC ACT ACT GTG AGT GGC CTA CAG ATG GCG CTA          914
Met Tyr Ser Ala His Asp Thr Thr Val Ser Gly Leu Gln Met Ala Leu
285                 290                 295                 300
```

| | | | | | | | | | | | | | | | | |
|---|---|---|---|---|---|---|---|---|---|---|---|---|---|---|---|---|
| GAT | GTT | TAC | AAC | GGA | CTC | CTT | CCT | CCC | TAT | GCT | TCT | TGC | CAC | TTG | ACG | 962 |
| Asp | Val | Tyr | Asn | Gly | Leu | Leu | Pro | Pro | Tyr | Ala | Ser | Cys | His | Leu | Thr | |
| | | | 305 | | | | | 310 | | | | | 315 | | | |
| GAA | TTG | TAC | TTT | GAG | AAG | GGG | GAG | TAC | TTT | GTG | GAG | ATG | TAC | TAT | CGG | 1010 |
| Glu | Leu | Tyr | Phe | Glu | Lys | Gly | Glu | Tyr | Phe | Val | Glu | Met | Tyr | Tyr | Arg | |
| | | | 320 | | | | | 325 | | | | | 330 | | | |
| AAT | GAG | ACG | CAG | CAC | GAG | CCG | TAT | CCC | CTC | ATG | CTA | CCT | GGC | TGC | AGC | 1058 |
| Asn | Glu | Thr | Gln | His | Glu | Pro | Tyr | Pro | Leu | Met | Leu | Pro | Gly | Cys | Ser | |
| | | 335 | | | | | 340 | | | | | 345 | | | | |
| CCT | AGC | TGT | CCT | CTG | GAG | AGG | TTT | GCT | GAG | CTG | GTT | GGC | CCT | GTG | ATC | 1106 |
| Pro | Ser | Cys | Pro | Leu | Glu | Arg | Phe | Ala | Glu | Leu | Val | Gly | Pro | Val | Ile | |
| | 350 | | | | | 355 | | | | | 360 | | | | | |
| CCT | CAA | GAC | TGG | TCC | ACG | GAG | TGT | ATG | ACC | ACA | AAC | AGC | CAT | CAA | GGT | 1154 |
| Pro | Gln | Asp | Trp | Ser | Thr | Glu | Cys | Met | Thr | Thr | Asn | Ser | His | Gln | Gly | |
| 365 | | | | | 370 | | | | | 375 | | | | | 380 | |
| ACT | GAG | GAC | AGT | ACA | GAT | TAGTGTGCAC | AGAGATCTCT | GTAGAAGAG | | | | | | | | 1202 |
| Thr | Glu | Asp | Ser | Thr | Asp | | | | | | | | | | | |
| | | | | 385 | | | | | | | | | | | | |

| | | | | |
|---|---|---|---|---|
| TAGCTGCCCT | TTCTCAGGGC | AGATGATGCT | TGAGAACAT | ACTTTGGCCA | TTACCCCCA | 1262 |
| GCTTTGAGGA | AAATGGGCTT | TGGATGATTA | TTTTATGTTT | TAGGGACCCC | CAACCTCAGG | 1322 |
| CAATTCCTAC | CTCTTCACCT | GACCCTGCCC | CCACTTGCCA | TAAAACTTAG | CTAAGTTTTG | 1382 |
| TTTTGTTTTT | CAGCGTTAAT | GTAAAGGGGC | AGCAGTGCCA | AAATATAATC | AGAGATAAAG | 1442 |
| CTTAGGTCAA | AGTTCATAGA | GTTCCCATGA | ACTATATGAC | TGGCCACACA | GGATCTTTTG | 1502 |
| TATTTAAGGA | TTCTGAGATT | TTGCTTGAGC | AGGATTAGAT | AAGTCTGTTC | TTTAAATTTC | 1562 |
| TGAAATGGAA | CAGATTTCAA | AAAAAATTCC | CACAATCTAG | GGTGGGAACA | AGGAAGGAAA | 1622 |
| GATGTGAATA | GGCTGATGGG | GAAAAAACCA | ATTTACCCAT | CAGTTCCAGC | CTTCTCTCAA | 1682 |
| GGAGAGGCAA | AGAAAGGAGA | TACAGTGGAG | ACATCTGGAA | AGTTTTCTCC | ACTGGAAAAC | 1742 |
| TGCTACTATC | TGTTTTTATA | TTTCTGTTAA | AATATATGAG | CTACAGAAC | TAAAAATTAA | 1802 |
| AACCTCTTTG | TGTCCCTTGG | TCCTGGAACA | TTTATGTTCC | TTTTAAAGAA | ACAAAAATCA | 1862 |
| AACTTTACAG | AAAGATTTGA | TGTATGTAAT | ACATATAGCA | GCTCTTGAAG | TATATATATC | 1922 |
| ATAGCAAATA | AGTCATCTGA | TGAGAACAAG | CTATTTGGGC | ACAACACATC | AGGAAAGAGA | 1982 |
| GCACCACGTG | ATGGAGTTTC | TCCAGAAGCT | CCAGTGATAA | GAGATGTTGA | CTCTAAAGTT | 2042 |
| GATTTAAGGC | CAGGCATGGT | GGTTTACGCC | TATAATCCCA | GCATTTGGG | ACTCCGAGGT | 2102 |
| GGGCAGATCA | CTTGAGCTCA | GGAGCTCAAG | ATCAGCCTGG | CAACATGGT | GAAACCTTGT | 2162 |
| CTCTACATAA | AATACAAAAA | CTTAGATGGG | CATGGTGCTG | TGTGCCTATA | GTCCACTACT | 2222 |
| TGTGGGGCTA | AGGCAGGAGG | ATCACTTGAG | CCCCGGAGGT | CGAGGCTACA | GTGACCCAAG | 2282 |
| AGTGCACTAC | TGTACTCCAG | CCAGGGCAAG | AGAGCGAGAC | CCTGTCTCAA | TAAATAAATA | 2342 |
| AATAAATAAA | TAAATAAATA | AATAAAAACA | AAGTTGATTA | AGAAAGGAAG | TATAGGCCAG | 2402 |
| GCACAGTGGC | TCACACCTGT | AATCCTTGCA | TTTTGGAAGG | CTGAGGCAGG | AGGATCACTT | 2462 |
| TAGGCCTGGT | GTGTTCAAGA | CCAGCCTGGT | CAACATAGTG | AGACACTGTC | TCTACCAAAA | 2522 |
| AAAGGAAGGA | AGGGACACAT | ATCAAACTGA | AACAAATTA | GAAATGTAAT | TATGTTATGT | 2582 |
| TCTAAGTGCC | TCCAAGTTCA | AAACTTATTG | GAATGTTGAG | AGTGTGGTTA | CGAAATACGT | 2642 |
| TAGGAGGACA | AAAGGAATGT | GTAAGTCTTT | AATGCCGATA | TCTTCAGAAA | ACCTAAGCAA | 2702 |
| ACTTACAGGT | CCTGCTGAAA | CTGCCCACTC | TGCAAGAAGA | AATCATGATA | TAGCTTTCCA | 2762 |
| TGTGGCAGAT | CTACATGTCT | AGAGAACACT | GTGCTCTATT | ACCATTATGG | ATAAAGATGA | 2822 |
| GATGGTTTCT | AGAGATGGTT | TCTACTGGCT | GCCAGAATCT | AGAGCAAAGC | CATCCCCCCT | 2882 |

```
CCTGGTTGGT CACAGAATGA CTGACAAAGA CATCGATTGA TATGCTTCTT TGTGTTATTT        2942

CCCTCCCAAG TAAATGTTTG TCCTTGGGTC CATTTTCTAT GCTTGTAACT GTCTTCTAGC        3002

AGTGAGCCAA ATGTAAAATA GTGAATAAAG TCATTATTAG GAAGTTCAAA AAAAAAAA          3061
```

( 2 ) INFORMATION FOR SEQ ID NO: 48:

( i ) SEQUENCE CHARACTERISTICS:
        ( A ) LENGTH: 386 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 48:

```
Met  Arg  Ala  Ala  Pro  Leu  Leu  Leu  Ala  Arg  Ala  Ala  Ser  Leu  Ser  Leu
 1              5                        10                       15

Gly  Phe  Leu  Phe  Leu  Leu  Phe  Phe  Trp  Leu  Asp  Arg  Ser  Val  Leu  Ala
              20                        25                       30

Lys  Glu  Leu  Lys  Phe  Val  Thr  Leu  Val  Phe  Arg  His  Gly  Asp  Arg  Ser
              35                        40                       45

Pro  Ile  Asp  Thr  Phe  Pro  Thr  Asp  Pro  Ile  Lys  Glu  Ser  Ser  Trp  Pro
         50                        55                       60

Gln  Gly  Phe  Gly  Gln  Leu  Thr  Gln  Leu  Gly  Met  Glu  Gln  His  Tyr  Glu
 65                       70                        75                       80

Leu  Gly  Glu  Tyr  Ile  Arg  Lys  Arg  Tyr  Arg  Lys  Phe  Leu  Asn  Glu  Ser
                   85                        90                       95

Tyr  Lys  His  Glu  Gln  Val  Tyr  Ile  Arg  Ser  Thr  Asp  Val  Asp  Arg  Thr
                  100                       105                      110

Leu  Met  Ser  Ala  Met  Thr  Asn  Leu  Ala  Ala  Leu  Phe  Pro  Pro  Glu  Gly
              115                       120                      125

Val  Ser  Ile  Trp  Asn  Pro  Ile  Leu  Leu  Trp  Gln  Pro  Ile  Pro  Val  His
         130                       135                      140

Thr  Val  Pro  Leu  Ser  Glu  Asp  Gln  Leu  Leu  Tyr  Leu  Pro  Phe  Arg  Asn
145                       150                       155                     160

Cys  Pro  Arg  Phe  Gln  Glu  Leu  Glu  Ser  Glu  Thr  Leu  Lys  Ser  Glu  Glu
              165                       170                      175

Phe  Gln  Lys  Arg  Leu  His  Pro  Tyr  Lys  Asp  Phe  Ile  Ala  Thr  Leu  Gly
              180                       185                      190

Lys  Leu  Ser  Gly  Leu  His  Gly  Gln  Asp  Leu  Phe  Gly  Ile  Trp  Ser  Lys
              195                       200                      205

Val  Tyr  Asp  Pro  Leu  Tyr  Cys  Glu  Ser  Val  His  Asn  Phe  Thr  Leu  Pro
         210                       215                      220

Ser  Trp  Ala  Thr  Glu  Asp  Thr  Met  Thr  Lys  Leu  Arg  Glu  Leu  Ser  Glu
225                       230                       235                     240

Leu  Ser  Leu  Leu  Ser  Leu  Tyr  Gly  Ile  His  Lys  Gln  Lys  Glu  Lys  Ser
                   245                       250                      255

Arg  Leu  Gln  Gly  Gly  Val  Leu  Val  Asn  Glu  Ile  Leu  Asn  His  Met  Lys
              260                       265                      270

Arg  Ala  Thr  Gln  Ile  Pro  Ser  Tyr  Lys  Lys  Leu  Ile  Met  Tyr  Ser  Ala
              275                       280                      285

His  Asp  Thr  Thr  Val  Ser  Gly  Leu  Gln  Met  Ala  Leu  Asp  Val  Tyr  Asn
              290                       295                      300

Gly  Leu  Leu  Pro  Pro  Tyr  Ala  Ser  Cys  His  Leu  Thr  Glu  Leu  Tyr  Phe
305                       310                       315                     320

Glu  Lys  Gly  Glu  Tyr  Phe  Val  Glu  Met  Tyr  Tyr  Arg  Asn  Glu  Thr  Gln
                   325                       330                      335
```

| His | Glu | Pro | Tyr<br>340 | Pro | Leu | Met | Leu | Pro<br>345 | Gly | Cys | Ser | Pro<br>350 | Cys | Pro |
|-----|-----|-----|------|-----|-----|-----|-----|------|-----|-----|-----|------|-----|-----|
| Leu | Glu | Arg<br>355 | Phe | Ala | Glu | Leu | Val<br>360 | Gly | Pro | Val | Ile | Pro<br>365 | Gln | Asp | Trp |
| Ser | Thr<br>370 | Glu | Cys | Met | Thr | Thr<br>375 | Asn | Ser | His | Gln | Gly<br>380 | Thr | Glu | Asp | Ser |

Thr Asp
385

(2) INFORMATION FOR SEQ ID NO: 49:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 49:

TCGCTCCACA TTCATCCTTT CT      22

(2) INFORMATION FOR SEQ ID NO: 50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 50:

TGATCCCTGG GTGATATAGA GCATA      25

(2) INFORMATION FOR SEQ ID NO: 51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 51:

GCCCCACATC TGAACAAGCT AATAA      25

(2) INFORMATION FOR SEQ ID NO: 52:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 52:

TGCGCCCTTC ATACAGGCAG AGTTG      25

(2) INFORMATION FOR SEQ ID NO: 53:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 53:

CACGATGCCA TTCTGCCATT TCTGT      25

(2) INFORMATION FOR SEQ ID NO: 54:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 54:

GGAAGAGATG GAATAGAAAC TGTAA                                        25

( 2 ) INFORMATION FOR SEQ ID NO: 55:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 55:

GGGACAGAAG GTGAGGGATG G                                          21

( 2 ) INFORMATION FOR SEQ ID NO: 56:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 56:

AGACGGGATC TGGATTCAGT GAGAG                                        25

( 2 ) INFORMATION FOR SEQ ID NO: 57:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 57:

CACTGGAACC AACAGGCTG CCTCAAC                                27

( 2 ) INFORMATION FOR SEQ ID NO: 58:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 58:

CCGAGCCAAT TGGTACAGGT CTGTTCTCCC                              30

( 2 ) INFORMATION FOR SEQ ID NO: 59:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 59:

CCTCAAGACT GGTCCACGGA GTGTATGA                                28

( 2 ) INFORMATION FOR SEQ ID NO: 60:

( i ) SEQUENCE CHARACTERISTICS:

```
            ( A ) LENGTH: 30 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 60:
```

GGGTAATGGC CAAAGTATGT TCTCAAAGCA                 30

( 2 ) INFORMATION FOR SEQ ID NO: 61:

```
     ( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 61:
```

AAACAAACGT CTTTGGGTAA A                          21

( 2 ) INFORMATION FOR SEQ ID NO: 62:

```
     ( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 62:
```

CTGGACAAAG AGGAATATGA                            20

( 2 ) INFORMATION FOR SEQ ID NO: 63:

```
     ( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 63:
```

GCCCTTTATA AATACGATTA GTATGGAG                   28

( 2 ) INFORMATION FOR SEQ ID NO: 64:

```
     ( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 64:
```

TGTAGTTAGT GCAGCAAAAG GAAGA                      25

( 2 ) INFORMATION FOR SEQ ID NO: 65:

```
     ( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 65:
```

GATGTAATTA AAGCTGTAGA TGAGGG                     26

( 2 ) INFORMATION FOR SEQ ID NO: 66:

```
     ( i ) SEQUENCE CHARACTERISTICS:
            ( A ) LENGTH: 28 base pairs
            ( B ) TYPE: nucleic acid
```

(C) STRANDEDNESS: single
(D) TOPOLOGY: linear (xi) SEQUENCE DESCRIPTION: SEQ ID NO: 66:

GAATACTAAC AATCTGCTCA AACTTGGG    28

(2) INFORMATION FOR SEQ ID NO: 67:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 67:

GCCAAATGGG TAGCATTGTT GCTCGG    26

(2) INFORMATION FOR SEQ ID NO: 68:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 68:

CAGAGTGGGG CAAGATACCC TTGAG    25

(2) INFORMATION FOR SEQ ID NO: 69:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 69:

AATGGAATTT CTTATGCCCT C    21

(2) INFORMATION FOR SEQ ID NO: 70:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 70:

CAATGCCAAG CACCCACTGA TTC    23

(2) INFORMATION FOR SEQ ID NO: 71:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 71:

ACACAGACAC ACACATGCAC ACCA    24

(2) INFORMATION FOR SEQ ID NO: 72:

(i) SEQUENCE CHARACTERISTICS:
(A) LENGTH: 20 base pairs
(B) TYPE: nucleic acid
(C) STRANDEDNESS: single
(D) TOPOLOGY: linear ( x i ) SEQUENCE DESCRIPTION: SEQ ID NO: 72:

CCTACCTGTG CAGAAATCAA                    20

( 2 ) INFORMATION FOR SEQ ID NO: 73:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 73:

AGCAGCATAG CCTCTCTGAA ACTC                    24

( 2 ) INFORMATION FOR SEQ ID NO: 74:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 74:

CCTTCTCATG TAGCCTGCAA CCTGCTC                    27

( 2 ) INFORMATION FOR SEQ ID NO: 75:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 75:

CATTGGTGCA GCAGGTTTAG ATGG                    24

( 2 ) INFORMATION FOR SEQ ID NO: 76:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 76:

GAGATATCAA TTTATAAGCA CCAAG                    25

( 2 ) INFORMATION FOR SEQ ID NO: 77:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 77:

ATCTCAATCA TTGAGCCTGA AGG                    23

( 2 ) INFORMATION FOR SEQ ID NO: 78:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 78:

-continued

```
CAGCAGGTTG AGTGAGGGAT TTGG                                                    24
```

(2) INFORMATION FOR SEQ ID NO: 79:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 79:

```
CGCCTCAGGC TGGGGCAGCA TT                                                      22
```

(2) INFORMATION FOR SEQ ID NO: 80:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 80:

```
ACAGTGGAAG AGTCTCATTC GAGAT                                                   25
```

(2) INFORMATION FOR SEQ ID NO: 81:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 81:

```
CGAGCTGCCT GACGGCCAGG TCATC                                                   25
```

(2) INFORMATION FOR SEQ ID NO: 82:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 82:

```
GAAGCATTTG CGGTGGACGA TGGAG                                                   25
```